US011510748B2

(12) United States Patent
Mann et al.

(10) Patent No.: US 11,510,748 B2
(45) Date of Patent: Nov. 29, 2022

(54) MEDICAL SUPPLIES CABINET

(71) Applicant: XORIA LIMITED, Middleton Christchurch (NZ)

(72) Inventors: Stephen Ian Mann, Northwood (NZ); Peter James Montgomery, Ohoka (NZ); Matthew Claridge, Riccarton (NZ); James Wellacott, Bishopdale (NZ)

(73) Assignee: XORIA LIMITED, Middleton Christchurch (NZ)

(*) Notice: Subject to any disclaimer, the term of this patent is extended or adjusted under 35 U.S.C. 154(b) by 161 days.

(21) Appl. No.: 16/651,821

(22) PCT Filed: Sep. 28, 2018

(86) PCT No.: PCT/IB2018/057530
§ 371 (c)(1),
(2) Date: Mar. 27, 2020

(87) PCT Pub. No.: WO2019/064244
PCT Pub. Date: Apr. 4, 2019

(65) Prior Publication Data
US 2020/0253679 A1    Aug. 13, 2020

(30) Foreign Application Priority Data

Sep. 29, 2017  (NZ) .................................. 735981
Jun. 12, 2018  (NZ) .................................. 743404

(51) Int. Cl.
*A61B 50/10*    (2016.01)
*G16H 40/20*   (2018.01)
(Continued)

(52) U.S. Cl.
CPC .............. *A61B 50/10* (2016.02); *A47B 67/02* (2013.01); *G06K 7/10366* (2013.01);
(Continued)

(58) Field of Classification Search
CPC ...... G06Q 10/087; G16H 40/20; G16H 20/13; A47B 67/02; A61B 50/13; A61B 2050/105; A61B 50/10
(Continued)

(56) References Cited

U.S. PATENT DOCUMENTS 8,842,183 B2 * 9/2014 Glickman ................ B25H 3/00
348/165
2004/0046020 A1   3/2004 Andreasson et al.
(Continued)

FOREIGN PATENT DOCUMENTS

WO    WO-9714104 A1    4/1997
WO    WO-2016181352    11/2016
WO    WO-2019064244 A1    4/2019

OTHER PUBLICATIONS https://web.archive.org/web/20160728045609/http://www.clevermedkits.co.nz/ (Year: 2016).*
http://www.stuff.co.nz/the-press/business/opensource/9934246/Cupboard-never-bare-with-hi-tech-kit (Year: 2014).*
"International Application No. PCT/IB2018/057530, International Preliminary Report on Patentability dated Apr. 9, 2020", 6 pgs.
(Continued)

*Primary Examiner* — Timothy R Waggoner
(74) *Attorney, Agent, or Firm* — Schwegman Lundberg & Woessner, P.A.

(57) ABSTRACT

A medical supplies cabinet is disclosed. The cabinet comprises a housing presenting a medical supplies storage zone at where there is provided at least one medical supplies receptacle. The receptacle(s) is/are of a shape and configuration to be able to at least partly receive and hold at least one medical item. A sensor is associated with the receptacle(s). The sensor is configured to generate a signal indicative of the presence and/or absence, or removal of the medical item in/from the receptacle.

15 Claims, 31 Drawing Sheets

(51) Int. Cl.
  *A47B 67/02*    (2006.01)
  *G06K 7/10*     (2006.01)
  *G06Q 10/08*    (2012.01)
  *A61B 50/00*    (2016.01)
  *A61B 90/00*    (2016.01)
  *G01G 19/42*    (2006.01)
  *G01V 3/08*     (2006.01)
  *G01V 8/10*     (2006.01)
  *G01V 15/00*    (2006.01)
  *G08B 5/36*     (2006.01)
  *G08B 21/18*    (2006.01)

(52) U.S. Cl.
  CPC ........... *G06Q 10/087* (2013.01); *G16H 40/20* (2018.01); *A47B 2067/025* (2013.01); *A61B 2050/0053* (2016.02); *A61B 2050/105* (2016.02); *A61B 2090/0805* (2016.02); *G01G 19/42* (2013.01); *G01V 3/08* (2013.01); *G01V 8/10* (2013.01); *G01V 15/00* (2013.01); *G08B 5/36* (2013.01); *G08B 21/18* (2013.01)

(58) Field of Classification Search
  USPC .......................................................... 700/236
  See application file for complete search history.

(56) References Cited

U.S. PATENT DOCUMENTS

| | | |
|---|---|---|
| 2009/0319399 A1 | 12/2009 | Resta et al. |
| 2011/0010275 A1 | 1/2011 | Hull |
| 2016/0328813 A1* | 11/2016 | Montgomery ....... G06Q 10/087 |
| 2016/0379022 A1* | 12/2016 | Elizondo, II ........... G16H 40/20 340/10.1 |

OTHER PUBLICATIONS

"CleverMedkits", Wayback Machine, https://web.archive.org/web/20170406010350/http://www.clevermedkits.co.nz/, (Jun. 13, 2015), 16 pgs.

"International Application No. PCT/IB2018/057530, International Search Report and Written Opinion dated Nov. 23, 2018", (Nov. 23, 2018), 9 pgs.

"Tool Foam Organizer—101 Hacks that will Blow Your Mind", Wayback Machine, https://web.archive.org/web/20150613073220/https://www.creativesafetysupply.com/content/education-research/101-tool-foam-organizer-hacks/index.html, (Jun. 13, 2015), 37 pgs.

"A Better First Aid Kit That Makes Suggestions and Knows What's Missing", https://web.archive.org/web/20140731195730/https://www.gizmodo.com.au/2014/07/a-better-first-aid-kit-that-makes-suggestions-and-knows-whats-missing/, (Sep. 16, 2022), 3 pgs.

"Australian Application No. 2018343311, Examination report No. 1 dated Sep. 7, 2022", (Sep. 7, 2022), 4 pgs.

* cited by examiner

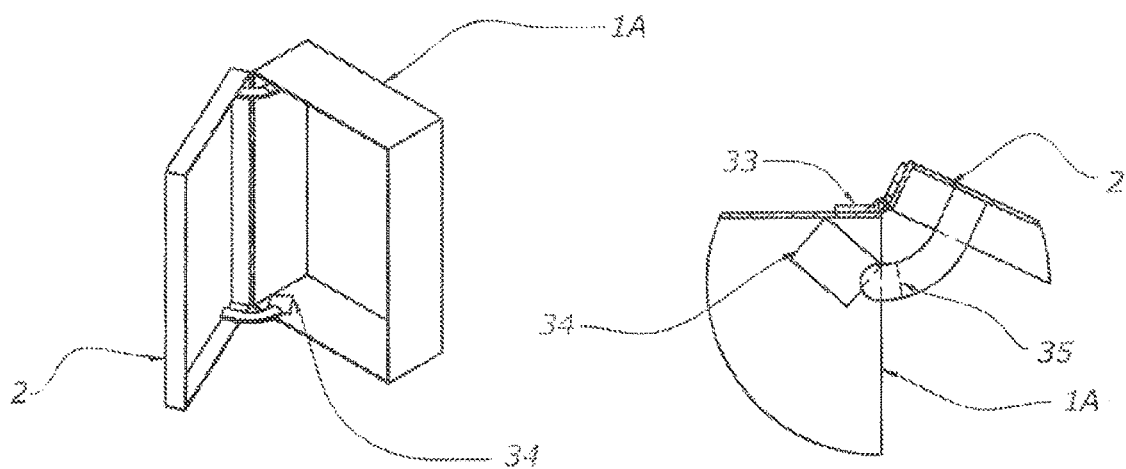
*FIGURE 6A*  *FIGURE 6B*
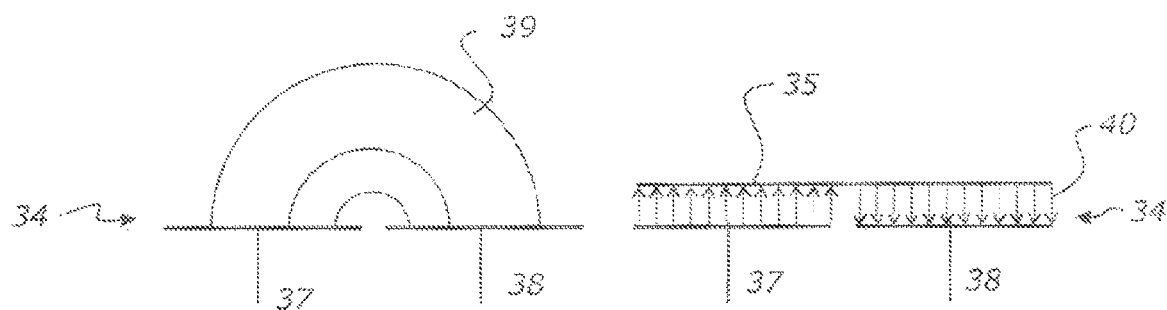
*FIGURE 7*  *FIGURE 8*

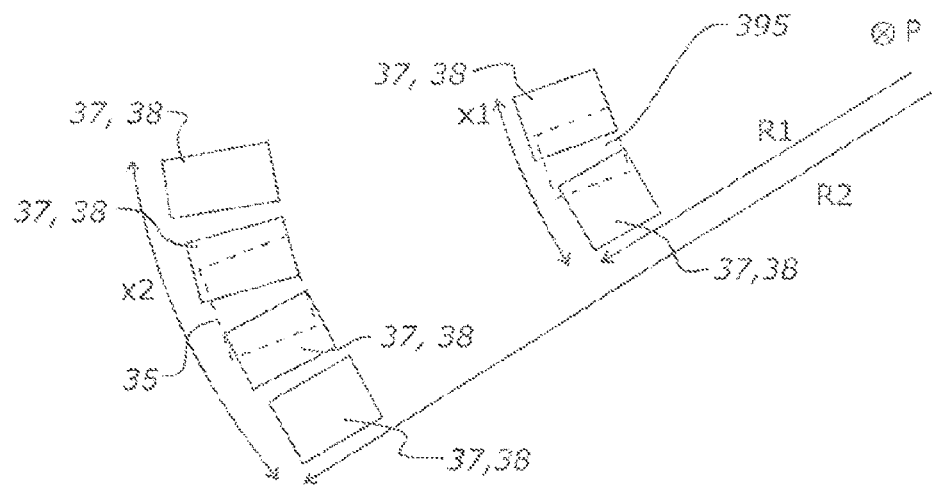
*FIGURE 17*
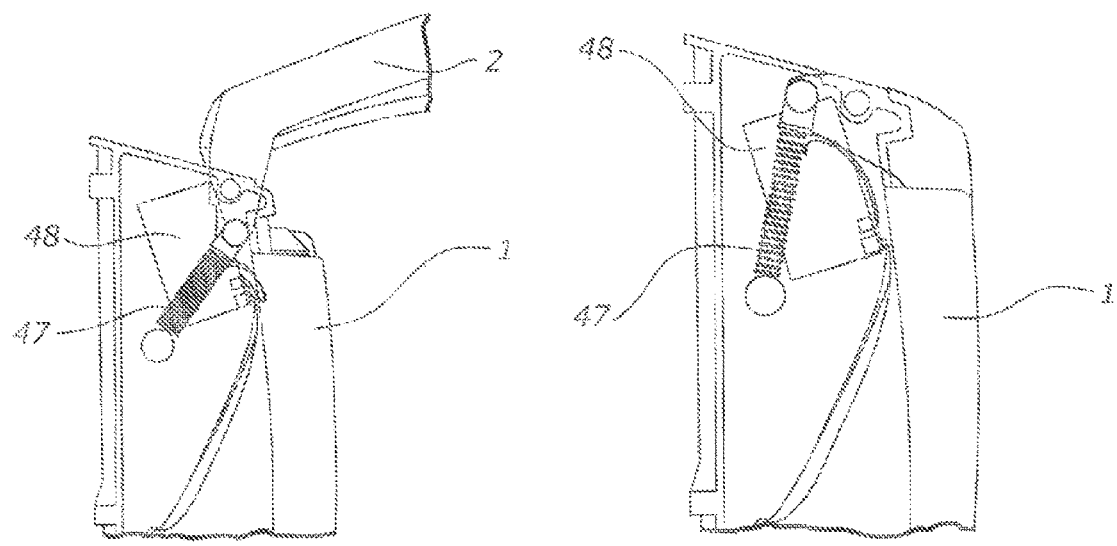
*FIGURE 17A*  *FIGURE 17B*

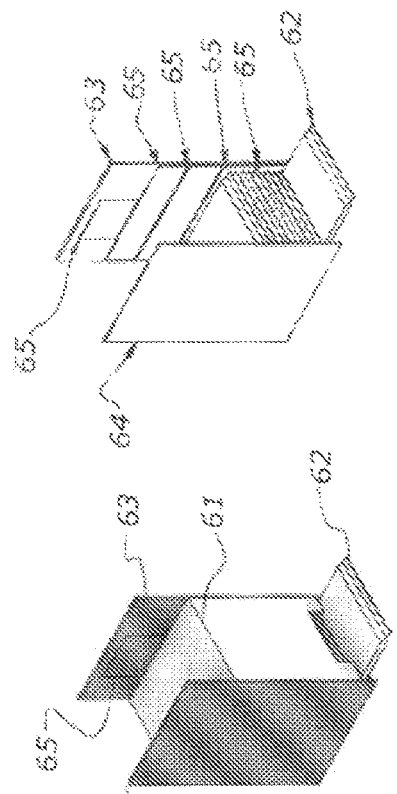
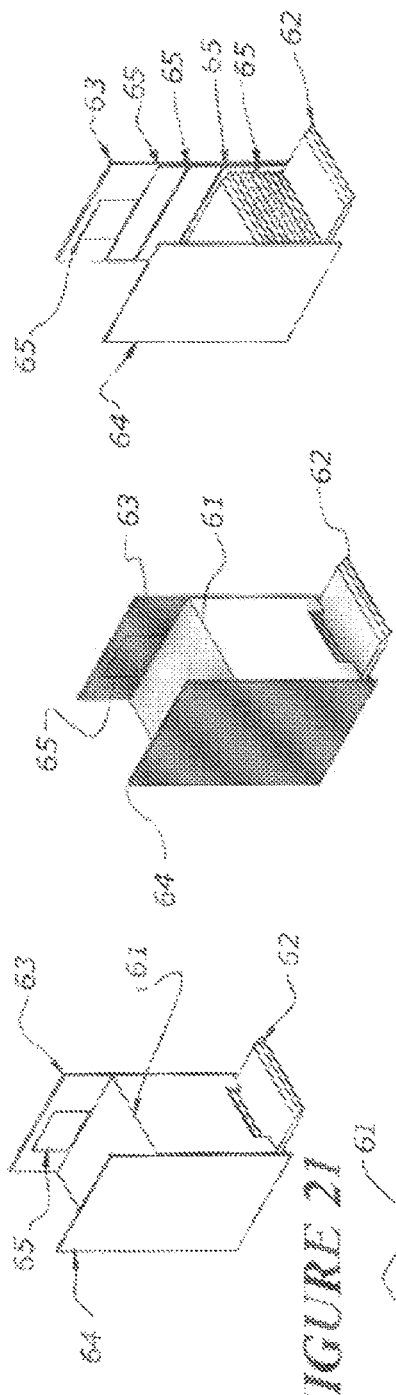
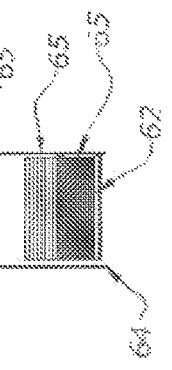
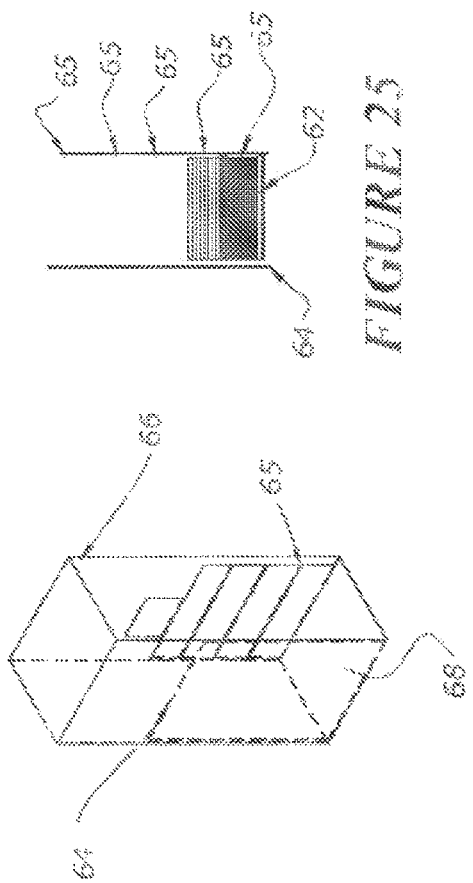
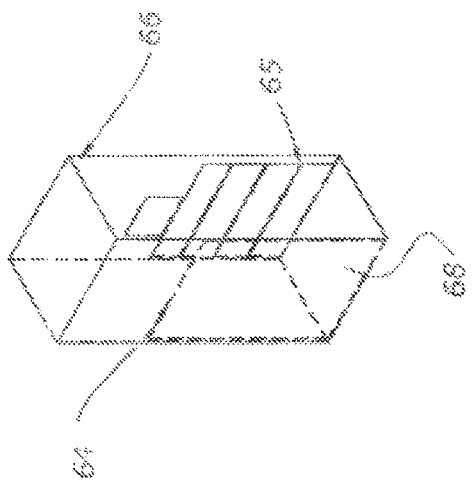
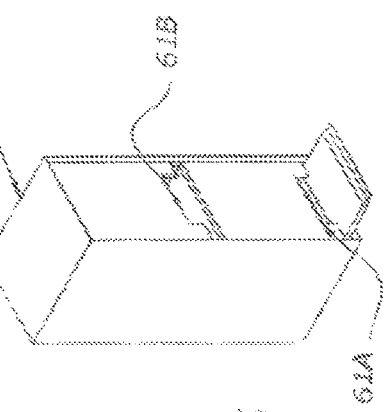
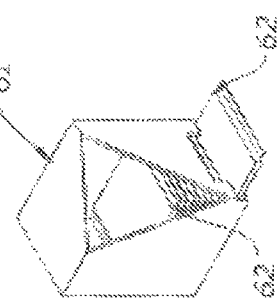
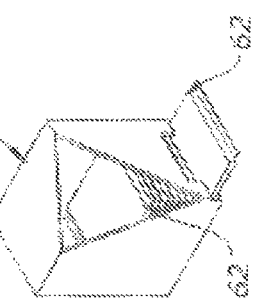
FIGURE 21  FIGURE 22  FIGURE 23  FIGURE 24  FIGURE 25  FIGURE 26  FIGURE 27

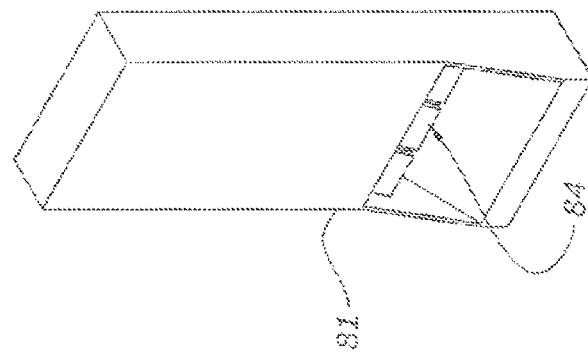
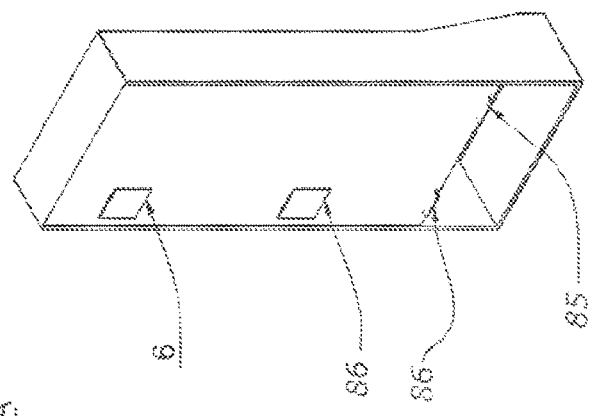
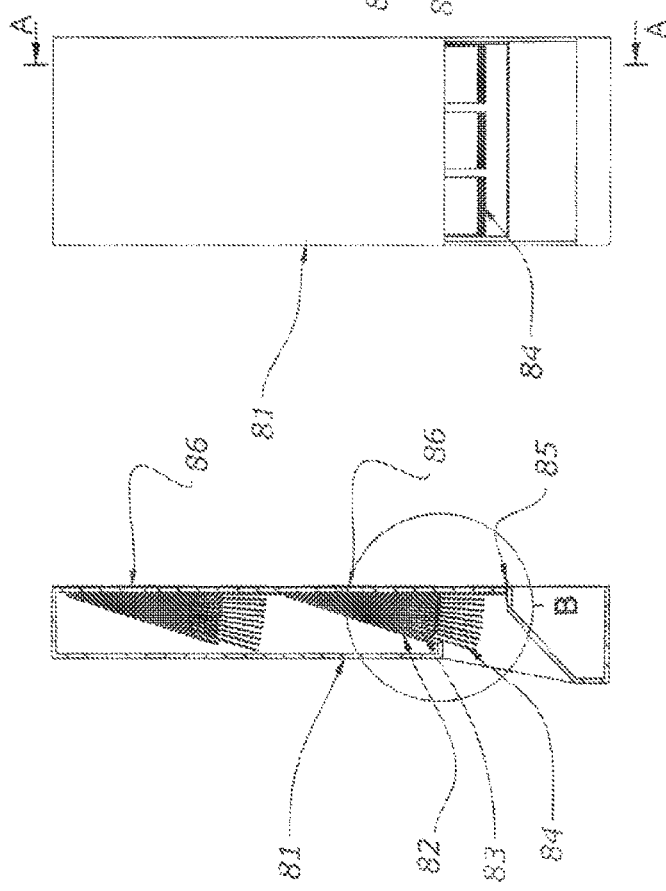
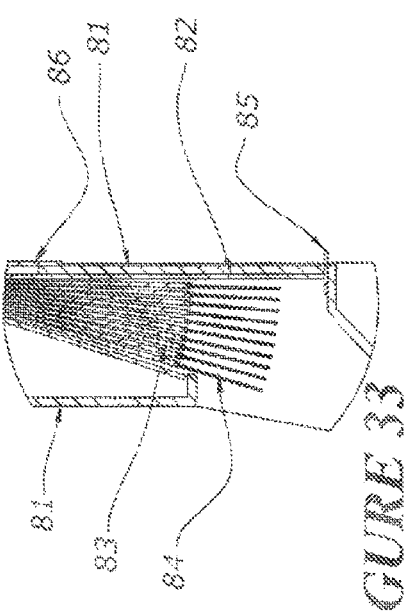

MEDICAL SUPPLIES CABINET

PRIORITY CLAIM TO RELATED APPLICATIONS

This application is a U.S. national stage filing under 35 U.S.C. § 371 from International Application No. PCT/IB2018/057530, filed on 28 Sep. 2018, and published as WO2019/064244 on 4 Apr. 2019, which claims the benefit under 35 U.S.C. 119 to New Zealand Application No. 735981, filed on 29 Sep. 2017, and to New Zealand Application No. 743404, filed on 12 Jun. 2018, the benefit of priority of each of which is claimed herein, and which applications and publication are hereby incorporated herein by reference in their entirety.

FIELD OF THE INVENTION

The present invention relates to a medical supplies cabinet.

BACKGROUND OF THE INVENTION

Medical supplies containers are often found at business premises and provide staff at a business, access to certain medical supplies that may be required during an incident that may require first aid assistance. In a very basic form a medical supplies container may exist in a drawer of a kitchen cabinet. A container may include bandages, plasters, antiseptic cream and potentially tools such as tweezers and scissors. Such containers are often poorly stocked and maintained. If stock hasn't run out, it can still be difficult to find medical supplies within such a container. People responsible for maintaining the first aid container of such kind will often monitor stock levels and may spend additional time attending to the tidiness of the container.

An example of an improved first aid cabinet is described in WO2016/181352. This cabinet provides a substantial improvement over the first aid container as described above.

However, there are still substantial improvements to be made in the function of such a cabinet. Often a restocking of the cabinet may result in the wrong items being located in the wrong location of a cabinet. Since the load cells described in WO2016/181352 are likely to be programmed for sensing specific items such as plasters, for example, the placement of the wrong item such as a bandage on the same load cell can result in incorrect functioning of the system. One solution may be to provide receptacles of a shape that can only receive a correspondingly shaped item. For example, scissors have a particular outline for which a receptacle can be included in the cabinet to be able to snugly receive scissors. However, many medical supplies are of a fairly generic shape or are provided in a box. Therefore, in particular for large receptacles so provided, many other smaller format medical supplies can be incorrectly received. This can result in problematic reading of the stock levels and consumption of medical supplies from the cabinet. In WO2016/181352 the monitoring of consumption and stock levels is done by the use of load cells. However, it has been found that load cells on their own may not give an accurate indication of the interaction with the medical supplies cabinet as items of a particular kind may not all be of a consistent weight. Another disadvantage of load cells is the cost of load cells, particularly due to the additional mechanical design elements needed to isolate the load cells to prevent false readings or other issues.

Accordingly, it is an object of the present invention to provide improvements over existing medical supplies cabinets that addresses the abovementioned disadvantages and/or to at least provide the public with a useful choice.

SUMMARY OF THE INVENTION

In one aspect, the present invention may be said to be a medical supplies cabinet comprising:

a housing presenting a medical supplies storage zone at where there is provided at least one medical supplies receptacle, the receptacle(s) being of a shape and configuration to be able to at least partly receive and hold at least one medical item, a sensor associated with a or each receptacle, the sensor configured to generate a signal indicative of the presence and/or absence or removal of the medical item in/from the receptacle.

In one configuration, there are a plurality of discrete medical supplies receptacles, at least two of said plurality of receptacles being of a shape to receive different said medical items.

In one configuration, there are a plurality of discrete medical supplies receptacles, at least two of said plurality of receptacles being of a shape to receive different said medical items.

In one configuration, a capacitive sensor including a pair of sensing element, is provided for at least one of said receptacles, the capacitive sensor configured to generate a signal indicative of the presence of the medical item within the receptacle.

In one configuration, the capacitive sensor is configured to generate a signal indicative of the presence of the medical item within the receptacle based on at least one of:
  i. the dielectric value and/or change of the dielectric value of the medical item(s) sensed by the capacitive sensor, and/or
  ii. the relative position and/or a change in the relative position of the pair of sensing elements of the capacitive sensor.

In one configuration, a capacitive sensor including a pair of sensing element is provided for at least two of said receptacles.

In one configuration, the at least one medical item is a packaged medical item and preferably a plurality of medical items are provided in the package.

In one configuration, the receptacles are removable from the housing.

In one configuration, the capacitive sensor comprises a pair of sensing elements that are spaced apart from each other.

In one configuration, the pair of sensing elements are planar and are parallel, spaced and non-coplanar to each other a said medical item to be received between the pair.

In one configuration, the pair of sensing elements are planar and are parallel, spaced and coplanar to each other a said medical item to be received across the pair.

In one configuration, the pair of sensing elements are a pair of electrically conductive elements.

In one configuration, the capacitive sensor is configured to sense the addition or removal of a medical item to and from the receptacle.

In one configuration, the signal indicative of the presence of the medical item at a receptacle is proportional to the capacitance value of the capacitive sensor or a change in the capacitance of the capacitive sensor.

In one configuration, addition or removal of a medical item from between the two sensing elements changes the capacitance value of the capacitive sensor by changing the dielectric value of the capacitive sensor.

In one configuration, a change in the relative position of the sensing elements results in a change in capacitance value of the capacitive sensor, the signal generated by the capacitive sensor being proportional to the change in the capacitance value.

In one configuration, the change in capacitance value of the capacitive sensor is proportional to the presence or absence of the medical item at the receptacle.

In one configuration, a least one receptacle is shaped and configured to receive a at least one of a said medical item or a package including a plurality of the medical items, where said item(s) are able to be individually removed from and/or added to the receptacle or package at the receptacle, the sensor being associated with the receptacle and configured to provide a signal indicative of one or more of:
  a) size of package,
  b) number of medical items in the package or number of items in the receptacle,
  c) number of medical items removed from or added to the package,
  d) medical item(s) removed from or added to the receptacle, and
  e) an orientation of item(s) in the receptacle.

In one configuration, a least one receptacle is shaped and configured to receive a plurality of the same medical items or a package including a plurality of the medical items, where said items are able to be individually removed from and/or added to the receptacle or package at the receptacle, the sensor being associated with the receptacle and configured to provide a signal indicative of one or more of:
  a) size of package,
  b) number of medical items in the package or number of items in the receptacle,
  c) number of medical items removed from or added to the package,
  d) number of medical items removed from or added to the receptacle, and
  e) an orientation of items in the receptacle.

In one configuration, the medical supplies cabinet further comprises:
  a door, the door pivotably connected the housing and the door being moveable between an open position corresponding to the medical supplies storage zone being exposed for interaction by a user and a closed position where the door covers the medical supplies storage zone thereby preventing interaction by a user.

In one configuration, the housing includes a camera to make a recording of the view facing away from the medical supplies storage zone of the cabinet, the door includes a mirror that is located to reflect a view of at least part of the medical supplies storage zone to the camera when the door is near its closed position such that the camera can make a recording of the medical supplies storage zone when the door is near its closed position.

In one configuration, a capacitive sensor is associated with the door and configured to generate a signal indicative of the position of the door.

In one configuration, the first sensing element comprises a pair of conductive plates that can be electrically charged and are electrically coupled by an electric field between the two conductive plates.

In one configuration, each conductive plate is connected to an electrical power source such that each conductive plate receives an electrical current to charge each conductive plate.

In one configuration, the capacitive sensor has a greater capacitance value when the second sensing element is in the first position than when the second sensing element is in the second position.

In one configuration, when the second sensing element is in the first position (corresponding to a door closed position), the second sensing element substantially covers the pair of conductive plates thereby increasing an intensity of the electrical field between the two conductive plates thereby increasing the capacitance of the capacitive sensor.

In one configuration, when the second sensing element is in the second position (corresponding to a door closed position), the second sensing element partially covers or does not cover the pair of conductive plates thereby reducing the intensity of the electrical field between the two conductive plates thereby reducing the capacitance of the capacitive sensor.

In one configuration, the first sensing element and the second sensing element are both electrically conductive elements.

In one configuration the first sensing element is electrically active and receives current from an electrical power source, while the second sensing element is electrically inactive and does not receive current, or both the first sensing element and the second sensing element are electrically active and receive current.

In one configuration, the second sensing element comprises a pair of conductive elements and the pair of conductive element receive current from a power source.

In one configuration, the capacitive sensor is associated with a receptacle, the receptacle shaped and configured to hold a plurality of medical supplies in a horizontal of vertical stacked configuration, the capacitive sensor is configured to generate a signal indicative of the number of medical supplies removed from at least one of the receptacle, the total number of medical supplies within the receptacle and a full state or empty state of the receptacle.

In one configuration, each item in a package are each individually packaged in a flexible film wrap.

In one configuration, at least one receptacle of the plurality of receptacles is defined by a pair of parallel, spaced apart vertical walls and at least a base wall, a capacitive sensor disposed on or within the receptacle and, the capacitive sensor comprises a pair of sensing elements, wherein each sensing element is disposed on, adjacent or within one of the vertical walls such that the sensing elements are substantially parallel to each other and spaced apart from each other, wherein the capacitive sensor is configured to generate a signal indicative of the number of medical items located in the receptacle between the pair of sensing elements.

In one configuration, the capacitive sensor is configured to generate a signal indicative of the number and/or change of number of medical items within the receptacle based on a change in the capacitance value of the capacitive sensor caused by a change of a dielectric value of the capacitive sensor due to the introduction or removal of a medical item between the pair of sensing elements.

In one configuration, the pair of sensing elements are two conductive plates, each plate disposed on or within the vertical wall.

In one configuration, the two conductive plates are electrically coupled to a power source and receive current from the power source, the two conductive plates behaving like a capacitor when the two plates are charged.

In one configuration at least one receptacle of the plurality of receptacles is defined by a pair of parallel, spaced apart vertical walls and at least a base wall, a capacitive sensor disposed on, at or adjacent or within the receptacle and, wherein the pair of sensing elements comprises a first sensing element disposed on, at or adjacent or within one vertical wall and a plurality of second sensing elements disposed on, at, adjacent or within an opposing vertical wall.

In one configuration, each of the second sensing elements comprises a surface area that is less than the surface area of the first sensing element.

In one configuration, the first sensing element is a grounded element.

In one configuration, a plurality of the second sensing elements are arranged in an array structure vertically along the vertical wall of the receptacle.

In one configuration, the second sensing elements are of equal dimensions to each other.

In one configuration, the capacitive sensor is configured to generate a signal indicative of the number of packs containing medical supplies within the receptacle and the number of medical supplies within each pack of medical supplies.

In one configuration, the capacitive sensor is configured to generate a signal indicative of a pack containing at least one medical item or individual medical items being removed from the pack.

In one configuration, the signal is proportional to or based on a capacitance value or a change of capacitance value of the capacitive sensor, wherein the capacitance value or change in capacitance value is proportional or based on the dielectric value or change in dielectric value, and wherein the number of packs and/or the number of medical items within each pack affects the dielectric value of the capacitive sensor.

In one configuration, the optical sensing arrangement comprises a light emitter and a light detector, the light emitter configured to emit a light and the light detector configured to detect a light, the optical sensing arrangement configured to generate a signal indicative of the identity or number of medical items or state of a medical item within a receptacle, based on the light detected by the light detector.

In one configuration, each receptacle comprises a plurality of optical sensing arrangements associated with each receptacle.

In one configuration, the optical sensing arrangement comprises one or more light emitters and one or more colour detectors, the colour detectors configured to detect a colour on a portion of an item within the receptacle (or introduced into the receptacle), and the optical sensing arrangement configured to generate a signal indicative of an identity of the item within the receptacle.

In one configuration the optical sensing arrangement comprises a plurality of light emitters, each light emitter configured to emit a single colour (or frequency or wavelength) light.

In another configuration the optical sensing arrangement comprises one or more light guides, each light guide including a first end opening and a second end opening, the light guide arranged such that the first end opening is located adjacent the one or more light emitters and second end opening is inserted into or arranged adjacent a receptacle to guide light into the receptacle, a light detector arranged adjacent the second end opening, the light detector configured to detect a colour of light reflected from a medical item within the receptacle or detect an intensity of light.

In one configuration, the optical sensing arrangement configured to generate a signal indicative of the type of medical item or the number of medical items within the receptacle.

In one configuration, at least one of the plurality of optical sensing arrangements is/are configured to generate a signal indicative of the identity of a medical item or the state of a medical item within the receptacle based on one or more colours detected on the medical item.

In one configuration, at least one of the plurality of optical sensing arrangements is/are configured to generate a signal indicative of the number of medical items based on an intensity of light and/or an intensity at specified locations within the receptacle.

In one configuration, the optical sensing arrangement comprises a plurality of light sensors capable of detecting the intensity of light, the plurality of light sensors being associated with or embedded within a receptacle, the light sensors being arranged spaced apart from each other, the optical sensing arrangement configured to generate a signal indicative of a number of medical items or an arrangement of medical items or an orientation of medical items within the receptacle, the signal based on the difference in intensity of light detected at each light sensor of the plurality of light sensors.

In one configuration, the sensor is able to sense between at least one of
  a. the presence and absence of an item at the receptacle,
  b. the presence of the correct item and incorrect item at the receptacle, and
  c. the correct orientation and incorrect orientation an item of pack containing a plurality of said items at the receptacle.

In one configuration, the sensor is able to sense data carried buy or associated with the item at the receptacle such as expiry date data.

In one configuration, an optical sensing arrangement associated with the at least one receptacle of the medical supplies cabinet, the optical sensing arrangement configured to generate a signal indicative of an identity or number of medical items within a receptacle or the state of a medical item within a receptacle.

In one configuration, the sensor is a load sensors configured to generate a signal indicative of a medical item being removed from the receptacle by an application of a force.

In one configuration, the magnitude of force detected by the one or more load sensors corresponds to the number of items removed from the receptacle.

In one configuration, the number of discrete forces above a predefined threshold corresponds to the number of items removed from the receptacle.

In one configuration, one or more capacitive sensors or one or more optical sensors or one of more EID sensors associated with a receptacle, the one or more capacitive sensors configured to generate a signal indicative of the number of items in the receptacle, and the one or more optical or EID tag sensors configured to generate a signal indicative of the type of items or number of items or arrangement of the item or items at the receptacle.

In one configuration, a processor to receive information form the sensor, configured to determine one or more of:
  i. The number of total items in a receptacle,
  ii. The types of item in a receptacle,
  iii. The number of items added to a receptacle, iv. The number of items removed from a receptacle v. The orientation of one of more items in a receptacle.

In one configuration the medical supplies cabinet further comprises one or more environmental sensors disposed on or presented on the medical supplies cabinet, the one or more environmental sensors configured to generate a signal indicative of an environmental condition.

In one configuration, the environmental sensors are at least one of a humidity sensor, a temperature sensor or a gas sensor.

In one configuration, the medical supplies cabinet comprises one or more cameras positioned on or within the medical supplies cabinet, wherein the one or more cameras being activated when a door of the medical supplies cabinet is opened.

In one configuration the medical supplies cabinet comprises a plurality of lights presented on the door, the plurality of lights being coloured a specific colour that indicates a state of the medical supplies cabinet.

In one configuration, the medical supplies cabinet comprises a processor and a memory unit, the processor in electronic communication with one or more of the sensors of the medical supplies cabinet and configured to process the signals received from the one or more sensors.

In one configuration, the medical item or medical supplies or medical product is any one or more of an eye pad, a gel pad, a plaster or multiple plaster pack, wipes, resuscitation kit, painkiller tablet boxes, tablet boxes scissors, bandage rolls or a box of gloves.

In one configuration, the eye pad is packaged in an individually wrapped format.

In one configuration, the wrap is a plastic disposable wrap.

In one configuration, the wrapped eyepad is held in its dedicated receptacle in a (preferably vertically) stacked format with like wrapped eyepads.

In one configuration, the wipes are packaged in disposable box.

In one configuration, the box is a paperboard based box.

In one configuration, a plurality of packaged or wrapped medical items can be received and retained at a receptacle, preferably in a stacked condition.

In one configuration, the cabinet is able to be wall mounted.

In one configuration, the cabinet is able to be plinth mounted.

In one configuration, at least some and preferably all medical supplies retained by the cabinet are able to be removed from the cabinet without needing to pass any cabinet security to gain access to the medical supplies.

In one configuration, the doors of the cabinet are not locked doors.

In one configuration, the doors of the cabinet are not lockable doors.

In one configuration, the sensor is an EID sensor able to sense the presence of an EID tag attached with the medical item.

In one configuration, the sensor is an EID sensor able to sense the presence of an EID tag attached directly to the medical item or to a pack that contains at least one said medical items.

In one configuration, the sensor is an RFID sensor.

In one configuration, the RFID sensor includes an antenna for sensing the presence of an RFID tag in proximity.

In one configuration, the RFID sensor includes a reader coupled to said antenna.

In one configuration, the cabinet comprises a plurality of antenna coupled to said reader.

In one configuration, antenna located remotely to the cabinet are provided able to wireless communicate with the reader and/or processor of the cabinet.

In one configuration, the sensor is able to sense a plurality of EID tags.

In one configuration, the sensor is able to sense the location of an RFID tag in the cabinet.

In one configuration, the sensor is able to read the orientation of a package carrying an RFID tag in the cabinet.

In one configuration, the sensor is at least one an RFID sensor that and includes an antenna for sensing the presence of an RFID tag in proximity and is configured to read the orientation of a package carrying an RFID tag at least when at a receptacle.

In one configuration, the reader includes or is coupled to a processor.

In one configuration, the cabinet electrical power needs are met by mains power and in case of mains power failure by an integrated uninterruptable power supply.

In one configuration, the uninterruptable power supply is able to reduce or terminate supply of electrical power to power demanding components of the cabinet in order of importance of the components and/or if any require power at any given time.

In one configuration, the cabinet carries a door that is able to be closed to prevent a person accessing medical items, the uninterruptable power supply is able to reduce or terminate supply of electrical power to the sensor(s) when the door of the cabinet is closed.

In one configuration, the or each receptacle is of a shape and configuration to encourage a user to put only a medical item or pack containing at least one of said medical items in the receptacle by a matching of the same and configuration of the receptacle to the shape and configuration of the item or pack containing at least on said item.

In one configuration, the relationship between the shape and configuration of the receptacle and the medical item or pack is a go-no go relationship.

In a further aspect the present invention may be said to be a medical supplies system that comprises:
  a. medical items of at least two different kinds and with which two differently configured EID tags are associated, and
  b. a cabinet comprising:
  a housing presenting a medical supplies storage zone at where there is provided at least two medical supplies receptacles, one for each kind of medical item to be received at a respective receptacle,
  an EID tag reader to read the EID tags and arranged and configured to determine at least one of the following:
  (a) if the correct medical item is located at its respective receptacle,
  (b) the orientation of the medical item when in a respective receptacle, and
  (c) information carried by the EID tag.

In yet a further aspect, the present invention may be said to be a medical supplies cabinet comprising:
  a housing presenting a medical supplies storage zone at where there is provided at a plurality of medical supplies receptacles, the receptacles being of a shape and configuration each to be able to at least partly receive and hold at least medical items contained in at least two different shaped disposable packages, each package including a colour, different to each other, on at least part of its surface, each receptacle defining a mouth opening matching the shape of a respective package and via which said package can be hence received into the receptacle in a snug manner, at least part of each receptacle and/or a region about the mouth opening being of a colour that substantially matches the colour of said package to be received at it, to encourage a said package to be loaded into a matching receptacle.

In one configuration, the receptacles are of a shape and configuration each to be able to at least partly receive and hold said medical items each contained in at least two different shaped disposable packages, each package carrying a said EID tag.

In one configuration, each receptacle defines a mouth opening matching the shape of a respective package and via which said package can be hence received into the receptacle in a snug manner to encourage a said package to be loaded into a matching receptacle.

In a further aspect, the present invention resides in a medical supplies cabinet comprising:

a housing presenting a medical supplies storage zone at where there is provided a plurality of discrete medical supplies receptacles, the receptacles being of a shape and configuration to be able to at least partly receive and hold at least one (preferably packaged) medical item, an optical sensing arrangement associated with at least one receptacle of the medical supplies cabinet, the optical sensing arrangement configured to generate a signal indicative of an identity or number of medical items within a receptacle or the state of a medical item within a receptacle.

In one configuration, the optical sensing arrangement is able to sense colour and/or shape.

In one configuration, the optical sensing arrangement is a code scanner.

In one configuration, the optical sensing arrangement is a bar code scanner or the like.

In still a further aspect, the present invention may be said to be a medical supplies dispenser comprising:

a housing presenting a medical supplies storage zone at where there is provided a at least one receptacle, the receptacle being of a shape and configuration to be able to at least partly receive and hold at least one medical item, a load sensor associated with the receptacle and to be associated with the at least one medical item, the load sensor configured to generate a signal indicative of a medical item being removed from the receptacle by an application of a force.

In one configuration, the magnitude of force detected by the sensor corresponds to the number of items removed from the receptacle.

In one configuration, the signal from the load sensor is able to be communication to the medical supplies cabinet as herein described or to a process that also is able to receive a signal from the sensor of the medical supplies cabinet as herein described.

In yet a further aspect, the present invention may be said to be a medical supplies cabinet comprising at least one receptacle to receive a medical item or pack containing a plurality of medical items the medical item or pack received in the vicinity of a capacitive sensor of the cabinet and able vary the capacitance of the sensor based on the location of the medical item or pack or items of the pack relative to the capacitive sensor.

In a further aspect, the present invention may be said to be a system comprising a medical supplies dispenser as herein before described and a medical supplies cabinet as herein before described.

In still a further aspect, the present invention may be said to be a medical supplies cabinet comprising:

a housing presenting a medical supplies storage zone at where there is provided at least one medical supplies receptacles, the receptacle(s) being of a shape and configuration each to be able to at least partly receive and hold at least one medical item, a door, the door pivotably connected the housing and the door being moveable between an open position corresponding to the medical supplies storage zone being exposed for interaction by a user and a closed position where the door covers the medical supplies storage zone thereby preventing interaction by a user, a camera to make a recording of the view facing away from the medical supplies storage zone of the cabinet, the door includes a mirror that is located to reflect a view of at least part of the medical supplies storage zone to the camera when the door is near its closed position such that the camera can make a recording of the medical supplies storage zone when the door is near its closed position.

In one configuration, the camera is located by the housing.

In one configuration, there is only one door provided to prevent access to the storage zone when the door is closed.

In one configuration, there is only one camera provided to record the view facing away from the medical supplies cabinet.

In a further aspect, the present invention resides in a medical supplies cabinet comprising:

a housing presenting a medical supplies storage zone at where there is provided a plurality of discrete medical supplies receptacles, the receptacles being of a shape and configuration to be able to at least partly receive and hold at least one (preferably packaged) medical item, one or more environmental sensors disposed on or presented on the medical supplies cabinet, the one or more environmental sensors configured to generate a signal indicative of an environmental condition.

In a further aspect, the present invention resides in a medical supplies cabinet that comprises a housing that presents a plurality of discrete receptacles to each receive at least one medical item, at least one of the receptacles is of a shape that corresponds to the shape of at least one medical item in a manner so that the at least one medical item is able to be held at the receptacle in a snug fit manner.

In still a further aspect the present invention may be said to be a method of reporting stock levels at a receptacle (or receptacles) of a medical supplies cabinet at where at least one packaged medical item is retained, the method comprising the steps of:

receiving a signal from a sensor associated with the receptacle, processing the received signal to determine the presence or absence or introduction/removal of a packaged medical item from the receptacle; wherein the presence or absence or introduction/removal of a packaged medical item from the receptacle is based on a sensible characteristic or ID of or associated with the packed medical item.

In one configuration, the sensible characteristic is of the weight of the packaged medical item.

In one configuration, the signal is from a capacitive sensor associated with the receptacle, the capacitive sensor comprising a pair of sensing elements, wherein said processing of the received signal to determine the presence or absence or introduction/removal of a medical item from the receptacle is based on identifying at least one of:

i. a dielectric value and/or change in the dielectric value of the capacitive sensor as a result of the presence or movement or absence of the medical item relative to the sensor, and ii. the relative position and/or change in the relative position of the pair of sensing elements of the capacitive sensor.

In one configuration, the method further comprises identifying an event based on the gradient or change in gradient of an output signal from the capacitive sensor.

In one configuration, the sensor is an optical sensor and the method further comprises:

receiving a signal from the optical sensor associated with the receptacle, the optical sensor including at least a light emitter and a light detector, processing the received signal to determine an identity of a medical item or the number of medical items within a receptacle, wherein the identity of a medical item is determined based on a detected colour of the medical item and the number of medical items determined based on an intensity of light detected within the receptacle.

In one configuration, the optical sensor comprises a plurality of light sensors disposed in the receptacle and spaced apart from each other, the method comprises receiving a signal from each of the light sensors and processing the received signals to determine either a number of items or configuration/arrangement of items within the receptacle based on an intensity of light and/or an intensity at specified locations within the receptacle.

In one configuration, the sensible characteristic is of the presence or absence of an EID tag associated with the medical item when in the proximity of a said sensor that is an EID sensor.

In a further aspect, the present invention resides in a method of reporting stock levels at a receptacle (or receptacles) of a medical supplies cabinet at where at least one packaged medical item is retained, the method comprising the steps of:

receiving a signal from an optical sensor associated with a receptacle, the optical sensor including a light emitter and a light detector, processing the received signal to determine either a presence of a medical item in the receptacle or an identity of an item or a number of items in the receptacle based on identifying at least one of:

i. a colour of the item in the receptacle, ii. the intensity of light within the receptacle, iii. intensity at specified locations within the receptacle.

In a further aspect, the present invention resides in a method of reporting stock levels at a receptacle (or receptacles) of a medical supplies cabinet at where at least one packaged medical item is retained, the method comprising the steps of:

receiving a signal from a load sensor associated with a receptacle, processing the received signal to determine removal of a single medical item from the receptacle based on identifying a force detected by the load sensor, comparing the detected force with a threshold and if the force exceeds a threshold, indicating a single item has been removed.

In one configuration, the medical supplies cabinet is of a kind as herein described.

In a further aspect, the present invention resides in a medical supplies cabinet comprising:

a housing presenting a medical supplies storage zone at where there is provided a plurality of discrete medical supplies receptacles, the receptacles being of a shape and configuration to be able to at least partly receive and hold at least one (preferably packaged) medical item, an optical sensing arrangement associated with at least one receptacle of the medical supplies cabinet, the optical sensing arrangement configured to generate a signal indicative of an identity or number of medical items within a receptacle or the state of a medical item within a receptacle; and one or more load sensors associated with a receptacle, each load sensor configured to generate a signal indicative of a medical item being removed from the receptacle by an application of a force wherein the magnitude of force detected by the one or more load sensors corresponds to the number of items removed from the receptacle.

In one configuration, the medical supplies cabinet may further comprise one or more environmental sensors disposed on or presented on the medical supplies cabinet, the one or more environmental sensors configured to generate a signal indicative of an environmental condition.

In a further aspect, the present invention resides in a medical supplies cabinet comprising a housing presenting a medical supplies storage zone at where there is provided a plurality of discrete medical supplies receptacles, the receptacles being of a shape and configuration to be able to at least partly receive and hold at least one (preferably packaged) medical item, one or more load sensors associated with a receptacle, each load sensor configured to generate a signal indicative of a medical item being removed from the receptacle by an application of a force wherein the magnitude of force detected by the one or more load sensors corresponds to the number of items removed from the receptacle; and one or more environmental sensors disposed on or presented on the medical supplies cabinet, the one or more environmental sensors configured to generate a signal indicative of an environmental condition.

In still a further aspect the present invention resides in a medical supplies cabinet comprising a plurality of receptacles able to each receive at least one packaged medical item a or the receptacle(s) including an openable closure to allow and prevent loading of the packaged medical item into the receptacle, a sensor part of the cabinet by which a sensible feature of the packaged medical item can be sensed, the sensor in operative connection with the openable closure to allow the closure open to be opened if the sensed feature of the packaged medical item is verified suitable for receipt at the receptacle.

In one configuration, the sensed feature related to the expiry date for the packaged medical item.

In one configuration, the sensed feature is an RFID tag of the packaged medical item.

In one configuration, the sensed feature is a bar code of the packaged medical item.

In one configuration, the sensor is a bar code scanner.

In one configuration, the sensor is an EID sensor.

In one configuration, a light at a receptacle is provided that can illuminate or change colour once a verified item is sensed by the sensor to indicate which receptacle the item is to be loaded.

In one configuration, the cabinet includes a speaker that is able to play audio to inform a person that has presented a package for loading into the cabinet that the package is verified by the system of the present invention loading into a receptacle of the cabinet.

In one configuration, the cabinet includes a visual communication means that is able to inform a person that has presented a package for loading into the cabinet that the package is verified by the system of the present invention loading into a receptacle of the cabinet.

In one configuration, a light is provided to illuminate adjacent or at least part of a receptacle to indicate to a user which receptacle a package should be loaded into.

In one configuration, at least one medical supply unit is provided remote from the cabinet and is able to wirelessly communicate with the cabinet.

In one configuration, the RFID sensor can is positioned in the cabinet to be able to help detect the orientation and/or location of an RFID carrying package in a receptacle of the cabinet.

In one configuration, the medical supplies receptacles are removable from the housing and able to be removably secured to the cabinet, the housing including a plurality of receptacle receiving regions, each region able to receive at least two different shaped and configured receptacles.

In a further aspect, the present invention resides in a medical supplies cabinet comprising:

a housing presenting a medical supplies storage zone at where there is provided at least one medical supplies receptacle, the receptacle being of a shape and configuration to be able to at least partly receive and hold a package containing at least one medical item, wherein the receptacle is adapted to encourage the loading only of packages of a kind of said package by a person, by virtue of at least one of:
(a) the receptacle being of a shape and configuration to ensure a snug fit in said receptacle by said package,
(b) an indicium or indicia at or proximate the receptacle, presented to the person for comparison to indicium or indicia on the package, and
(c) an EID tag reader of the cabinet in proximity to the receptacle to detect or read a strength of a signal from an EID tag carried by said package, and a response is provided based on the strength of the signal.

In one configuration, the EID tag reader is or comprises at least one reader antenna that is configured to read the strength of the signal from an EID tag.

In one configuration, the EID tag reader is a RFID tag reader and the EID tag is the RFID tag.

In one configuration, the indicium or indicia is a colour(s).

In a further aspect, the invention resides in a medical supplies cabinet comprising:

a housing presenting a medical supplies storage zone at where there is provided at least one medical supplies receptacle, the receptacle(s) being of a shape and configuration to be able to at least partly receive and hold at least one medical item, at least one tag reader at or proximate the receptacle(s), and at least one sensor tag configured to generate a signal or information that be configured to be read by the at least one tag reader, wherein, said at least one sensor tag is located on the or each medical item or a packaging of each medical item in such a position that damaging or tampering of the medical item or packaging causes said sensor tag(s) to be damaged or removed from that medical item or packaging, and wherein, a response is sent based on the reading from the at least one tag reader, thereby enabling determination of damage to or tampering of any medical item or the packaging.

In one configuration, the at least one sensor tag is an EID tag and at least one tag reader is an EID tag reader.

In one configuration, the at least one sensor tag is a RFID tag and at least one tag reader a RFID tag reader or a reader antenna.

In a further aspect, the invention resides in a medical supplies cabinet comprising:

a housing presenting a medical supplies storage zone at where there is provided at least one medical supplies receptacle, the receptacle(s) being of a shape and configuration to be able to at least partly receive and hold at least two medical items, at least one tag reader at or proximate the receptacle(s), and at least two sensor tags that are carried by each medical item or a packaging of each medical item, each tag being configured to generate a signal or information to be read by the at least one tag reader, wherein, said at least two sensor tags are located each medical item or a packaging of each medical item in such an orientation that when the at least two medical items are received in one receptacle and/or are proximate to each other, the at least one tag reader can read signal or information generated by at least one tag carried by each medical item.

In one configuration, the sensor tags are EID tags and at least one tag reader is an EID reader.

In one configuration, the sensor tags are RFID tag and at least one tag reader is a RFID reader or a reader antenna.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The entire disclosures of all applications, patents and publications, cited above and below, if any, are hereby incorporated by reference.

BRIEF DESCRIPTION OF THE DRAWINGS

Preferred aspects of the present invention will now be described with reference to the accompanying drawings in which.

FIG. 4B shows an internal configuration of a metal plate on a door arm relative to a fixed plate in the cabinet.

FIG. 5B shows an internal configuration of a metal plate on a door arm relative to a fixed plate in the cabinet.

FIGS. 6A and 6B show two views of the medical supplies cabinet with the door in a completely open position. FIG. 6B shows an internal configuration of a metal plate on a door arm relative to a fixed plate in the cabinet.

FIG. 7 shows a view of two fixed plates that are associated with a wall of the cabinet denoting a door open condition.

FIG. 8 shows the presence of the plate attached to the door arm adjacent with fixed plates of FIG. 8, denoting a door closed position.

FIGS. 16 and 17 show the moving metal plate 35 may move between a bin full position and bin empty position as it moves relative to the first and second capacitive plates 37 and 38.

FIGS. 17A and 17B show the arrangement of a biasing member and a portion of a capacitive sensor associated with the door, wherein the door is shown in an open and closed configuration respectively.

FIGS. 21 to 27 shows a configuration of capacitive sensors associated with a receptacle to detect use of individual medical items from a stack of medical items.

FIGS. 29 to 33 show a configuration of load sensors and optional capacitive sensors in a receptacle to detect removal of a medical item by application of a force.

DETAILED DESCRIPTION

In the following detailed description, reference is made to the accompanying figures, which form a part hereof. The illustrative embodiments described in the detailed description and figures are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Various examples of the preferred embodiments of the medical supplies cabinet and the components thereof will now be described with reference to the accompanying drawings.

Figure 1:
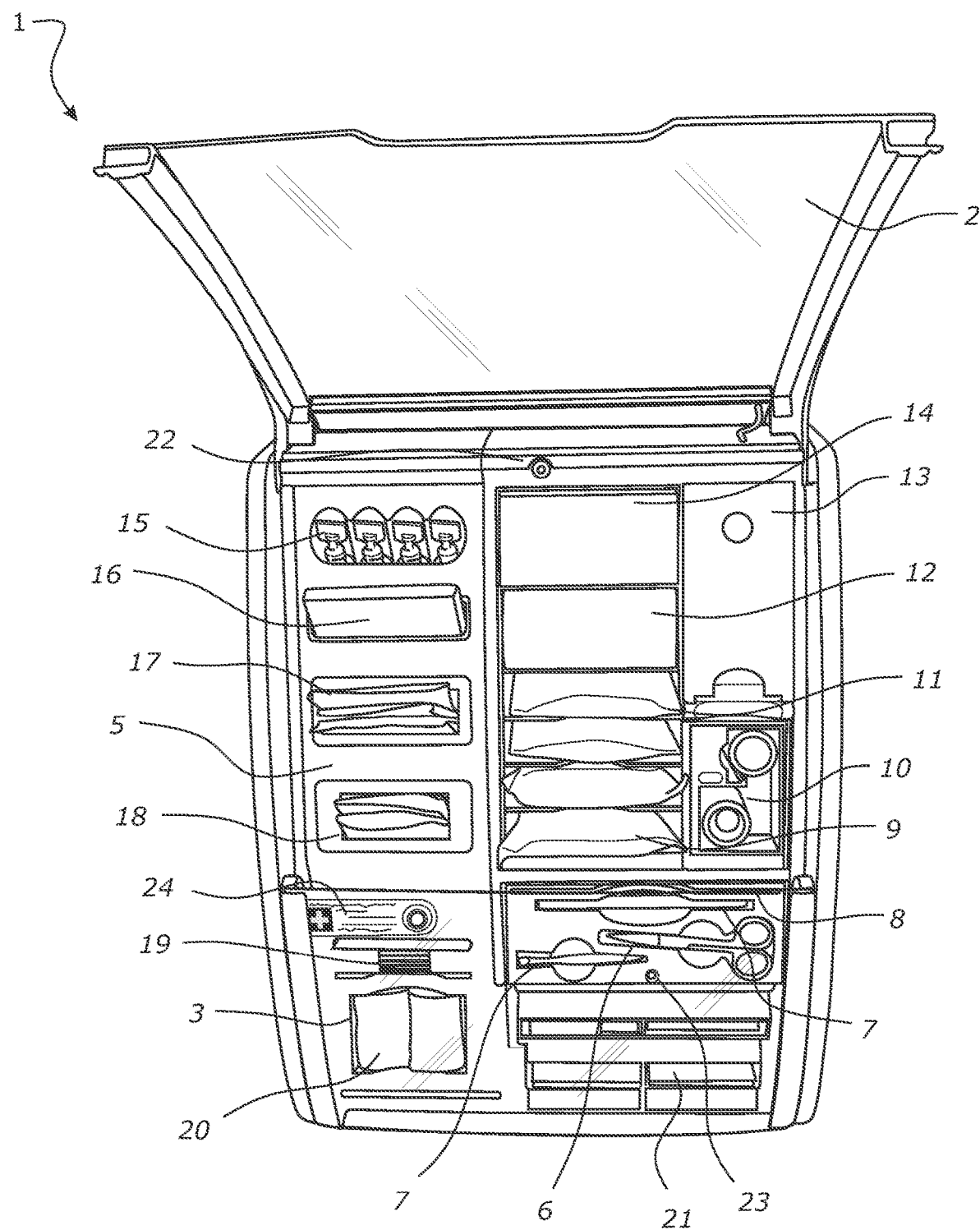
FIG. 1 is a front view of a medical supplies cabinet according to one preferred embodiment of the invention having an upper front door and a lower front door, with the upper front door shown in an open condition.

In FIG. 1, there is shown one example of a preferred embodiment of a medical supplies cabinet 1 where the front face of the cabinet is provided with a first door 2 and a second door 3, the first door 2 is shown in an open condition (also shown in FIG. 2) and the second door 3 is shown in a closed condition (also shown in FIG. 3), covering the medical supplies adjacent. In the preferred form, the doors 2 and 3 are transparent or translucent. There may be two such doors provided, an upper door 2 and a lower door 3. The doors may instead be side by side. Alternatively, only one door may be provided such as the one as will be described later with reference to FIG. 3A. The doors provide the function of keeping dust and other contaminants away from the medical supplies held by the cabinet. The door or doors may also perform the function of indicating cabinet status, as will hereinafter be described. The door(s) position may also control other parts of the cabinet such as the turning on and off of the camera recording function and/or power saving setting to reduce power consumption when for example the door(s) is/are shut.

The cabinet is preferably able to be wall mounted and has a back face 4 and a front face 5. Alternatively, the cabinet may be ground supported or may be supported on a table or plinth or the like. In the most preferred form the cabinet will be wall mounted.

Preferably at the front face 5 there is provided a zone at where a plurality of medical supplies receptacles are presented. For example, a scissor receptacle 6 is provided at where a scissors can be located. A receptacle 7 may be provided for tweezers. Likewise, receptacles may be provided for swabs 7, a manual or instructions 8, bandages 9, tape 10, burn gel 11, 4 in 1 blood stopper package 12, wound cleaner containing pack 13, a resuscitation kit pack 14, eye and wound wash packs 15, emergency blanket containing pack 16, eye pad packs 17, large dressing packs 18, burn gel packs 19 and further 4 in 1 blood stopper packs 20 and plaster containing packs 21. The items to be used with the cabinet are not limited to these.

Each receptacle is preferably of a shape and configuration to be able to receive one or a plurality of such items, in some configurations, contained in packs or wraps. In some receptacles only one pack is received, the pack containing one or more medical supply items that may also be individually wrapped or not. In other forms the receptacles may receive a plurality of discrete packs or wraps containing such items as eye pads 17.

There are one or more of the receptacles configured to receive at least one medical item. At least one or more of the receptacles is of a shape that corresponds to the shape of at least one medical item in a manner so that at least one medical item is able to be held in the receptacle in a snug fit manner. At least one of the receptacles is shaped such that a snug fit exists between the item or package containing the item or a plurality of items or plurality of packages containing the items.

At least one receptacle may be of a shape that corresponds to a specific medical item or a package containing a plurality of medical items so that only those specific medical items or packages can be inserted into the receptacle. Medical items or packages that do not correspond to the shape of the receptacle would not be able to be inserted into the receptacle. The items for each receptacle are preferably identical items. The shape of the receptacles is one way to help prevent mixing of items within receptacles, because only items matching the shape can be inserted in the receptacle. The shape of the receptacle can help in achieving a homogenous distribution of items in certain receptacles. Other receptacles may be of a more general shape and can accept any medical item or package regardless of the shape of the receptacle.

In addition, provided preferably at the front face of the medical supplies cabinet 1, is a camera 22. It is preferably provided at the top of the cabinet. Preferably there is only one camera. This camera may be provided external of the upper door 2 or internal thereof when closed and only become exposed when the top door is open.

A bottom door camera 23 may also be provided. This may be obscured at least partially by the bottom door when the bottom door is in its closed condition. The camera(s) 23,23 may run continuously to record activity in front of the medical supplies cabinet. Alternatively, the cameras 22,23 may record intermittently and may for example only record activity in front of the medical supplies cabinet 1 when one or both or a respective door is at least partially opened. The footage recorded may be transmitted to a local or remote storage device for subsequent and future review. The cameras 22, 23 may so take footage or a photo or photos or all.

An alert button 24 may also be provided by the medical supplies cabinet 1, preferably at the front face of the cabinet. The use(s) of alert button 24 is described later in the specification.

Figure 3:
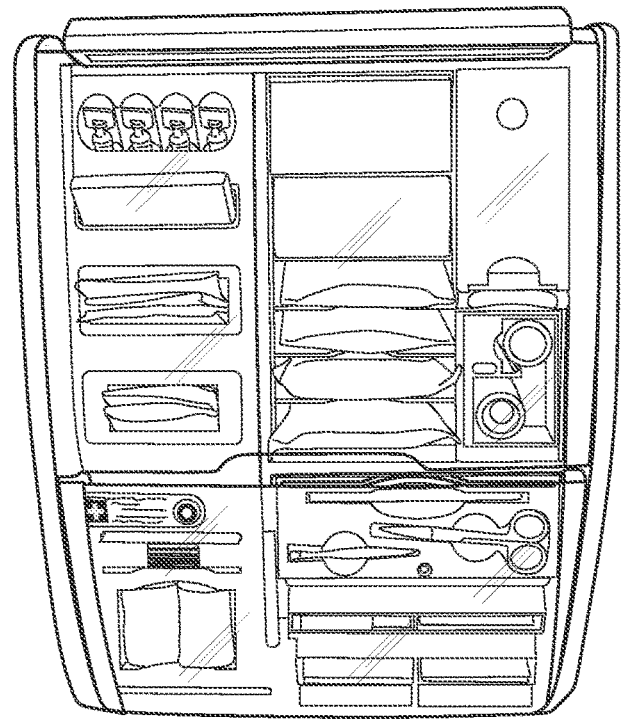
FIG. 3 shows the medical supplies cabinet of FIG. 1 with both doors in a closed condition.
Figure 3A:
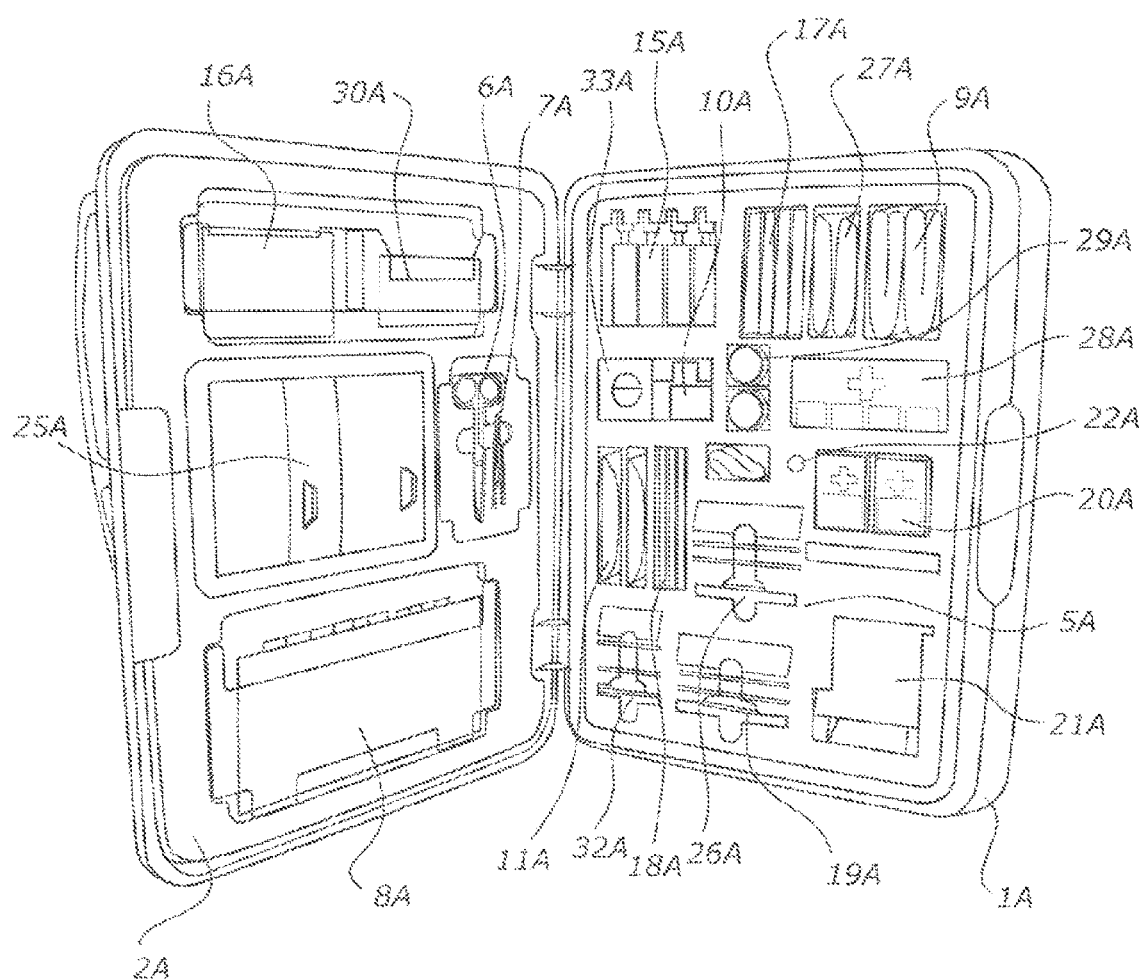
FIG. 3A is a front view of a medical supplies cabinet according to a further preferred embodiment of the invention having only one door, with the door shown in an open condition.

In FIG. 3A, there is shown a further example of a preferred embodiment of a medical supplies cabinet. In this example, the front face of the cabinet 1A is provided with only one door 2.

As shown, on the door side, there is provided a plurality of medical supplies receptacles. For example, a scissor receptacle is provided where a scissors 6 can be located. A receptacle may be provided for tweezers 7. Likewise, receptacles may be provided for emergency blanket containing pack 1, pad 6, biological disposable bag 30. A mirror 25A is also provided in the door side.

Similarly, on the front face of the cabinet 1A, there are receptacles for a bandage 9A (which may be a triangular bandage), tape 10A, large burn dressing or burn gel 11A, large blood stopper such as 4 in 1 blood stopper package 12A, eyewash or wound wash packs 15A, eye pad packs 17A, large dressing packs 18A, burn gel sachets/packs 19A, a small blood stopper packs or a further blood stopper packs 20A, plaster containing packs 21A, hand sanitiser packs 26A, gloves 27A, breathing mask packs 28A and crepe bandage packs 29A. The supplies that could be contained by the receptacles are not limiting to these medical items.

There is also preferably a tape door covering 33A to cover any spare tape(s).

Figure 2:
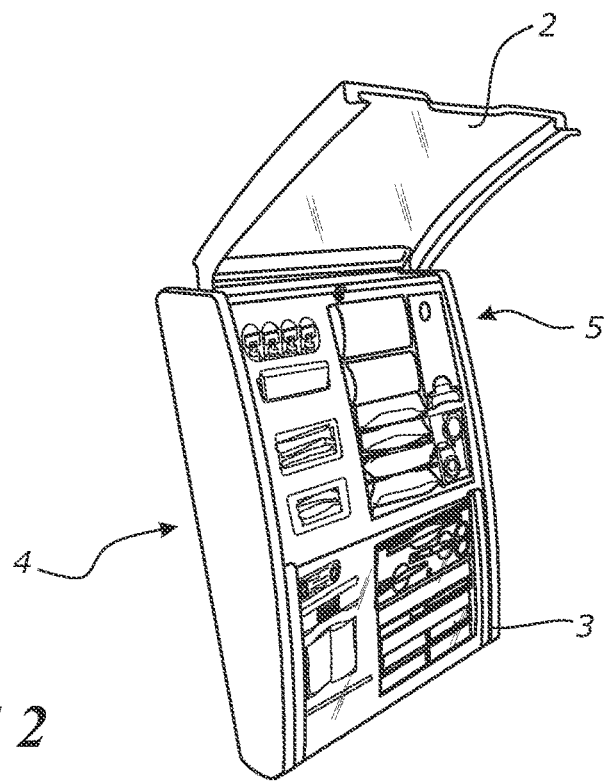
FIG. 2 is a side perspective view of FIG. 1.

Therefore, it can be seen that unlike the first preferred embodiment of the cabinet 1A shown in FIGS. 1-3 where the receptacles are present only on the front face 5, in the second preferred embodiment of the cabinet 1A, the receptacles are present on both the door side as well as the on the front face 5 of the cabinet 1A.

The door 2 is connected by a hinge or other suitable mechanism located on the front face 5A of the cabinet 1A so that the door can be opened thereby revealing the front face 5A or closed thereby concealing the front face 5A.

Each receptacle is preferably of a shape and configuration to be able to receive one or a plurality of such items, in some configurations, contained in packs or wraps. In some receptacles only one pack is received, the pack containing one or more medical supply items. In other forms the receptacles may receive a plurality of discrete packs or wraps containing such items as eye pads 17.

The receptacles are preferably of a shape that corresponds to the shape of at least one medical item in a manner so that at least one medical item is able to be held in the receptacle in a snug fit manner. At least one of the receptacles are preferably shaped such that a snug fit exists between the item or package containing the item or a plurality of items or plurality of packages containing the items.

Similar cabinet 1, at least one receptacle of cabinet 1A may be of a shape that correspond to a specific medical item or a package containing a plurality of medical items so that only those specific medical items or packages can be inserted into the receptacle. Medical items or packages that do not correspond to the shape of the receptacle would not be able to be inserted into the receptacle. The items in each receptacle (i.e. bin or receptacle) are preferably identical items. The shape of the receptacles is one way to prevent mixing of items within receptacles, because only items matching the shape can be inserted in the receptacle. The shape of the receptacle can help in achieving a homogenous distribution of items in certain receptacles. Other receptacles may be of a more general shape and can accept any medical item or package regardless of the shape of the receptacle.

In addition, provided preferably at the front face of the medical supplies cabinet 1A, is a camera 22A. This camera may be provided at other suitable locations such external of the upper door 2 or internal thereof when closed and only become exposed when the door 2 is open. In FIG. 3A, the camera 22A is shown to be located at or near the centre of the front face 5A of the cabinet 1A facing the mirror. In that way, the camera 22A can also capture the images that is displayed by the mirror. This is useful, because if the door is opened as shown in FIG. 3A, the camera can capture the items/receptacles on the door side as well as the images displayed by the mirror for example, which could for example be the items/receptacles present in the front face 5A of the cabinet 2A.

Optionally there may be additional camera(s) but preferably there is only one camera.

The camera 22A may run continuously to record activity in front of the medical supplies cabinet. Alternatively, the cameras 22A,23A may record intermittently and may for example only record activity in front of the medical supplies cabinet 1A when one or both or a respective door is at least partially opened. The footage recorded may be transmitted to a local or remote storage device for subsequent and future review. The cameras 22A may so take footage or a photo or photos or all.

Optionally an alert button 24 may also be provided.

In a preferred form one or several variation(s) of capacitive sensing of items is/are utilised by the medical supplies cabinet 1.

Figure 3B:
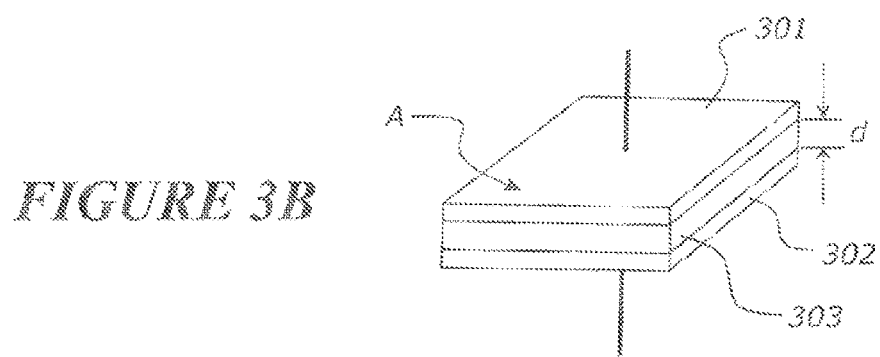
FIG. 3B shows a general purpose capacitor.

Capacitive sensing to detect a change in a capacitor may be implemented in at least one of three ways:

1. As the dielectric, k, changes due to absence or presence or change in configuration of an object between capacitor electrode plates,
2. As the area of overlap of capacitor electrode plates changes, and
3. Where the distance capacitor electrode plates changes due to the plates moving closer or further apart, FIG. 3B shows a general purpose capacitor 300. The capacitor comprises a dielectric layer 303 that is sandwiched between two conductive plates 301, 302. The principal of capacitance operating is as follows:

$$C = k\varepsilon_0 \frac{A}{d}$$

where, C is capacitance, k is relative permittivity of the dielectric material between plates, $\varepsilon_0$ is permittivity of free space, A is areas of the plates, and D is the distance between plates.

The capacitance value is affected by the dielectric value i.e. dielectric constant K, the areas of the plates 301, 302 i.e. corresponding/overlapping areas of the plates 301, 302 and the distance d between the plates.

In one form capacitive sensing may be employed by the medical supplies cabinet 1 for determining the relative position between two components of the medical supplies cabinet.

Figures 4A, 4B:
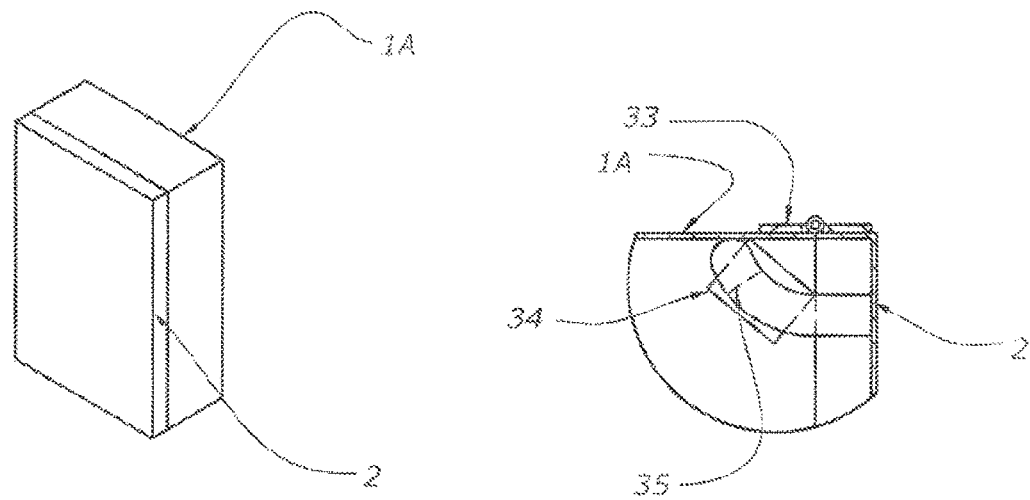
FIGS. 4A and 4B show two views of the medical supplies cabinet with the door in a closed position.
Figures 5A, 5B:
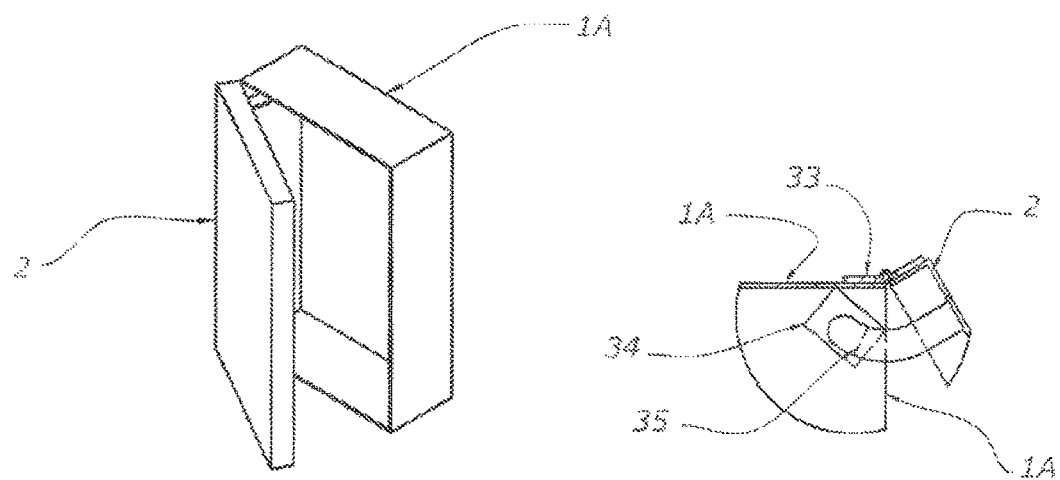
FIGS. 5A and 5B show two views of the medical supplies cabinet with the door in an intermediate position.

In one example the housing 1a of the medical supplies cabinet and a door 2 may rely on capacitive sensing to determine the relative position of the door 2, to the housing 1a. With reference to FIGS. 4-8 reference is made to door position sensing using capacitive sensing. In FIG. 4a the housing 1a and the door 2 are shown in a closed condition. In FIG. 5a the housing 1a and door 2 are shown in a partially open condition and in FIG. 6a the housing 1a and door 2 are shown in a fully opened condition. The housing and door may be connected by a hinge 33 to allow such movement to occur. The door arrangement can be one of many shapes and configurations and is shown in FIGS. 4-6 in a simplified form for clarity. The door 2 has a door arm that may be used to retain and/or lock the door open and closed. Preferably, the arm preferable also carries a metal plate 35. A capacitive sensor 34 is placed by the housing 1a so that as the door 2 opens and closes the metal plate 35 covers and uncovers the capacitive sensor 34.

With reference to FIGS. 7 and 8 the details of the capacitive sensor 34 are shown. The capacitive sensor 34 comprises a first sensing element and a second sensing element. The first sensing element is preferably fixed and the second sensing element is preferably moveable e.g. mounted to the door 2. A first fixed capacitive plate 37 (i.e. first plate) and a second fixed capacitive plate 38 (i.e. second conductive plate), usually ground are shown. Capacitive plate means a plate that is part of a capacitive sensor. Capacitive plates may be active plates i.e. charged plates that receive a current or may be static conductive plates that are not connected to an electrical power source. The capacitive plates are preferably electrically conductive plates made from a suitable material e.g. a metal.

These are preferably attached to the housing of the cabinet 1, 1A. They are preferably provided in the same plane as each other as can be seen in FIGS. 7 and 8. One of the capacitive plates is typically ground and the other connects to a capacitance meter. In the absence of the metal plate 35, as seen in FIG. 7 a weak electrical field 39 is present and the capacitance measured is small. That is, the effective area of the capacitor is small and the distance between the plates is large. When the metal plate 35 is present the electric field lines 40 are intensified and the capacitance increases with the degree the metal plate covers the two fixed plates. With one or more of the arrangements shown the degree the door is open can be sensed. The moving metal plate can be an existing metal feature of the door. In one arrangement the metal feature may be is a spring or another biasing member used to hold the door open.

The spring may function as the moving plate of the capacitor and move relative to the fixed capacitor plate. FIGS. 17A and 17B show examples of a fixed capacitor plate 48 i.e. a sensing element of the capacitive sensor being attached to a moveable spring 47. The sensing element i.e. the capacitor plate 48 is an electrically conductive element. The sensing element 48 may be an active element i.e. may be connected to an electrical power source. Alternatively, the fixed sensing elements 37, 38 e.g. fixed plates 37, 38 may be active elements that are connected to an electrical power source. The spring 47 preferably biases the door toward the open position and the moveable sensing (second sensing element) element i.e. plate 48 is mounted or disposed on the spring 47. Alternatively, the spring 47 may be a metal spring that itself forms the moveable sensing element 48.

Alternatively, the spring 47 may bias the door toward the closed position and the moveable sensing element 48 may be disposed on the spring 47.

The spring 47 is preferably pivotably mounted to a wall of the receptacle. The spring 47 is preferably moveable along an arcuate path relative to the wall of the receptacle. The moveable sensing element i.e. capacitor plate 48 moveable along the same arcuate path and moves past the fixed plates 37, 38. The fixed capacitive plates are preferably presented on or disposed within the wall of the receptacle. FIG. 17A shows the door in an open position with the spring 47 and capacitor plate 48 at a first position. FIG. 17B shows the door in a closed position. As shown in FIG. 17B the spring 47 and the capacitor plate 48 are in a second position.

Knowing the door position is useful at least because:
a. At a certain position of the door being open and/or closed, a photo may be taken or a video recording may commence, using one of or both of the cameras 21, 23. This is particularly useful when the door is closed and the camera is then obscured by the door. Once the door reaches a certain extent of opening the camera can be activated.
b. When a door that is jammed open for a long period of time, an undesirable status of the cabinet is detected. An alert may issue, for example, the alert may provide notification to a person local to the medical supplies cabinet, and prompt that person to go and check the status.

Other means of achieving a sensing of the door position may be by use of light detection sensors or mechanical means such as micro switches/reed switches. Using capacitive sensing more than just the door open or door closed conditions can be measured but also the degree of opening.

Figure 12:
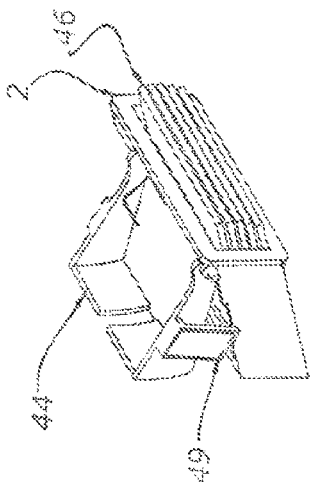
FIGS. 9 to 15 show various views of a receptacle for holding eye pads and a capacitive sensing associated with the receptacle.
Figure 10:
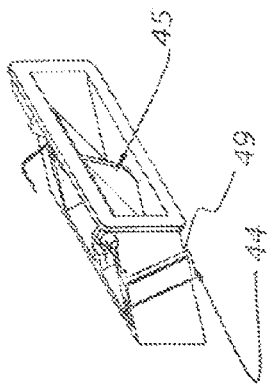
Figure 14:
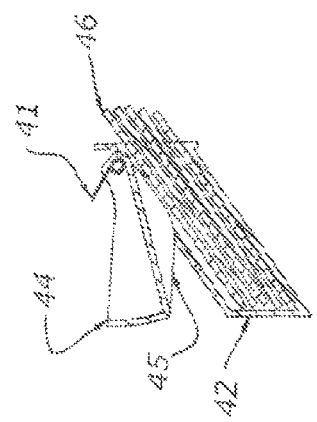
Figure 11:
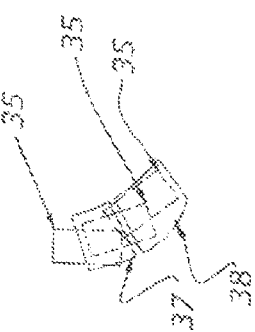
Figure 13:
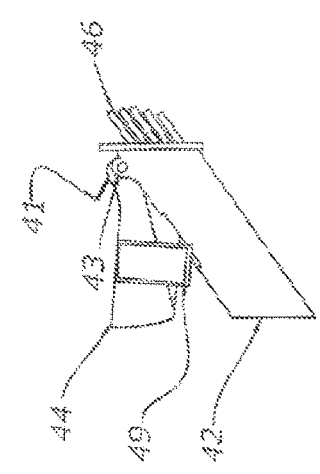
Figure 15:
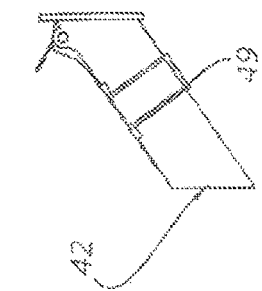
Figure 16:
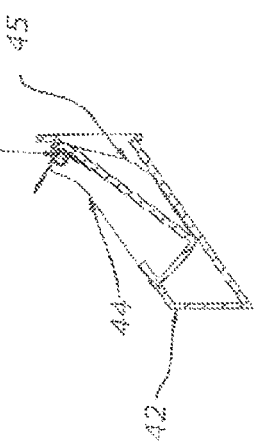
Figure 9:
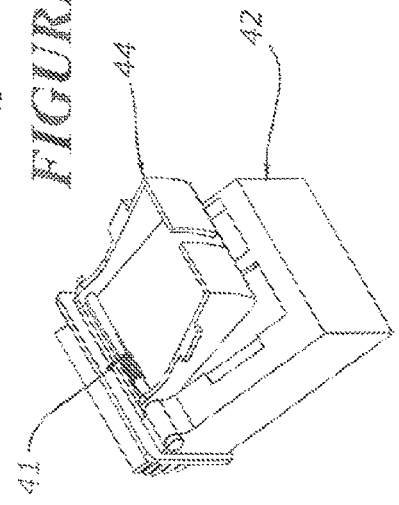

A similar method of capacitive sensing can be used for sensing the dispensing of articles from a receptacle. Reference for example will now be made to FIGS. 9-17 which for illustrative purposes shows capacitive sensing applied to a receptacle within which eye pads 46 are located. The eye pads 46 are contained in individual wraps and may be individually dispensed from the receptacle. The receptacle 42 has a cavity within which a stack of wrapped eye pad 46 are located. The wraps are able to be positioned in the receptacle 42 in a stacked configuration as seen in FIGS. 12 and 14. A sensor arm 44 is able to locate on top of the stack. The sensor arm may pivot at pivot point 43 relative to the housing of the receptacle 42. The sensor arm 44 may include an extension piece 45. The extension piece 45 is preferably a planar member. More preferably the extension piece 45 is a fin that can rest on top of the stack. The extension piece 45 may be any suitable substantially flat, planar member. As one or more wraps is/are removed from the stack (whether it is the top wrap or bottom wrap or any intermediate wrap) the stack height of the pack reduces and the sensor arm 44 pivots relative to the housing of the receptacle 42. A spring 41 may be provided to facilitate this pivoting motion. Carried by the sensor arm 44 may be one of the metal plate 35 or capacitive plate 34 and acting in concert therewith may be the other of the metal plate 35 or capacitive plate 34 carried by the housing of the receptacle 42. One part of the capacitive sensing plates may be mounted to a support 49 as seen in FIGS. 10 and 12.

The angular position of the sensor arm 44, correlating to the stack height of the packs 46, can hence be measured. As seen for example in FIGS. 16 and 17, the moving metal plate 35 may move between a bin full position and bin empty position as it moves relative to the first and second capacitive plates 37 and 38. In a preferred form a spring 41 is provided but alternatively the weight of the sensor arm 44 may be sufficient to ensure pressure is applied to the top of the stack. It will be understood that a capacitor is formed between the separated relatively moving plates and a read capacitance value is proportional to the overlap of the plate 35 with the plates 37/38.

The preferred two fixed plate approach ensures that when the bin is full, one plate is covered (maximum capacitance) and the other fixed plate is uncovered (minimum capacitance) and when the bin is empty the previously covered plate is uncovered (minimum capacitance) and the previously uncovered plate becomes covered (maximum capacitance). This arrangement helps reduce errors due to the moving plate distance from the fixed plate changing (which may occur when for example the pivot axle may have some slip in it which can cause the sensor arm 44 to move sideways a small amount). This arrangement can help reduce errors in the capacitive sensing due to mechanical defects or due to mechanical wear and tear. The geometry of the measuring arm, it's pivot point and location of the sensors, can be designed so that the effect of movement of the arm can be amplified. For example the arc that the plate moves over between its two extremes of movement can be adjusted by adjusting geometry appropriately. This can be used to increase sensitivity to measuring the dispensing of thin items at the expense of larger capacitive plates.

The arm preferably has a tongue or fin (see extension piece 45) shaped to focus the displacement activity on a particular spot on the top of the stack. It is preferably focussed on the middle portion of the uppermost pack in the stack.

The provision of a fin or similar element as part of the sensing arm 44 has the advantage in obtaining better readings, such as:
a. where the wrap and/or the wrapped product is flimsy and may not be pushed fully home into the receptacle, bringing a contact point further forward in the receptacle,
b. where the product is non-uniform and the thicker part is at the middle of the product rather than at the peripheral edges of the pack,
c. by providing a sensing point defined by the fin that is closer to the pivot point 43 so to enhance measuring sensitivity.

FIG. 17 shows an arrangement where there are more than two fixed plates 37/38 cooperating with one moving plate 35. It also illustrates how the radius (R1, R2) can provide for a substantial change in distanced travelled (X1, X2) giving more capacitive change or allowing more fixed plates to be used.

Capacitive sensing that may be employed in the cabinet may occur by virtue of a change in the dielectric provided between two capacitor plates. This may have application in situations where a stack of packs may be provided that can be removed to thereby decrease the stack height where the sensing arm approach as described with reference to FIGS. 10-17 is not appropriate.

Figure 18:
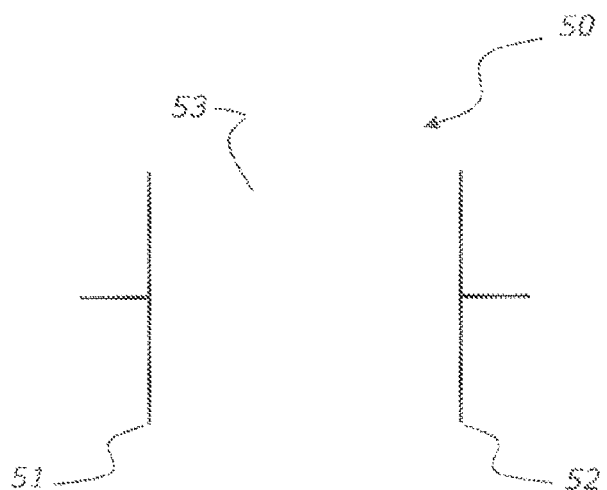
FIGS. 18 to 20 show a configuration of a capacitive sensor within a receptacle for detecting the presence of a medical item.
Figure 19:
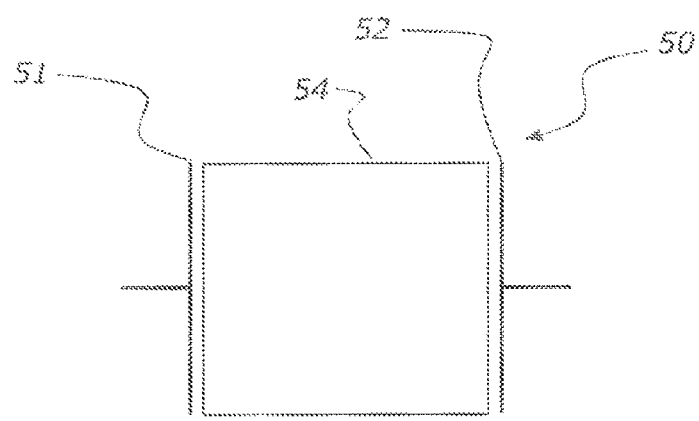

With reference to FIG. 18 there is shown a side view of a capacitor 50 with a first capacitor plate 51 and a second capacitor plate 52 and there is a dielectric substantially comprising of air intermediate 53. For this situation the capacitance is minimum (Cmin). FIG. 19 shows a side view of the capacitor 50 with a product 54 that has a dielectric substantially different to air completely occupying or substantially occupying the volume between the two plates 51 and 52. For this situation the capacitance may be maximum (Cmax).

Figure 20:
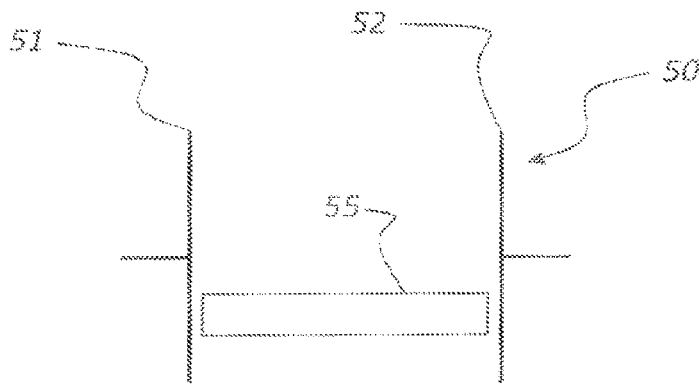

FIG. 20 shows a side view of the capacitor 50 with a product occupying a portion of the volume between the plates 51, 52 and extending to each plate 51, 52. For this situation the capacitance falls between Cmin and Cmax in proportion to the amount of area of the plates 51, 52 that is covered by the product 55. This mode of measuring capacitance change can allow for the sensing of stack heights and therefore the sensing of the dispensing of items from a stack. With reference to FIG. 23-26 there is shown a receptacle of the medical supply cabinet 1 where for example a stack of salve wipes can be retained. This compartment may for example be located at receptacle 13. The wound cleaner or salve wipes may comprise of individual wipes individually wrapped in a sealed wrap 62, the stack of such sealed wrapped wipes located inside a box 61. Whether boxed or not the plurality of wraps 62 can be located in at the receptacle 13 of the medical supplies cabinet. Stack height and hence a count of the number of wraps still remaining in the stack can be achieved by capacitor sensors that will now be described.

FIG. 24 illustrates a receptacle from which a stack of items can be dispensed. FIG. 21 shows a variation to the stack of FIG. 23 wherein the stack is enclosed in a box 61. The box 61 may be loaded into the receptacle as shown in FIG. 21 or alternatively the items to be dispensed may be provided in the receptacle 64 in a stacked configuration as shown in FIG. 24. In the preferred form the items in the stack are removed individually preferably from a slot at the bottom of the box 61. A receptacle of the medical supplies cabinet is configured to retain the one or more boxes 61. A capacitive sensor or capacitive sensor arrangement is associated with the receptacle. In some examples a plurality of capacitive sensors may be used. The capacitive sensor comprises a plurality of spaced apart sensing elements. In one exemplary configuration one and preferably a plurality of capacitive plates 65 are arranged at one side of the stack for example at side wall 63 of the receptacle. On the opposed side wall 64 an opposed plate 68 may be provided. The opposed plate 68 is preferably grounded.

The other plates may consist of an array of plates 65, the array extending in the direction of the stack height.

FIG. 26 illustrates provision of two boxes 61a and 61b at the receptacle 66. The top box is a spare box, and when the bottom box runs out and is removed, then the top box drops down and is able to be opened and dispensed. As the top box only needs to be sensed, it does not need an array of capacitors or accurate sensing techniques to detect the specific quantity of items within the box. Since the top box is a spare box, just its presence needs to known which can be achieved by larger sized capacitor plates as opposed to the array structure. Hence as shown in at least FIGS. 21 and 24, the upper capacitor plate of the array is of a larger size than the other capacitor plates.

When the system detects the top box has gone or been removed (now in bottom position), a replenishment request can be sent. In this way when new stock arrives, there is always a place for it in the kit. Consider if only one box is able to be in the holder at one time, then either the new box has to be stored elsewhere, or reordering has to be done when it runs out, leaving the kit uncompliant for the order fulfilment time. The array of capacitors allows individual uses to be noted for health and safety reporting. The replenishment request may be an audible alarm or a visual alarm or an electronic message may be sent to a mobile device or computer of a technician or health and safety office or any other suitable person, using a suitable communication module that may be integrated into the medical supplies cabinet.

The plates may be any suitable metal such as aluminium or copper. In one instance the plates are preferably aluminium plates that are able to be adhered on to the inside of the wall or walls 63 and 64 of the receptacle. The plates may be part of a printed circuit board.

Items may be stacked in the receptacle 66 in an individual manner or in a box such as the box 61. As more items are stacked up, the capacitance reading from the array increases. Addition or removal of items is recorded by the change of capacitance.

The number of capacitors 65 in the array is tailored to the sensitivity of the capacitor array. More capacitors tends to mean they are smaller, in area and value, which is harder to measure accurately, as the stray capacitances to other objects cause noise on the signal. If a product has a size of 1% the area of the 'effective' capacitor plate area, then its presence in the capacitor may cause an approx. 1% change. If the capacitor is divided into 10 separate capacitors, then the same product has a 10% change for the capacitor it is detected within or for the capacitor the product is placed within. As a rule of thumb approximately five times the area of the product provides a good signal to noise ratio and helps in detecting small objects. The capacitors being arranged in an array configuration help to provide more accurate detection of the products that have a small cross sectional area such as for example wound cleanser wipes. The array of capacitors also helps to detect products that have a small height dimension or are laid flat such as wound cleanser wipes, as compared to for example saline tubes. The array structure of the capacitors helps to reduce noise and false positive detection for small sized products. But having bigger changes in capacitance to a product being removed.

In one extreme the array consists of one capacitor (two opposed plates) for all products in the receptacle. In another extreme there is one capacitor for each product in the receptacle to be sensed.

The measurement principal (dielectric change i.e. dielectric value or dielectric constant change) allows for more accurate determination of individually removed or inserted items from the stack:

1. Where the array of sensors 65 together with the opposed plate 68 are provided, it is possible to focus on areas of the box.
2. Where the capacitive sensors (i.e. sensing elements or sensing plates) can be on more than one side of the box to detect situations where items are not dispensing correctly or if the items in a box are misaligned.

3. Where the capacitive sensor has a ground plate 68 strategically focussed on opposite side from the capacitive pad to increase sensitivity. The ground plane 68 being located on the opposite side of the capacitive pad i.e. opposite to the array of capacitive plates 65 focusses the electric field through the product.

The configuration shown in FIGS. 21 to 27 comprises an additional guard plate (not illustrated) larger than the plate 65 may be positioned on the other side of the PCB that supports the plates 65. Preferably the configuration comprises a plurality of guard plates, which are larger than the plate 65. Preferably a plurality of guard plates may be used, wherein each guard plate is associated with a single plate from the array of plates 65. The additional guard plate or plates have the same signal i.e. same level of current or voltage or power applied to the additional plate. Hence the capacitance between guard plate and the sensor (i.e. plate) 65 is 0. This focusses the electric field from each sensor plate of the array of sensors 65 through the product.

For situation (1) above, the plate 68 is preferably a ground plate and helps to focus the electrical field from the array of sensors 65 to the plate 68, thereby driving most of the electrical field through the products in the and improve electrical coupling via the electrical field between the sensors 65 and the ground plate 68. The electric field is strongest between the ground plate 68 and the sensors 65. If the plate 68 was not grounded then the electric field would disperse over long distances to ground and may not pass through the product. The arrangement of the sensor 65 and the plate 68, in particular the plate 68 being ground improves sensitivity of the capacitive sensor (formed by sensors 65 and plate 68), and helps to ensure the electric field passes through the product.

Figure 23A:
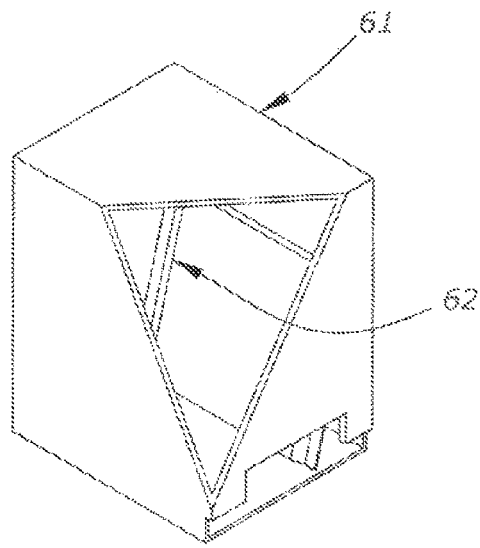
FIGS. 23A to 23D show an alternative configuration of capacitive sensors on a receptacle to detect misalignment of stacked medical items.
Figure 23B:
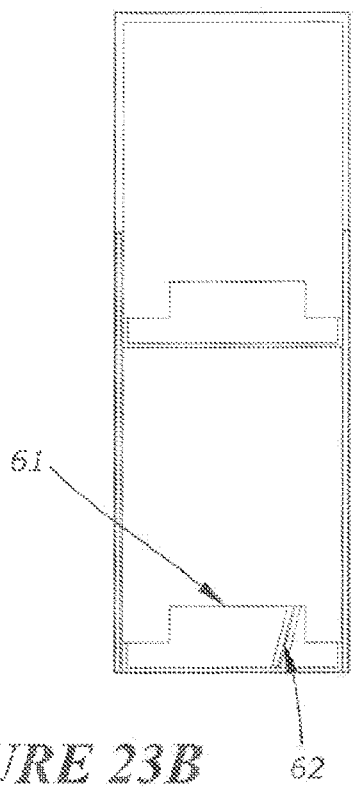
Figure 23C:
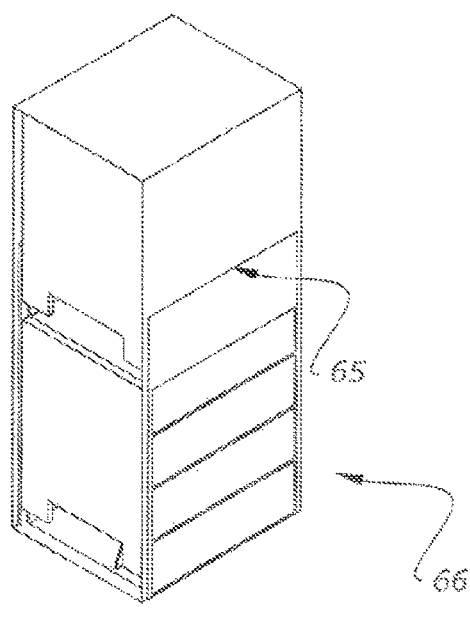
Figure 23D:
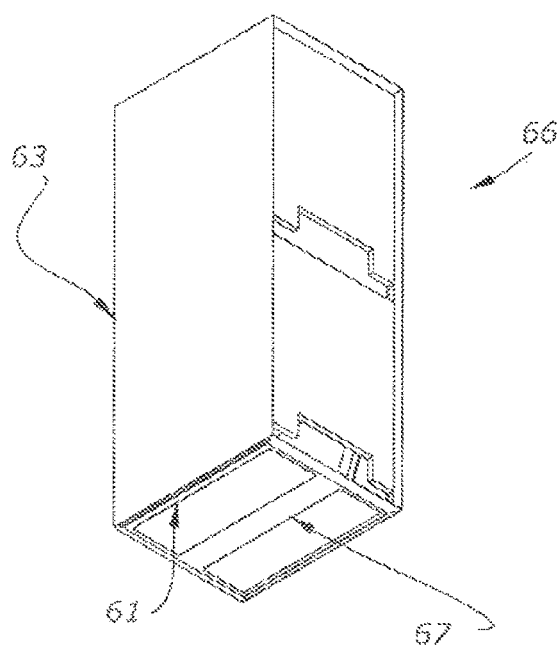

For situation (2), the plurality of sensors are positioned at various locations on or in the receptacle, on more than one side of the box to detect a misalignment of items or incorrect dispensing. FIG. 23A shows cutaway view of a box that shows wipes in an incorrect position. The wipes are standing substantially vertically instead of being laid flat within the box 61. FIG. 23C shows the array of capacitive sensors 65 arranged on the side wall 63 of the receptacle that receives and retains the box 61. The misaligned arrangement presents a large dielectric area due to the orientation of the wipes. A large dielectric value results i.e. a higher dielectric constant thereby leading to an increased capacitance. This increase in capacitance is detected by a processor since the capacitive sensors 65 generate a signal indicative of the increased dielectric value. The increased dielectric value causes an overestimation of the number of wipes. The receptacle 66 comprises extra base capacitive plates 67a and 67b disposed in the base of the receptacle 66. These extra base capacitive plates 67a and 67b can sense the number of wipes in the standing configuration or at least alarm or send an alert that the medical items e.g. wipes in the illustrated example, are misaligned within the box 61. In the illustrated configuration of FIG. 23A the base plate 67a would have a higher dielectric i.e. a higher capacitance than base plate 67b. The receptacle 66 may comprise more than two base plates associated with the base of the receptacle. A plurality of base plates is preferably used for the same reasons as above with respect to improved signal to noise ratio.

Alternatively, the array of capacitor plates 65 may be arranged in a substantially vertical arrangement in order to detect misalignment or detect a vertical configuration of medical items.

The shape and configuration of the receptacle 66 is preferably such as to ensure that a box or the boxes are held in a constant position to the sensor, avoiding changes in signal level due to the movement of the box and the holder. Therefore, the shape and configuration of the receptacle is designed to ensure that when a box of items is replaced, the new box assumes the same condition and a consistent condition as required.

Metering of the change in capacitance may be achieved in many ways such as by measuring the
1. Voltage of a sinusoidal voltage applied to an RC circuit,
2. A bridge circuit, or
3. Measuring the time to charge the capacitor (often compared against time to charge a known capacitance).

Any one of these methods may be used in any one or more of the capacitive measuring set ups as herein described.

Most of these methods require AC excitation signals, a number of references, and ADC converters. Any suitable ADC converters can be used. Further any suitable interfacing circuitry can be used between the capacitive sensors and a processor or microprocessor. The medical supplies cabinet also comprises a suitable signal conditioning circuitry that acts on signals from the capacitive sensors. The signal conditioning circuitry is preferably a combination of hardware circuit elements and software modules e.g. filters.

There also exists a low cost highly integrated circuit such as a microchip CAP-1298 device that could be used. Such a device has up to eight sensors. These devices measure a change in capacitance compared to a base value for changes in the environment. It is possible to use these to measure the capacitance directly by reading out the base calibration and counts of deviation from the base count. In this manner the absolute capacitance can be obtained cheaply and easily with simple circuitry.

The medical supplies cabinet comprises a processor. The processor is preferably a microprocessor and also includes a memory unit associated with the processor. The processor is preferably in electronic communication with the memory unit. The memory unit is a non transitory computer readable medium that stores executable instructions. The processor configured to execute the stored instructions in order to detect an event e.g. detect the presence of one or more medical items within the receptacles or the number of medical items in a package, or the number of packages of medical items within the receptacle. The processor also includes suitable bus circuitry and may also include a wireless communications module allowing the processor to communicate over a telecommunications network e.g. 4G. Further the communications module may also be configured to allow the processor to send text messages or other alerts to a suitable persons phone or send email.

Figure 28A:
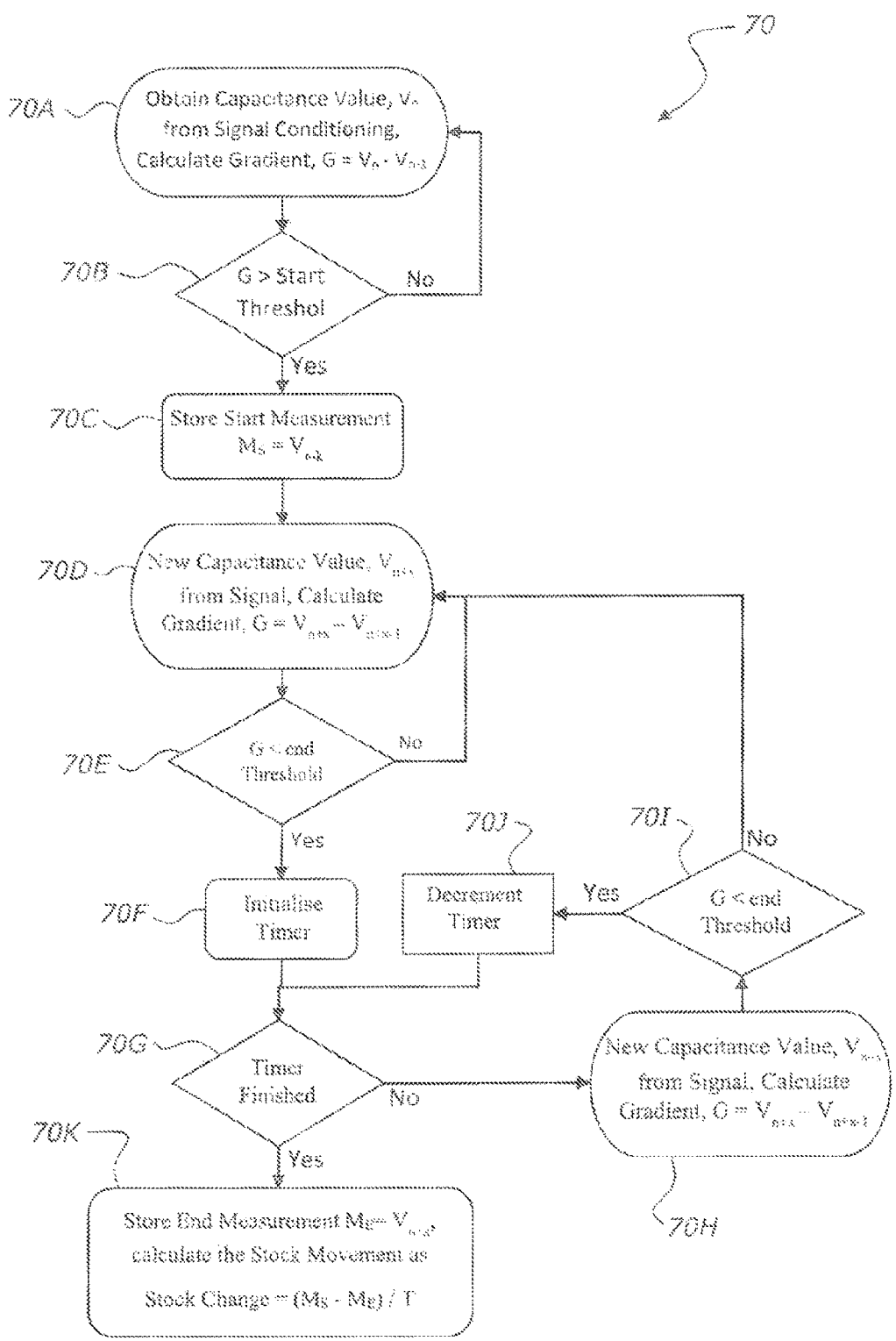
FIG. 28A illustrates an event detection method to detect an event (e.g. a medical item being introduced or removed from a receptacle).

FIG. 28A is representative of an example event detection algorithm 70 that may be used. Referring to FIG. 28A the method of event detection begins at step 70A. At step 70A a signal from the capacitive sensor or capacitive sensors are used. The signal may be a voltage value. At step 70A the gradient (i.e. a rate of change) of the signal is determined. Step 70B comprises checking if the calculated gradient is greater than a start threshold. If the gradient of the signal from the capacitive sensor does not exceed a threshold, the method returns to step 70A. Step 70A is preferably repeated i.e. the capacitive sensor signals are sampled regularly at a suitable sampling rate. A gradient exceeding the start threshold indicates an event start i.e. interaction between a user and at least receptacle of the medical supplies cabinet. The start threshold is preferably a predetermined or pre-defined threshold. The threshold may be stored in the memory unit. A plurality of start thresholds may be stored, wherein each start threshold may correspond to a particular type of medical item received within the receptacle. A plurality of measures signals at step 70A are preferably stored in the memory unit. The memory unit may include temporary memory to function as a buffer, wherein the temporary memory unit may be any suitable type of memory, preferably a non-volatile memory or a solid-state memory unit.

If the gradient exceeds the threshold at step 70B, the method proceeds to step 70C. Step 70C comprises storing a start measurement. The start measurement is the measurement that exceeds the threshold. Step 70D comprises receiving a second (i.e. new) signal from the capacitive sensor or sensors. Preferably step 70D comprises determining a gradient between consecutive signal measurements. Step 70E comprises determining if the gradient is less than an end threshold. If the gradient is less than the end threshold, then a timer is initialised at step 70F. If the gradient is not less than the end threshold, then the method returns to step 70D. The gradient at step 70D being less than the end threshold denotes the end of an event i.e. denotes no interaction between or an end of interaction between a user and at least one receptacle of the medical supplies cabinet.

Following step 70F, the method progresses to step 70G. Step 70G comprises determining if the timer has finished i.e. expired. The timer is considered as being finished when there is no change between two consecutive signal measurements, which denotes a steady state condition i.e. no interaction between a user and the medical supplies cabinet or any receptacle therein.

If step 70G returns a no i.e. the sensor or sensors are not at steady state, the method proceeds to step 70H. Step 70H may be a substantially similar operation to that of step 70D. Step 70H comprises determining the gradient between two consecutive signal measurements. From step 70H, the method proceeds to step 70I that comprises determining if the calculated gradient is below an end threshold. If the determined gradient is less than an end threshold i.e. a yes is returned at step 70I, the method progresses to step 70J. If a no is returned at step 70I, the method returns to step 70D. Step 70J comprises decrementing the timer. Decrementing the timer reduces the amount of time of the timer, since the check at step 70I indicates that an event has ended. Once the timer expires at step 70G, the method proceeds to step 70K. Step 70K denotes a steady state. Once the time expires, the processor is configured to store an end measurement.

The start and end thresholds are preferably predefined thresholds and can be customised for different medical items. The thresholds may also be set or determined to allow detection a specific interaction e.g. removing a single eye pad or taking out an entire package of medical items. The thresholds may also be customised to account for sensor characteristics e.g. sensor drift or sensor noise.

Figure 28B:
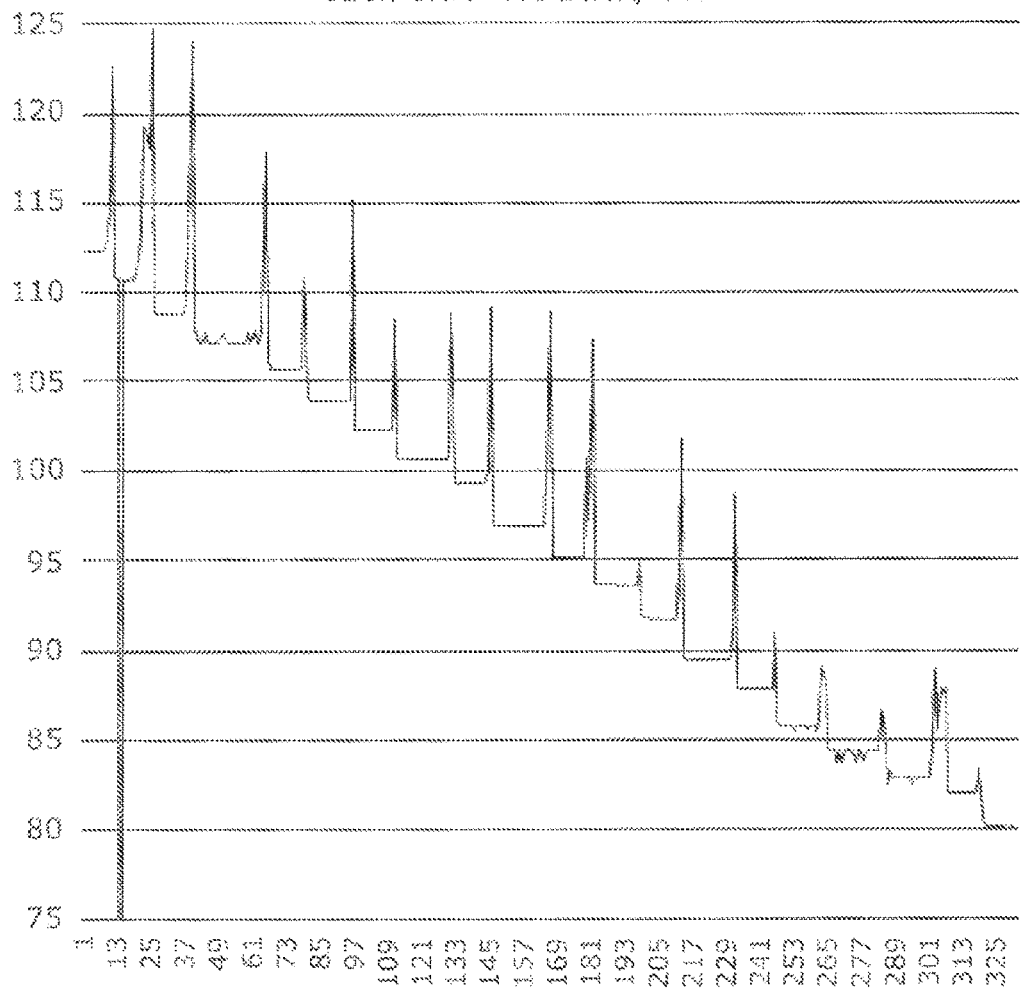
FIG. 28B shows an exemplary plot of the output of a capacitive sensor detecting events.

FIG. 28B shows typical signals returned by a capacitive sensor associated with a receptacle of the medical supplies cabinet. The plateaus in FIG. 28B occurs after each item is taken from a stack of items (e.g. wraps) such as shown in FIGS. 21-27. The spikes are due to increased capacitance as a user is taking a pack (which increases the capacitance of the system because the user presents a large capacitance to ground).

The X-axis is samples (i.e. time) the Y-axis relates to the capacitance read between the two plates (the two opposed plates between which the stack of packs if provided).

The signal condition algorithm consists
1. A means to detect invalid capacitance readings and rejects them (eg. Sample 13 seen in FIG. 28),
2. A median filter that selects the median of the proceeding n, values as input to the next stage (where for example n is 3). The median filter allows removal of single outlier readings due to noise.
3. One or more exponential averaging or smoothing filter such as seen at that averages the reading from the sensor and includes a means to initialise the filter at the start of event detection, that minimises the settling time. Exponential averaging filters are used to reduce noise. In a preferred arrangement a fast filter that reacts quickly to the signal, but gives adequate noise suppression to minimise false event detection is used. In addition a slow filter that provides adequate noise suppression and improves the measurement accuracy is used. Both filters are used in combination to provide a better signal quality to the processor. The filters may be implemented using electronic hardware or may be implemented as software filters as part of the signal conditioning circuitry.

Each of the spikes in FIG. 28B represent an interaction with the medical supplies cabinet i.e. a user is taking a medical item or a package from one of the receptacles. FIG. 28B is an exemplary plot of the capacitive sensor associated with a single receptacle. The processor of the medical supplies cabinet is configured to process multiple signals from multiple capacitive sensors since a plurality of receptacles may have one or more capacitive sensors associated with them. The method of FIG. 28A is used to process the signals of the capacitive sensor and determine events occurring e.g. each of the spikes. The method of FIG. 28A is used to identify the start of the event i.e. the start of the spike and an end of an event, when the signal has reached a plateau i.e. steady state. The algorithm (i.e. method) of FIG. 28A is preferably executed regularly e.g. at the sampling rate of the sensors.

The algorithm measurement consists of:
1. The event start has a history buffer that selects a start measurement (START cap-value) from Milliseconds before the event start, where M is set to obtain a value of the proceeding static state plateau before movement was detected.
2. An end measurement that selects the final settled value, (END cap-value).
3. Determining of an absolute number of items, and the change in number of items taken/restocked this event.
4. Application of rules that reduce errors if the rate of change (i.e. gradient) of measured capacitance signals are inaccurate.

The algorithm is illustrated in FIG. 28A in more detail.

In one example the stock movement is calculated by subtracting the start measurement from the end measurement. Preferably the stock movement is calculated based on a rate of change of the measurements i.e. the end measurement minus the start measurement divided by a nominal time period. The length of the timer can relate to the length of the interaction that can denote a plurality of items being removed or added into the receptacles. The rate of change of the measurements can denote the number of items removed or added. A positive gradient can mean the addition of items while the negative gradient can denote removal of items from a receptacle. The processor is further configured to determine an absolute value of the end measurement of an absolute value of the end value divided by time. The absolute value denotes or indicates a total number of items in a receptacle. The absolute value as described is used as a reference check to filter out false positives or other noise. The processor may be configured to store a stock level for each receptacle as a number or counter. The processor may be further configured to increment or decrement the stock level based on the event detected e.g. if an item removal is detected then the stock level is decremented and similar for incrementing. The absolute value of the sensor signal is used as a check to reduce errors. The initial stock level may be entered at installation or may be re-entered every time a receptacle is stocked to a required level. Although not shown here the initial stock level may be manually entered via an alphanumeric keypad associated with the medical supplies cabinet. Alternatively, and more preferably the processor may be configured to run a calibration step where the capacitive sensor is configured to measure the contents of the receptacle and may generate a signal indicative of the number of items.

Some example rules are:
A. Adjust the totals if the delta value i.e. gradient is greater than an item threshold indicating an item was taken, but the absolute value states the total is the same. This ensures an event is reported.
B. When the total i.e. total stock level (which may be a running total or counter) is decremented but the absolute value is greater than a previous total, the total is not changed.
C. Similarly if the total is incremented but the absolute value is less than the previous total, the total is not changed.
D. A change in the entire content of a receptacle e.g. for a receptacle that can only hold one item, the stock counter may be binary.

As seen from the rules above the absolute value acts as a check to ensure that the event detected based on the delta i.e. gradient of sensor signal actually relates to an item being removed or added. The absolute value is used to filter out noise and differentiate between an item being taken or removed and noise. Preferably the absolute value is also checked against a threshold. The thresholds described herein may all be stored in the memory unit and accessed by the processor.

In a preferred form lighting is incorporated with or into the door panel of the medical supplies cabinet. This allows for a user to visually identify the medical supplies cabinet from a distance in low light conditions. Preferably the door 2 or each door 2, 3, is of a transparent material that may be illuminated so that graphics printed or provided on a face of the panel can be back-lit and illuminated to show a sign such as a first aid cross and/or the words "first aid" or similar.

Lighting as part of the cabinet may also be used to indicate the status of the kit. For example a red light may indicate a push of the alert button 24, a blue light may indicate that there is a fault. Other colours may be utilised to indicate different function statuses or conditions of the cabinet. Lighting may also be used in way to be switched by door sensors via a processor that adjusts the light to white and correct ambient level to make seeing the products in the kit easier in poor lighting conditions.

Where the door has sensing, incorporated to sense the degree the door is open (such as by using a capacitive pad and ground pad and a floating metal hinge on the door that bridges the two. In one arrangement the floating metal is a spring used to hold the door open. The spring may be similar to the spring that carries a sensing element e.g. a plate. At a certain position of the door being open and closed a photo may be taken by one of the cameras. In some instances the camera or cameras may be triggered when an event (i.e. interaction) between the door and the user is detected. Preferably the camera or cameras are triggered to record during such event.

The medical supplies cabinet and associated system can allow for a system for management alert.

For example if the door that is jammed open this can be detected and an alert sent to a person nearby.

Management alert is a feature to allow staff using or needing to use the cabinet to contact or message others of a serious medical event without effort. The alert button 24 is provided as part of the medical supplies cabinet for such purposes. For example for a lone worker in an isolated building the internet or cellular systems are not always reliable so feedback to show success of an alert raised at the cabinet having been sent from the medical supplies cabinet to a remote location gives the worker the reassurance that an alert has been received and a response may be imminent. A light may be associated with the button to indicate that the medical supplies cabinet is connected to the internet.

When pressed the alert button can send an alert such as via SMS or email or other messaging means to an off-side location where for example a manager or first aider or ambulance staff may be prompted to respond. The response may be by way of a reply via a speaker to the medical supplies cabinet. A microphone may also be provided so that a communications channel can be established between a remotely located expert or assistant and a person that may be attending the scene of an accident and who has pressed the button 24. There may be processing in the cloud for the purposes of monitoring the status of the SMS and sends back sent, received, read signals that may be displayed on the medical supplies cabinet to let the user know that their alert has been heard.

Figure 34:
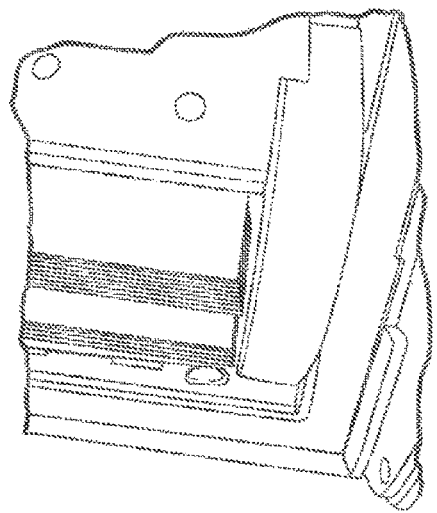
FIG. 34 shows an arrangement of medical items within a receptacle such that removal of the medical item can be detected.
Figure 35:
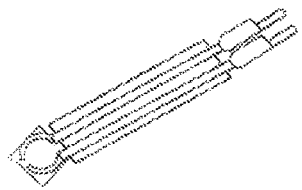
FIG. 35 shows an exemplary load sensor.

In some receptacles medical supplies may be provided, the dispensing of which is better sensed by a load sensing arrangement (i.e. a force sensing arrangement) to an application of a peak force such as a tug force or a change in force during the dispensing of such items. FIGS. 30 to 37 describe arrangements where load sensors can be used to determine tug force of objects e.g. plasters. The load sensors (i.e. force sensors) may be load cells or other sensors that detect at least an axial force e.g. a tug or a depression. FIG. 35 shows an exemplary load cell and its electrical leads.

Referring to FIGS. 30 to 33, there is shown an exemplary receptacle 81. The plasters 83 are loaded within the receptacle 81. The receptacle 81 is preferably defined by a plurality of walls and a dispensing opening presented toward a lower portion of the receptacle 81. FIG. 33 shows a close up view of the internal arrangement of the load sensor 85, the card 82 and the plaster 83 within the receptacle. FIG. 33 is a close up view of the region B in FIG. 32.

The plasters 83 are preferably stacked within the receptacle 81. For example, plasters 83 may be provided in a stacked configuration as seen in stapled to a card 82 at the end of such plasters. Alternatively, the plasters 83 may be stacked horizontally or stacked horizontally within a holder that can be placed into the receptacle.

The weight of each plaster wrap is small compared to the total weight of the pack so supplied. The plasters may be secured in the receptacle by the use of a holder, but preferably due to gravity. Plasters may be presented in a fanned manner and at the fanned region 84 are presented to the external of the medical supplies cabinet to allow a person to grab a plaster and pull the plaster from the pack.

Figure 36:
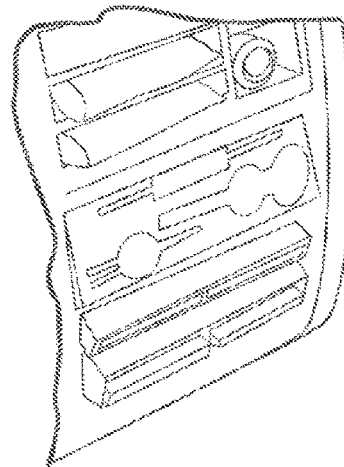
FIG. 36 shows an arrangement of a plurality of spare plaster packs within a receptacle.

FIG. 32 shows a configuration of a receptacle where multiple plaster packs comprising multiple plasters are provided in the receptacle 81. The load sensing arrangement is configured to detect the presence of both plaster packs. The upper plaster pack may be a spare plaster pack. FIG. 36 shows a configuration where there are a plurality of spare plaster packs. The presence of the plaster packs can be detected by capacitive sensing or optical sensing, as described herein.

Determining when an item such as a plaster is taken from the pack is achieved by measuring the force applied to the plaster when it is tugged. The plasters are arranged so that the cards 82 press down on a load sensor 85. FIG. 34 shows an illustration of a card arrangement such that a portion of the card presses down on the load sensor. The load sensor may be a load cell i.e. a force sensing resistor 85. The load sensing arrangement may include a plurality of load sensors (i.e. force sensors) arranged in a suitable configuration. For example, the load sensors may be arranged such that:

a. A single force sensing resistor is placed in the middle of the card (or receptacle),
b. Two forces sensing resistors, one at each end of the card (or receptacle) or more than two spaced evenly across the width of the card (or receptacle),
c. One that is shaped to span the entire width of the card (or receptacle).

The force may be measured:

a. With a common voltage divider where one resistor is fixed and the other varies based on the force.
b. By op-amp circuits that applies a base bias across the resistor.
c. By comparison under a threshold to detect a tug (where the threshold could be via a comparator, a Schmidt trigger or similar).
d. Using an ADC and detection determined by a software algorithm.

The load sensor is arranged in a suitable configuration and may be coupled to suitable interfacing electrical circuitry that allows force to be measured using one of the above stated principles. Specifically, the load sensors generate a signal that is indicative of a force applied to the force sensor. The signal generated by the load sensors is indicative of an item being removed from the receptacle by applying a force, e.g. at least a single axis force or an axial force. The processor is configured to process the signal and determine the number of items taken.

Figure 37:
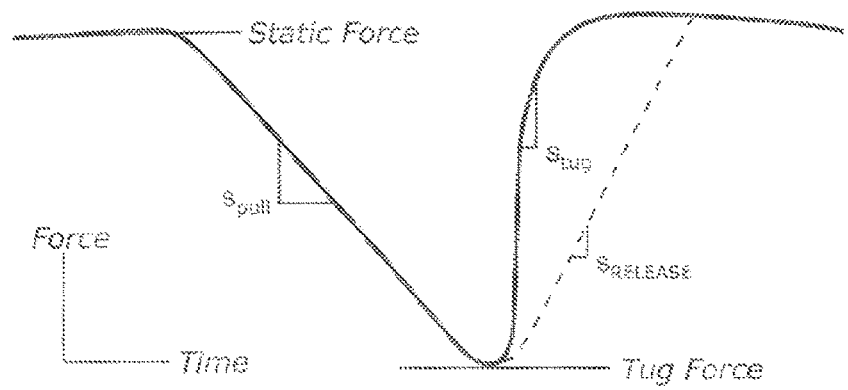
FIG. 37 shows a plot of tug force vs static force that can be used to identify a tug.

The signals from the load sensors are converted to a digital signal by an analogue to digital converter (ADC). The ADC may be arranged as part of the interfacing circuitry. Where the force is measured by the processor (or maybe the ADC having suitable processing capabilities) a tug corresponding to the removal of an item is determined by one of:

1. The static force is compared to the force during a tug. The difference between tug and static force must exceed a threshold to be a valid tug.
2. The slope of the pull force (S pull) and release (S release) forces are measured. A tug (S tug) has a sharper release force than a pull.
3. Therefore, false positives can be eliminated by measuring the forces during a tug and rejecting those where the release force slope is not sharp enough as seen in FIG. 37.

The processor is configured to determine whether a tug i.e. an axial load from a user corresponds to the removal of a medical item, in the illustrated embodiment a plaster. The processor may be configured to decrement a stock counter. The processor may determine the number of items removed or dispensed by the number of tugs detected. Each tug may be detected as a discrete tug that corresponds to a plaster being removed. The use of the load sensors allows almost real time determination of the plaster usage and also allows determination if there is enough stock of plasters in the receptacle.

As shown in FIGS. 30 and 33 the receptacle 81 may also include one or more capacitive sensors 86 disposed on a wall of the receptacle. Preferably the capacitive sensors 86 are electrically conductive plates. The plates 86 may be configured to measure the presence of each of the plaster packs. The capacitive sensors 86 may also include a ground plate associated with the front wall of the receptacle. The presence of both plaster packs changes the dielectric value between the plates 86 or between each plate 86 and an opposing ground plate. The dielectric value corresponds to a capacitance value. The sensors 86 generate a signal that is indicative of either one plaster pack or both plaster packs being located in the receptacle. The principle is similar to the operation of the capacitive sensors described in FIGS. 21 to 26.

Capacitive sensing can be used in combination with load sensing in order to keep a track of the stock small, high use items such as plasters. The load sensors allow detection of single item e.g. each single plaster while the capacitive sensors can allow detection of spare plasters being located within the receptacle. In a further configuration an optical sensing arrangement may also be implemented. In particular a colour sensing arrangement (described in more detail below) may be used in receptacle 81 in order to determine the types of plasters used in the receptacles.

The camera or cameras associated with the medical supplies cabinet may be activated if the door is opened and begin recording interactions of persons with the various medical supplies in the cabinet 1. The camera act as a theft deterrent. In one example the sensing of a tug force or the pulling of a plaster may cause the camera to focus recording on that particular receptacle. Similarly, if other medical items are detected as being used by the capacitive sensor/sensors the camera may focus on that receptacle or receptacles. The processor may be configured to store the recorded video from the camera onto the memory unit, providing the memory is a suitable memory unit.

In a preferred form several variations of optical sensing may be utilised or also be utilised by the medical supplies cabinet 1. The medical supplies cabinet 1 may use a number of different types of optical sensing arrangements to perform a number of different types of detection of one or more medical supplies or detection of one or more packs containing medical supplies.

One problem that can occur is where several different products of the same dimension i.e. same size and shape can fit into a receptacle of the medical supplies cabinet. This can occur since the medical supplies cabinet may include a plurality of similar sized and shaped receptacles that may be general purpose receptacles for retaining any packs containing medical supplies. Further the situation described can occur, in use, where multiple users may use the medical supplies cabinet 1, and some users may misplace or purposely put various packs containing medical supplies into the wrong receptacles or randomly put the packs into any receptacle (e.g. the easiest to access receptacle). It is not reasonable to expect users to adhere to the specific position requirements for the packs within the designated receptacles, especially when the receptacles may all be similar in size and shape.

This can cause issues for the next user as the next user may pick the wrong pack or has to search around for a desired pack containing medical supplies. The misplacement of packs within receptacles can also cause issues with stocktaking of medical supplies within the medical supplies cabinet 1. In some instances of use the stock within the medical supplies cabinet is essential and can be a regulatory requirement.

The optical sensing arrangements are preferably disposed at one or more of the receptacles of the medical supplies cabinet 1, and may be used to address one or more of the problems mentioned above.

Optical sensing arrangement may be configured to operate using any suitable optical sensing format for example, colour sensing, visible light sensing, ultraviolet (UV) sensing, infrared (IR) sensing or laser sensing. Alternatively, any other suitable optical sensing format can be used in the medical supplies cabinet 1.

The optical sensing arrangements are used to determine:
1. the type (i.e. identity) of pack containing medical supplies
2. the number of packs containing medical supplies within a receptacle
3. the state of a pack containing medical supplies within a receptacle, for example if the pack has been tampered with
4. the expiration date or if medical supplies (i.e. medical items) are expired based on the colour of the packaging.

Exemplary optical sensing arrangements will be described with reference to the figures.

Figure 38B:
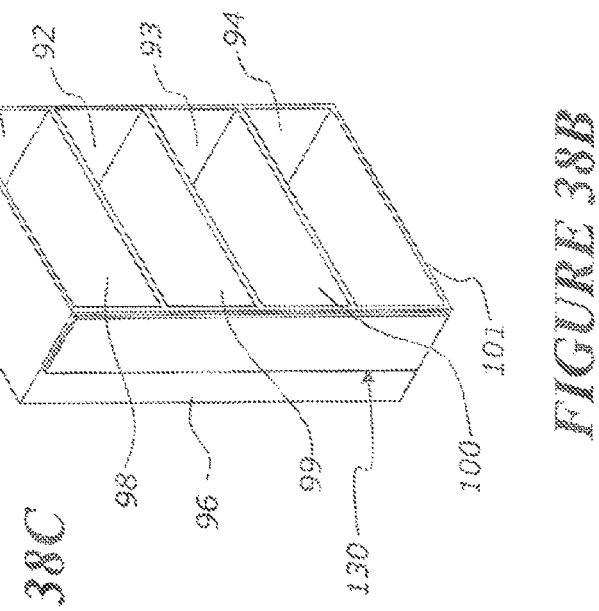
FIGS. 38A to 38C show a plurality of plurality of receptacles with an optical sensing arrangement associated with each receptacle.
Figure 38C:
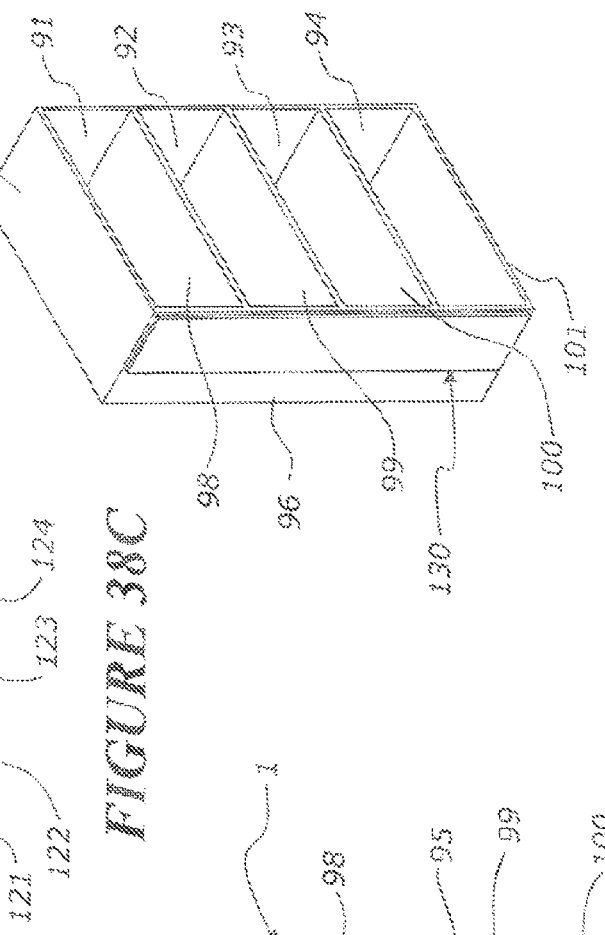
Figures 38D, 38E:
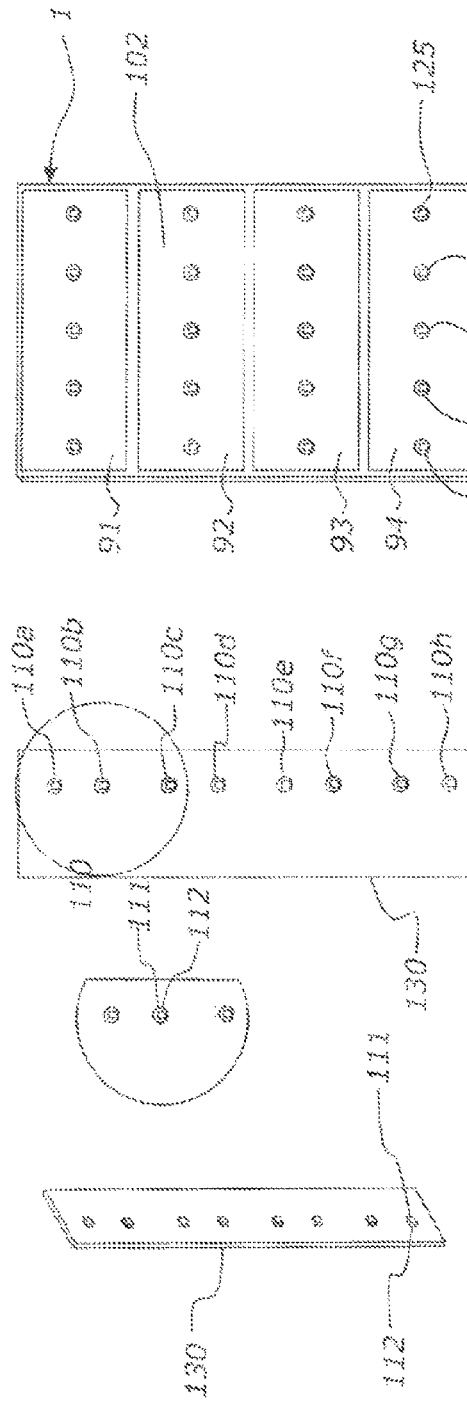
FIGS. 38D and 38E show an example configuration of a plurality of optical sensing arrangements on a printed circuit board.
Figure 38A:
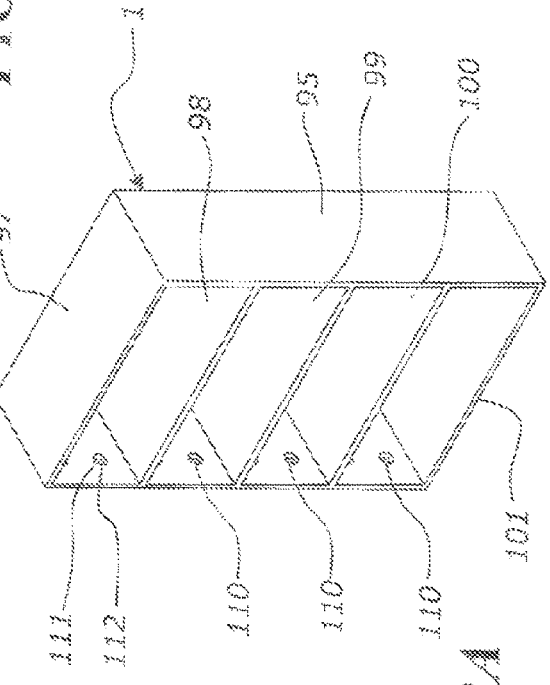

FIG. 38A-38E show a plurality of receptacles of the medical supplies cabinet 1. The receptacles can be used to retain a number of different packs containing medical supplies or various types of medical supplies. FIG. 38A shows a portion of the medical supplies cabinet 1. The medical supplies cabinet 1 can be provided with a plurality of receptacles to receive and hold a number of different types of medical supplies or packs including medical supplies. As seen in FIG. 38A-38E, the portion of the medical supplies cabinet 1 includes four receptacles 91, 92, 93, 94. The receptacles 91-94 may be identical to each other in shape. The receptacles are preferably defined by a pair of opposed vertical walls 95, 96 that are spaced apart from each other. The vertical walls 95, 96 are substantially parallel to each other and extend the length of the four receptacles 91-94.

The receptacles may also be defined by a plurality of horizontal walls that extend between the vertical walls 95, 96. As shown in FIGS. 38A, 38B and 38C the receptacles may be defined by five horizontal walls 97, 98, 99, 100, 101. Walls 97 and 101 may be considered top and bottom bounding walls, and walls 98-100 are dividing walls that divide each receptacle. Each of the horizontal walls 97-101 may act as shelves to retain one or more packs that include medical supplies. The receptacles are preferably closed by a rear wall 102. The rear wall 102 extends vertically and is preferably arranged at right angles to the two vertical walls 95, 96. Preferably the portion of the cabinet includes a continuous rear wall 102 that extends across all of the receptacles 91-94. The rear wall is termed the rear wall because it is at the rear of the cabinet meaning furthest away from the user.

Each of the four receptacles 91-94 may include an optical sensing arrangement 110. The optical sensing arrangement 110 may be used to determine the type of pack within a receptacle 91-94. The optical sensing arrangement 110 comprises at least one light emitter 111 and one or more colour detectors 112 (i.e. colour sensors). The colour detectors may be any suitable optical sensors configured to detect colour. In one example the one or more colour detectors 112 may be configured to detect Red, Green and Blue (R, G, B) colours from received light. One example of an optical sensor may be the AMS TCS3472 colour detector. It should be understood any suitable optical sensor or photodetector can be used.

FIGS. 38D and 38E show an exemplary arrangement of a plurality of optical sensing arrangements, each optical sensing arrangement may be arranged within a receptacle 91-94. Each receptacle may comprise of a pair of optical sensing arrangements. As shown in FIG. 38A and FIG. 38D, each receptacle may include a pair of optical sensing arrangements 110a and 110b, and each optical sensing arrangement may include a light emitter 111 and one or more colour detectors 112. Referring to FIG. 38D, the first receptacle 91 may include a pair of optical sensing arrangements 110a, 110b. The second receptacle 92 may include optical sensing arrangement 110c, 110d. The receptacle 93 may comprise of optical sensing arrangements 110e, 110f. The receptacle 94 may include optical sensing arrangements 110g, 110h. One of the optical sensing arrangements may be positioned toward an upper end of a receptacle and the other optical sensing arrangement may be spaced away and positioned toward a lower end of the receptacle.

Each package or box of medical items (e.g. eye pads or gel pads or other medical supplies) may have a sticker with two different colour on each end. The described arrangement of the optical sensing arrangements allows such a box to be detected regardless of the orientation the box of medical items is put into a receptacle.

In one example each optical sensing arrangement may comprise a pair of light emitters 111 and a pair of colour detectors 112. These may be disposed on a single chip or integrated circuit. Preferably the sensing arrangements are located toward the front of each receptacle i.e. toward the opening of the receptacle in order to be able to detect medical items or packages that may not be pushed toward the back of the receptacle. Other arrangements to maximise detectability are contemplated.

Each optical sensing arrangement 110 may comprise a emitter and at least one colour detector formed as an IC or an PCB. In one example the optical sensing arrangements may be located only on one vertical wall, however either colour detectors or both an emitter and colour detector pair may be disposed on both vertical walls.

FIG. 38D shows a printed circuit board (PCB) 130 that is preferably substantially rectangular in shape however other shapes are also contemplated. The PCB 130 may be attached or coupled to at least one vertical wall. As shown in FIG. 38B the PCB 130 is attached or coupled to the vertical wall 96. The PCB 130 may be formed from any suitable materials.

Each receptacle 91-94 may include one or more light sensors located within the receptacle. As shown in FIG. 38C each receptacle may include five light sensors 121, 122, 123, 124 and 125. The light sensors 121-125 may be arranged as a linear array on a rear wall 102. Alternatively, the light sensors 121-125 may be arranged in any other suitable configuration such as for example a pair of rows or a rectangular configuration on the rear wall 102. The light sensors 121-125 may be configured to detect ambient light and in particular are configured to detect the intensity of the ambient light.

The optical sensing arrangement 110 and its components may be preferably in electrical communication with the processor (not shown). The processor may function as a controller and may be the same processor. The processor may operate a suitable operating system e.g. raspberry pi. The processor is configured to process signals from the light sensors 121-125 and the colour detectors 112. The processor may also be configured to control activation of the light emitter 111 based on the detected ambient light at the light sensors 121-125. The processor may also control activation of the light emitter 111 based on one or more colours detected at the colour detectors. In one example the sensors 121-125 consist of a photo-diode and trans-impedance amplifier. The output of the amplifier is saturated, such that when light is presented it is at one voltage rail and when no light is presented, the output of the amplifier routed to ground. In this manner the processor can read the signals as a digital signal.

The optical sensing arrangement 110 may be used to detect the type of pack containing medical supplies positioned in one of the receptacles 91-94. One manner of detecting the presence of a pack or packs within the receptacle is based on the level of light detected at the light sensors 121-125. The light sensors 121-125 measuring light below a light threshold (e.g. ambient light threshold) denotes that the light sensors are being covered due to the presence of a pack or packs containing medical supplies within the receptacle. The light detected by the light sensors 121-125 may be ambient light or light emitted from the cabinet e.g. from the door lighting. The presence of a pack is detected in the receptacle when the light sensors 121-125 measure a light less than a minimum light threshold.

The light detected by the light sensors 121-125 is compared to a threshold. The thresholds may include at least two thresholds a covered threshold and an uncovered threshold. The thresholds may be established by calibration measurements. In one example the contents may only be measured when the door is closed. The system may also be configured to function in real time i.e. when the door is open as well, the changes in light are only acted on if they persist.

The light emitters 110a-110h may be used to provide ambient light (when no product is present in the receptacle). The light in the door may also function as ambient light. The light sensors and the colour detectors 112 can be used in combination with each other to provide more accurate sensing and additional information. For example, the light sensors can be used to determine the number of items in a receptacle or the amount of the receptacle volume that is occupied, while the colour detectors can identify the specific product or products (i.e. medical supplies or medical items or packaged containing medical items) within the receptacle. In one example the light sensors and the colour detectors act simultaneously. Alternatively, one detecting the presence of an item or addition or removal of an item may trigger the other to activate.

Light is emitted from the light emitter 111 which may be an LED. The light emitted by the emitter 111 is preferably white light. The light emitter 111 may be activated to emit light onto a pack when the light sensors 121-125 detect light less than a light threshold, (i.e. when a pack is detected within the receptacle). The light emitter emits light that may be shone onto the pack or packs within the receptacle. The light emitter 111 may constantly emit light of a predetermined intensity. Alternatively, the light emitter 111 may be pulsed to emit pulses of light. The light emitter 111 operation is preferably controlled by the processor.

The colour detectors 112 may be used to detect a colour of the pack within the receptacle. The type of receptacle is identified based on the colour of the pack, wherein the colour of the pack may be detected based on the reflected light received at the colour detectors 112. The detected colour that is reflected from the pack preferably corresponds to the colour of the pack. The processor may include a database or a look up table or a record of the various types of packs that can be placed into a receptacle and their corresponding colour. The processor may be configured to identify the type of pack of medical supplies based on the colour of the pack based on the colour detected by the colour detectors 112.

For example, wound cleaner pack may have a red colour, an eye pad pack may have a blue colour and so on. Different packs of medical supplies may have different coloured packaging or wrapping. The colour detection of the pack allows automatic detection of the type of pack placed at a receptacle. Alternatively, each pack may include a coloured end portion. For example, the two ends of each pack may have a colour portion or a colour region that can be identified by the colour detectors 112 based on the reflected light sensed by the colour detectors. The pack may be identified based on a predetermined list that correlates colours to the type of pack containing medical supplies.

More details of an exemplary colour detection method are described below. The colour detectors 112 preferably return a red, green and blue. The colour detectors may also detect all light (clear light). Clear light is optional and coloured lights may also be used. Clear light can be used to determine the presence of an item in a receptacle and can be useful to discriminate sheen i.e. not just colour reflection but how much light is reflected. This can provide an additional measure to distinguish medical supplies from other foreign objects. The processor may access stored relationships, stored within memory, that denote the spectral reflection (i.e. sheen) of medical item packages. This allows the processor to distinguish the medical item from other items that could be placed in to the receptacle.

The processor may be configured to determine the R, G, B distance from a sample colour. The sample colour may be determined from the labels on the packs and stored in software e.g. in a database or in a look up table. A sample colour may be stored for each colour detector within a receptacle and used for calculating the distances for that detector for the detected colour. The measured sample is defined as $R_M$ $G_M$ $B_M$. The distance is calculated by the formula:

$$D^2=(R_S-R_M)^2+(G_S-G_M)^2+(B_S-B_M)^2$$

The distance is calculated for all the colours being searched for (currently red, green, blue and optionally white). The minimum distance may be dynamically set. Alternatively, the minimum distance may be predetermined. Preferably the minimum distance may be chosen as the colour is detected. $D^2$ can be used as it is monotonic, or a square root may be taken to determine D. For each receptacle two colours are preferably chosen, and tested to see if it's a valid pairing. The valid pairing is not found the receptacle is deemed occupied by a foreign object and no product is reported in the receptacle. An alert may be raised. This may be by way of the status light as herein before described.

Alternatively, it is also possible to reject (i.e. determine no pack in the receptacle) based on the value of D, generally a match is <<100, and a non-match >>100, hence by rejecting the minimums >100, rejection of foreign objects is possible. If no minimum is less than 100, we reject any match and assume a foreign object. It is possible to look at the minimum distance of valid pairs and select the most valid pair. This helps when two colours have a similar minimum distance. The values provided above are exemplary values only and can be changed depending on the type of colour detectors used, the number of light sensors or colour detectors and the type of products.

In one example initially, with no light emitted, the light intensity of the clear light emitter can be measured. If the light sensor is covered the reading at the light sensor is almost 0. If uncovered the reading is greater than 0, due to ambient light too or the door light if there is no other sunlight or artificial lights. This allows determination of which light sensors are covered. The processor is configured to activate the LEDs for only receptacles that detect the light sensors are covered.

In a further configuration the processor may detect the presence and type of a pack by using the two described methods in combination. For example, the presence of a pack may be determined based on the level of light detected by the light sensors 121-125. The amount of light detected by the light detectors may be averaged. Once the presence of a pack is detected, the light emitter may be activated to generate light. The light from the light emitter will be reflected by the coloured pack, and the reflected light will be detected by the colour detectors 112. The processor may be configured to detect the type of the pack based on the colour of the reflected light.

The type of pack of medical supplies may also be detected based on the colour of reflected light and the amount or intensity of the reflected light. For example, the type of pack may be determined based on the colour of the reflected light and if the reflected light is above a predetermined light intensity threshold. The processor may include one or more look up tables or a database stored within the processor, or accessible by the processor to determine the type of pack. The processor may also be configured to determine or identify a pack of medical supplies (i.e. a medical item) based on the intensity of light or the intensity of reflected colours i.e. based on the lux. Some packs that are matte or have a sheen reflect differently. Wavelengths of light i.e. colours also have varying reflection properties. The processor may be configured to identify the type of medical item (i.e. pack of medical supplies) based on the intensity of the reflected light or the intensity of reflected colours.

In an alternative form, the processor may be configured to control the intensity of the lights in the cabinet door, and the colour detectors 112 may be configured to detect the colour of a pack within the receptacle based on the colour of the door reflected light. For example, lights in the cabinet door may be pulsed or activated to a predetermined threshold for a period of time such that the colour detectors 112 can detect the colour of the pack. The processor may be configured to detect the type of the pack based on the colour of the reflected light.

In an alternative configuration the optical sensing arrangement comprises a single light emitter and a plurality of colour detectors. For example, in this alternative configuration a light emitter and colour detector is located near an upper end of the receptacle, and a plurality of colour detectors located at a lower end of the receptacle. The arrangement of colour detectors and the light emitter and colour detector may be switched around so that the plurality of colour detectors is positioned near the upper end of the receptacle. In a further alternative configuration each receptacle may include a single optical sensing arrangement that comprises a single light emitter and a plurality of spaced apart colour detectors. For example, a plurality e.g. 3 to 5 colour detectors may be located along one or more both of the vertical walls 95, 96.

Figure 39:
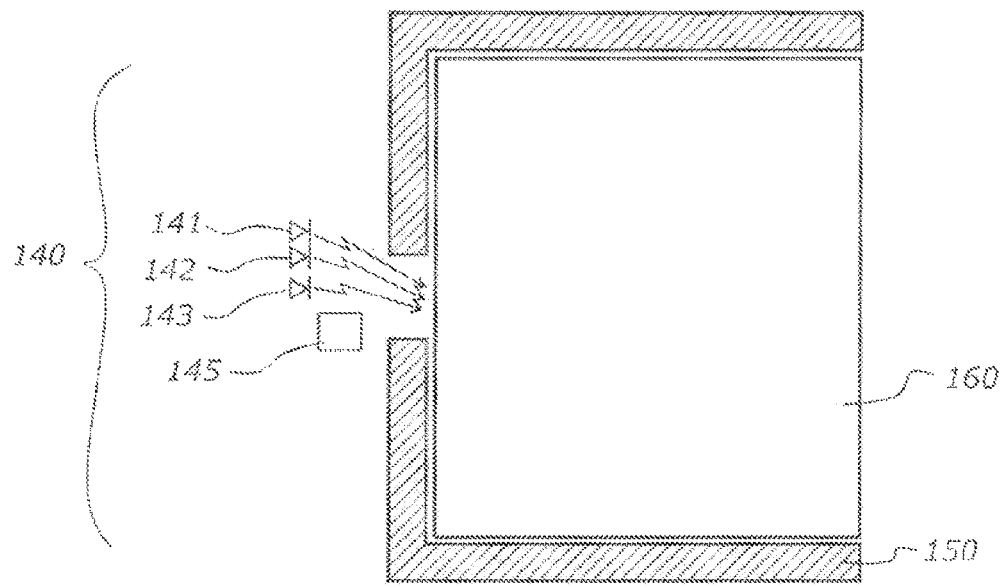
FIG. 39 shows an optical sensing arrangement that comprises a plurality of coloured light emitters and a single light detector.

FIG. 39 shows another configuration of an optical sensing arrangement 140 for a receptacle 150. The optical sensing arrangement 140 may comprise a single light sensor and a plurality of light emitters, e.g. three light emitters 141, 142, 143. The light emitters' 141-143 each have a single light sensor 145. The colour is determined using R, G and B emitters 141-143 and may also include a white light emitter. The coloured emitters 141-143 may be switched on sequentially. The light sensor 145 may be configured to detect the presence of a pack 160 containing medical supplies or a medical product in the receptacle 150. The light sensor 145 may provide light information to the processor. The processor may be configured to determine R, G and B components from the light information from the light sensor 145. The processor may be configured to use the method of measuring the R, G, B distance from a sample colour, as described earlier.

Figure 40:
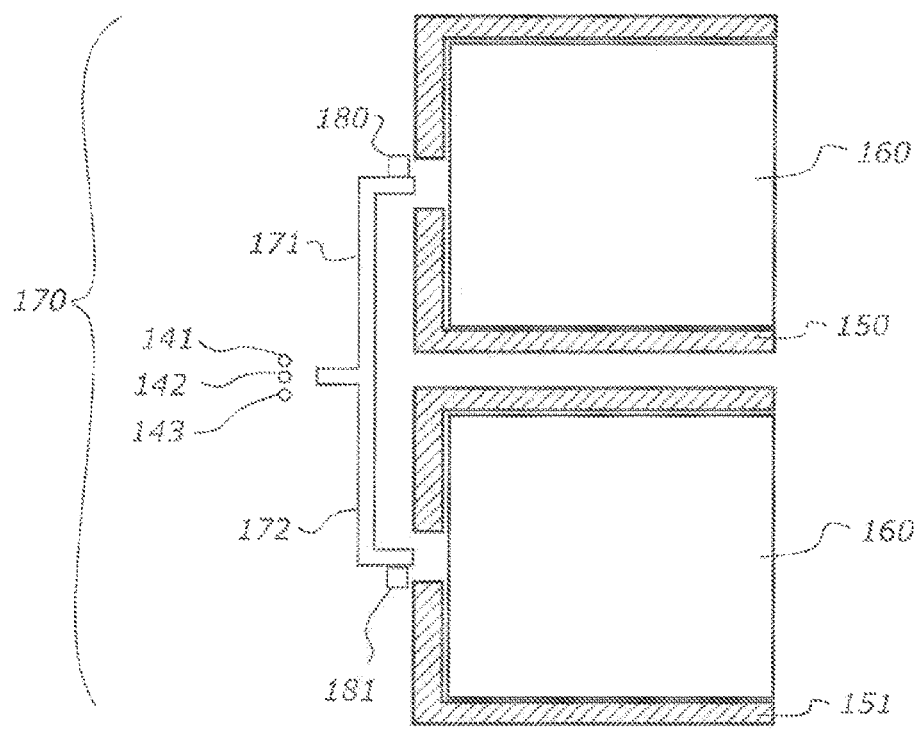
FIG. 40 shows an optical sensing arrangement including a plurality of light guides to direct light into adjacent receptacles.

FIG. 40 shows a further configuration of the optical sensing arrangement 170. The optical sensing arrangement 170 may be similar to the optical sensing arrangement 140 shown in FIG. 39, wherein the optical sensing arrangement 140 comprises three emitters 141, 142 and 143. The optical sensing arrangement 170 may include a plurality of light guides 171, 172 or pipes that configured to guide light to each receptacle. The light guides also include a central light guide 173 extending from the light emitters 141-143. Each receptacle 150, 151 may include a corresponding light sensor 180, 181. Each receptacle 150, 151 includes an opening 175, 176 for introducing of the light guides 171, 172 into each receptacle. The light sensor 180, 181 is located adjacent the opening in each receptacle. The light sensors 180, 181 may be any suitable optical sensor. The light sensors in some examples be a photodiode or photodiode and trans-impedance amplifier IC or a phototransistor or a photo resistor. The light sensors may be structured to reject infrared light which may improve sensor performance and reduce noise. The light emitters are preferably sequenced so that only a single light emitter is activated at one time. The light sensors 180, 181 may be colour sensors. In a further example it may also be possible to have light emitters that emit a series of colours the light sensors may be used to match the colour based on the intensity of the detected colour.

Figure 41:
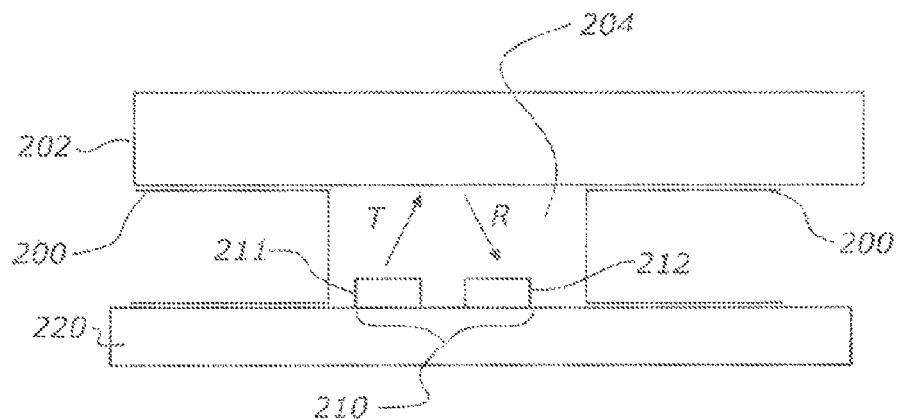
FIG. 41 shows a cross section of a receptacle with an optical sensing arrangement used to detect the presence and/or type of a pack containing medical supplies within a receptacle.

FIG. 41 shows a further configuration of an optical sensing arrangement used to detect the presence and/or type of a pack containing medical supplies within a receptacle of the cabinet of medical supplies 1. Referring to FIG. 41, there is shown a cross section of a receptacle 200. A product 202 e.g. a pack containing medical supplies is located within the receptacle 200. The receptacle 200 may include an optical sensing arrangement 210 located within the receptacle. The optical sensing arrangement 210 comprises a light emitter 211 and a light detector 212. Alternatively, a plurality of light detectors 212 may be used. The light emitter 211 may be a light emitting diode e.g. an LED. The wall of the receptacle 200 includes an opening 204 within it. The optical sensing arrangement 210 may be mounted on a PCB 220 and may be positioned to align with the opening 204 within the receptacle 200. The light emitter 211 may be configured to transmit a light to illuminate the product within the receptacle 200, as denoted by arrow T. The reflected light may be received by the light detector 212, and is denoted by arrow R.

The light detector 212 is preferably a photodiode but may be a photo-transistor or a photo resistor or any other suitable colour sensor (which includes filters and photodiodes). Photodiodes provide a cheaper construction. The light detector 212 is selected to be sensitive to a particular wavelength e.g. Infrared (IR) to allow use of ambient light. The light emitter 211 may be coded i.e. switched on and off in a predetermined sequence to allow filtering and discrimination of interference infrared IR sources. The processor may further read the light sensor output and detect the presence of the sequence in the sensed light or colour to filter noise. This could be output cross correlation to the input in order to identify the signal and filter noise.

Alternatively, the type of product e.g. pack of medical supplies in the receptacle is detected based on the colour of the reflected light, for example using the colour distance method described earlier. The light emitter 211 and the light detector 212 are preferably positioned sufficiently close enough to each other to ensure the light reflected from a product, reflects on to the light detector 212 with enough intensity such that the light detector 212 can detect the colour of the reflected light.

Figure 42A:
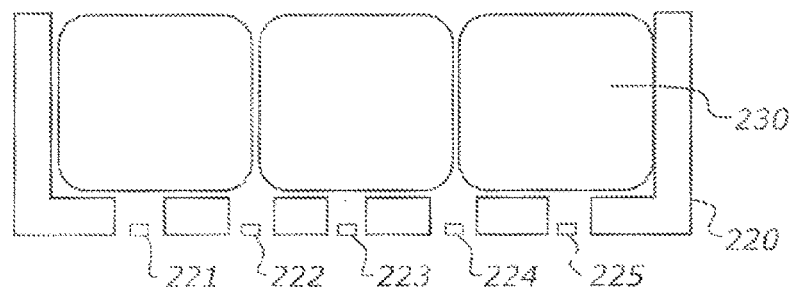
FIGS. 42a to 42c show a cross section of a receptacle including an optical sensing arrangement associated with the receptacle for detecting the number of items in a receptacle.
Figure 42B:
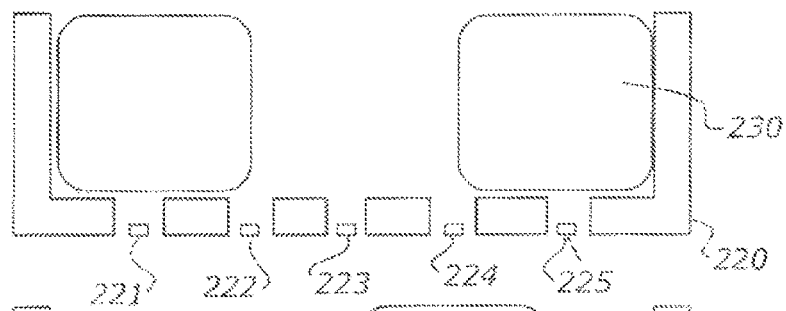
Figure 42C:
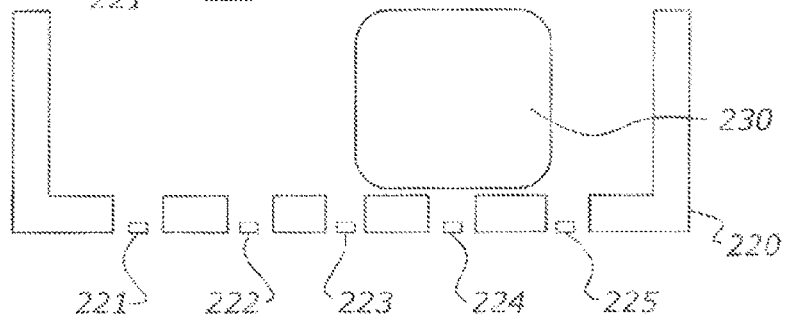

As described earlier the receptacle may include a plurality of light sensors disposed along a rear wall of the receptacle. The optical sensing arrangement and/or the light sensors can be used to determine the number of products within the receptacle. FIGS. 42a, 42b and 42c shows a cross section of a receptacle 220. The receptacle includes five light sensors 221, 222, 223, 224 and 225. The light sensors may be configured to measure ambient light or other light e.g. light from the cabinet door. The light sensors 221-225 may be configured to measure the intensity of the light, for example. The light sensors 221-225 may be arranged in a suitable configuration such that at least one light sensor is covered when a pack of medical supplies or a medical product is positioned within the receptacle 220. The arrangement of the light sensors 221-225 may be used to determine the number of products in the receptacle.

Referring to FIG. 42a there are shown three products A, B, C within the receptacle 220. As shown in FIG. 42a the products 230 may cover all the light sensors 221-225. If all the light sensors are covered this can denote the receptacle is full. The presence of products in the receptacle can be confirmed using capacitive sensing arrangements of capacitive methods described earlier. The product 230 is a product or pack that does not occupy the entire receptacle.

FIG. 42c shows a single product 230 or pack in the receptacle 220. When two or fewer adjacent light sensors are covered, the processor is configured to identify that a single pack or product is positioned in the receptacle.

FIG. 42b shows two items e.g. packs containing medical supplies are located in the receptacle 220. If two or more light sensors but less than four light sensors are covered, and in the case of just two light sensors being covered they are non-adjacent and the processor may be configured to detect the presence of two products in the receptacle 220.

Figure 43A:
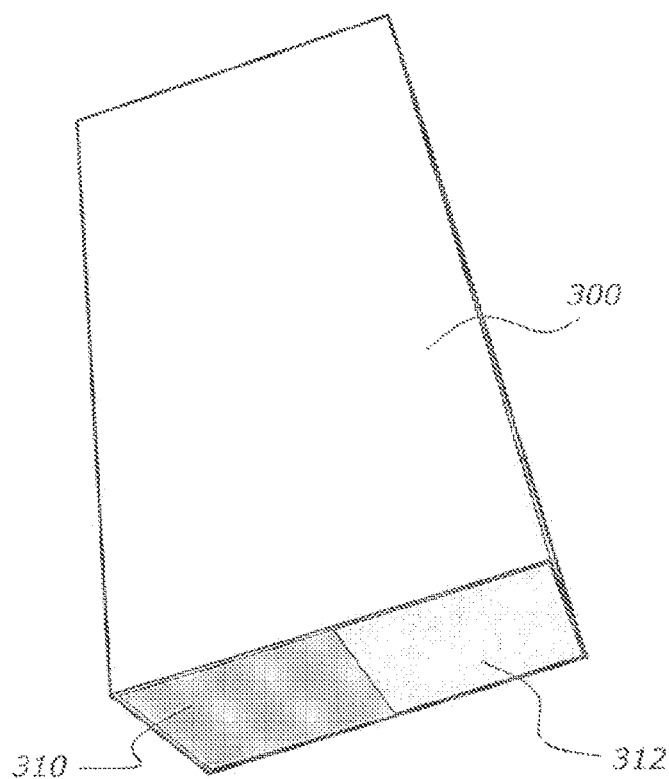
FIGS. 43A and 43B show views of an unopened package of medical supplies and an opened (or tampered) package of medical supplies.
Figure 43B:
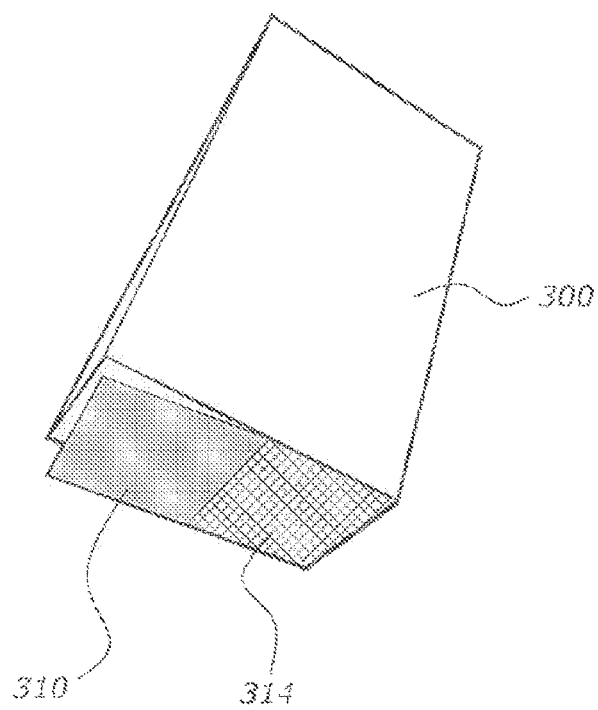

As discussed earlier optical sensing can be used for tamper detection of a pack containing medical supplies or a medical product within a receptacle. FIGS. 43a and 43b show an exemplary product 300, for example could be a box of tape or swabs or any other suitable medical product for use in the medical storage cabinet 1. The packaging of products may be such that two or more different coloured regions are located on ends of the product. The coloured regions are positioned adjacent the optical sensing arrangement 110 or 210 of the receptacle. Alternatively, the package may include a coloured strip or any other suitable shaped coloured region. The size of the coloured region should be large enough that it at least partly covers a colour detector in order to allow detection.

As shown in FIG. 43a, an outer packaging of the product includes a red 310 and a blue rectangle 312 at one end. When the outer packaging is removed the inner packaging reveals different coloured ends, as shown in FIG. 43b. As per FIG. 43b, the product has a red rectangle 310 but now includes a green rectangle 314 (denoted by the hatch lines) instead of the blue rectangle. The change in rectangle can be detected. The processor may include a list or database or table of required colours i.e. colours that should be detected when a product is placed in the receptacle. The processor may send an alarm if the required colours or required colour combination is not detected. The processor may also include a list or table or database of colours that indicate tampering. If any of the tampering colours are detected the processor may denote tampering or alarm or send a visual or audio message or send a text message or email to an administrator. In another example medical products may have a single coloured external packaging and a different coloured internal packaging. If the external colour is not detected when the product is detected in the receptacle, an alarm can be raised.

Generally, the detection of at least two colours avoids false positives. The colours are chosen not to be found in any of the other products in the medical supplies cabinet. Preferably each different type of medical item or medical pack is coloured with its own unique combination of two colours. In addition to tamper proof the proposed configuration also allows if a package has been opened. For example in a resuscitation kit, which has three items, a user (e.g. a first aider) may open it and use one and put the rest back. The system can detect that the resuscitation kit has been opened due to the change in the colours of the opened package.

In another example different batches of products have different colours to detect expiry dates. For example products from a batch having a first expiry date may be of a first colour and a batch of a second expiry date may be of a second colour.

In some configurations of the medical supplies cabinet 1, one or more receptacles 7 may include a plurality of sensing arrangements that work together to provide improved accuracy when sensing. In one example a receptacle 7 may include a combination of both an optical sensing arrangement and a capacitive sensing arrangement as described above. The optical sensing arrangement may be like any optical sensing arrangement described earlier. In one example one or more receptacles may comprise a plurality of light sensors on a rear wall, one or more colour detectors on a side wall and a light emitter to emit either white light or coloured lights. The capacitive sensing arrangement may include one or more conductive plates that may be active plates i.e. are coupled to a power source disposed within the medical supplies cabinet. The power source may be mains supply or a battery. Preferably the power source is a combination of mains power with a battery backup. The current supplied to the capacitive sensor sensing elements (i.e. the plates of the capacitive sensor) may be an alternating current.

In one example, a combination of optical sensing and capacitive sensing can be used to determine a number of packs of medical supplies in a receptacle and also detect or count the medical supplies being dispensed from the box. The light sensors on the rear wall can be used to determine the number of packs or boxes in a receptacle similar to the method described with reference to FIG. 42a-42c. The number of packs or boxes in a receptacle can be determined based on the number of light sensors that do not detect light. The detected light may be ambient light or light from the door or from another light source that shines light into the receptacle from the door toward the rear wall (i.e. toward the light sensors). Once the number of packs or boxes has been detected, the capacitive sensing arrangement can be used to detect the dispensing of items e.g. medical supplies, from the pack. The dispensing of items can be detected based on a change in capacitance due to the items being taken out of the pack. This combination of capacitive sensing and light sensing is particularly useful in in sensing the number of total packs and the number of items in each pack for a variety of medical supplies e.g. in particular for salve wipes and burn gel sachets or dressing packs. These products often come in small packs of multiple items.

Optical sensing arrangement that use colour sensing can also be used in combination with capacitive sensing arrangements to detect the type of packs or boxes of medical supplies in a receptacle and the number of items left or number of items used from each pack. The type of pack can be identified, in one example, based on the colour of the packaging or colour of the pack. The optical sensing arrangement preferably includes at least a light emitter and one or more colour detectors. The colour detectors are configured to detect the colour of the pack located in the receptacle and identify the pack based on the colour. An optical sensing arrangement and identification method similar to that described with reference to FIGS. 38A to 41 may be used to identify the type of pack or box of medical supplies. A capacitive sensing arrangement similar to that described earlier can be used to determine the number of items dispensed from each pack or box of medical supplies.

In a further form, one or more receptacles may be configured to include an optical sensing arrangement that includes colour sensors, light sensors and at least one light emitter in combination with a capacitive sensing arrangement. In this form, the processor may be configured to detect the number of packs in the receptacle based on which light sensors sense light and the type of packs based on the detected colour and the number of items dispensed from the pack using the change in dielectric constant for the capacitive sensors. In this manner all three sensing methods are used. Such a combination of sensing methods can be used in receptacles that are of a similar dimension that are configured for retaining any type of pack including medical supplies. The use of a combination of sensors for one or more receptacles allows for an improved sensing arrangement that can provide additional information such as sensing individual item usage, knowledge of total stock for replenishment and also allows for user agnostic functioning of the medical supplies cabinet i.e. is not reliant on the user placing the correct product in the correct receptacle in the correct orientation. The use of one or more of the sensing arrangements and the use of a combination of sensing arrangements is advantageous because it can help to reduce the cost of medical supplies (i.e. by keep a track of the number being used), improves workplace safety, and allows the cabinet 1 to autonomously maintain compliance with any safety standards or requirements.

The capacitive sensing can be used in combination with the colour sensing and/or light sensing described herein. In one configuration at least one (preferably multiple) receptacles may include one or more capacitive sensors and one or more light or colour/colours. Preferably at least some receptacles include the light sensors, colour detectors and one or more types of colour sensors described earlier. The capacitive sensor configuration can be like any one or more configurations described herein.

One example implementation of a receptacle that includes colour and capacitive sensing will be described. The processor is configured to receive a signal from the capacitive sensors and determine the receptacle that generates a signal indicative of a high capacitance i.e. wherein the capacitance exceeds a threshold. For example this can be due to placing gel pads in a gel pad receptacle. The light intensity in the receptacle is determined from the output of the colour detectors e.g. colour detectors 112, when the LEDs 111 are off. If the detected light intensity is less than a threshold i.e. denoting a product is within the receptacle, the LEDs 111 may be switched on. The readings from the colour detectors 112 or the light sensors 121-125 may be measured. The sensor readings may be multiplexed to reduce power draw. The colour of the package may be identified based on the RGB distance described earlier. The colour can of the item in the receptacle can be detected for each colour detector in the receptacle. The colour detected by the pair of colour detectors for the receptacle is compared to a list of known colour pairs or known colours e.g. a database of colours to identify a match. The type of product (i.e. product identity) is determined based on the colour match. The capacitive sensors can then be used to determine if the medical product i.e. medical item is removed from the receptacle or another one is added. Further the capacitive sensor arrangement may be used to determine each individual item used if a pack of items is identified based on the colour sensing.

The capacitive sensing and colour sensing provide complementary benefits in automatically identifying the presence of an item within a receptacle, identifying the type of item and then identifying (i.e. tracking) if the item is removed or a new item is added or the consumption of specific items. The detection of a product by capacitive sensing may trigger the colour sensing. Similarly, if a product is detected based on the light sensors, the capacitive sensing and colour sensing may be triggered. The use of a combination of colour and capacitive sensing allows for a wide variety of products to be automatically detected. Further the use of both sensing mechanisms allows for automatic identification of the type of product, the number of products and the consumption of products. This helps to automate the stock-take process as well as helps to automatically manage stock within the medical supplies cabinet.

Figure 44:
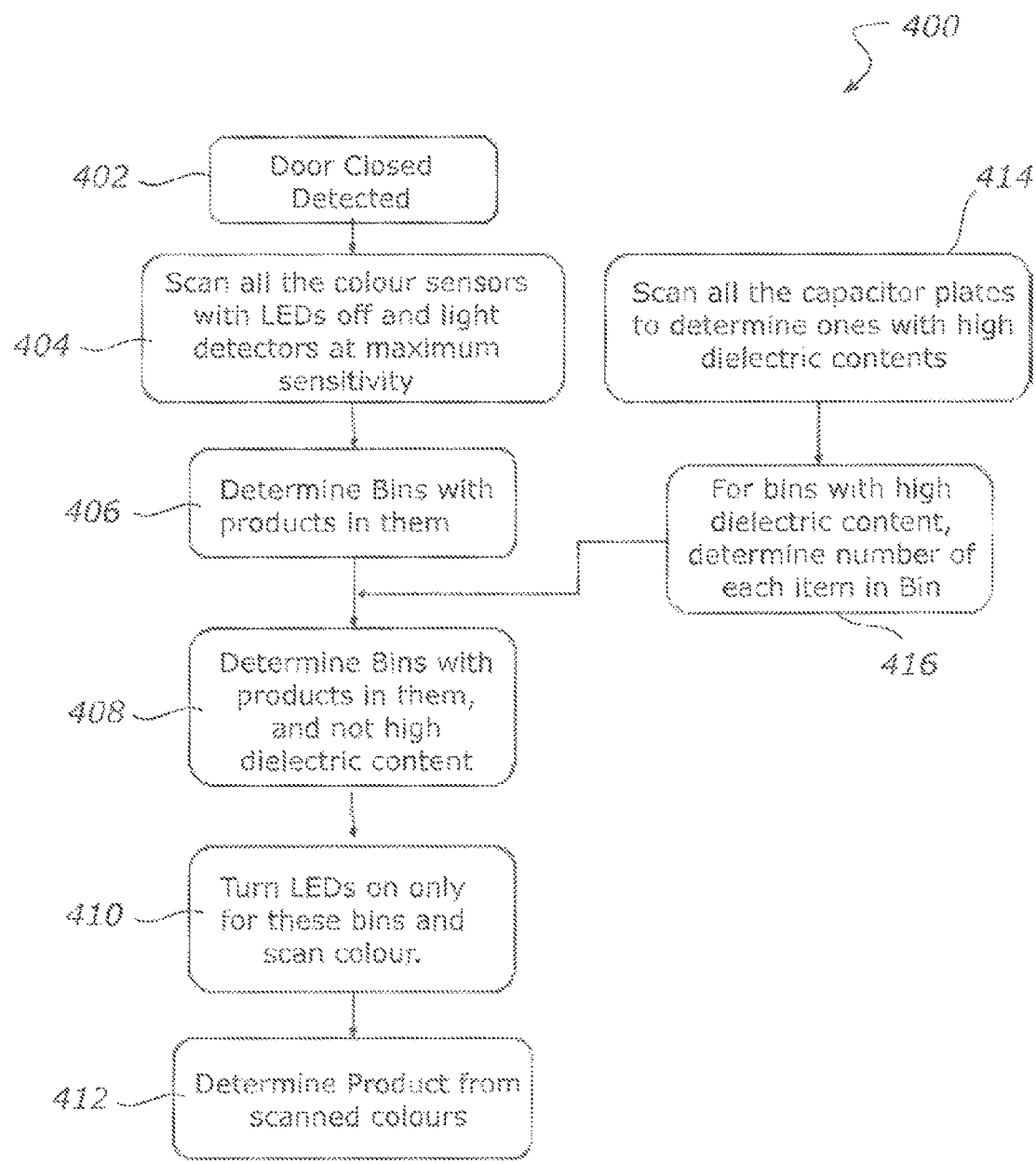
FIG. 44 shows a method of using colour detection to determine the type of pack or product in a receptacle.
Figure 45:
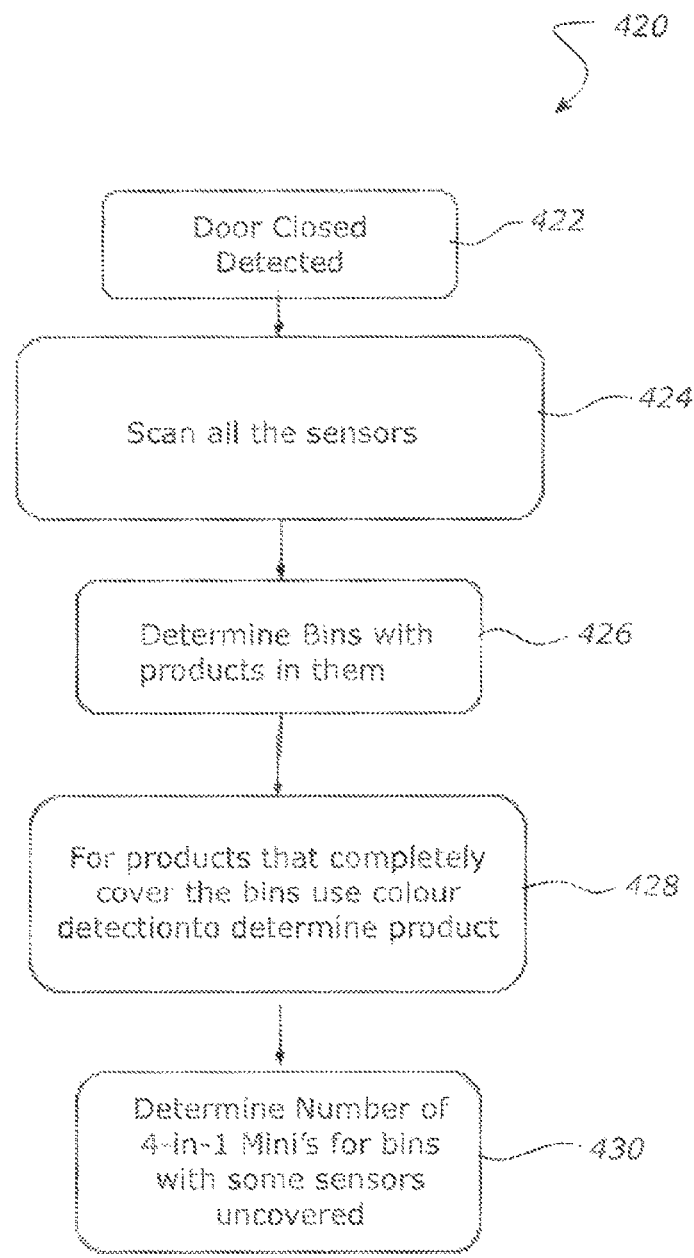
FIG. 45 shows a method of determining the number of products in a receptacle using one or more light sensors within the receptacles.

FIGS. 44 and 45 show methods of colour detection. FIG. 44 shows a method 400 of using colour detection to determine the type of pack or product in a receptacle. The method may be implemented by a processor of the cabinet 1. The method commences at step 402. At step 402 a door closure is detected. Once the door is detected as closed, the method may proceed to step 404. Step 404 may comprise scanning the colour detectors e.g. 112, 212. Step 406 the processor may be configured to determine the receptacles with products located within them. Step 408 comprises determining the receptacles that include products within them, for the receptacles that do not have a high dielectric i.e. wherein the dielectric does not exceed a threshold. The presence of a product can be determined based on the reading from the plurality of light sensors. Step 410 comprises switching on the light emitters 111 or 211 on in the receptacles within which have products detected within them to scan colour. Step 412 may comprise determining the type of product within a receptacle based on the colour detected by the colour detectors 112, 212. The detection of colour can be by the method described earlier.

The method 400 may optionally include additional steps 414 and 416. Step 414 comprises scanning the capacitor sensors i.e. capacitive sensing plates to determine the ones with high dielectric constants. The processor is configured to perform this scan regularly at any suitable sampling frequency. Preferably this scan is conducted every few seconds or milliseconds such that the processor can detect any changes in the receptacles quickly and respond appropriately. For example, this is useful in detecting the number of wipes used when the door to the medical supplies cabinet is opened.

Step 416 comprises the processor determining the number of each item in a receptacle for the receptacles that are detected with a high dielectric. The number of items in a receptacle may be identified based on the number of light sensors that are covered, as described earlier with respect to FIG. 42a-42c. Alternatively another suitable capacitive or optical method may be used. This combination of capacitive and light and/or colour sensing provides for an improved medical supplies cabinet 1.

For some receptacles, only capacitive sensing arrangements may be used. For other receptacles, only colour sensing arrangements may be used. For some additional receptacles, both the colour and capacitive sensing arrangements are required to be used. The use of the sensors can be tailored depending on the type of medical products i.e. medical items being used in the medical supplies cabinet.

The use of both capacitive in combination with colour sensing, may allow for a reduced number of colour sensors to be used. This can provide cost savings, provide more accurate detection of medical items and reduce the number of different colour combinations required.

FIG. 45 shows a method 420 of determining the number of products in a receptacle using one or more light sensors within the receptacles. FIG. 44 may be implemented by the processor of the cabinet 1. The method commences at step 422. Step 422 comprises detecting a door of the cabinet being closed using a suitable door closure sensing method e.g. a capacitive sensing method. Step 424 comprises scanning all the sensors in the cabinet. Step 426 comprises determining the receptacles that include products within them using either the light detectors or capacitive sensors or a combination thereof. Step 428 comprises using the colour detection method for products that completely occupy the space within a receptacle. The colour detection method may be the one described earlier e.g. with reference to FIG. 44. Step 430 comprises determining the number of products within the receptacle using a light detectors on the rear wall, as described earlier e.g. with reference to FIGS. 42a to 42c.

The methods described in FIGS. 44 and 45 are preferably stored as computer readable and executable instructions with the memory unit associated with the processor. The processor is configured to read the instructions and execute at least one of the methods described with reference to FIGS. 44 and 45. The method 420, shown in FIG. 45, is an alternative method to method 400 shown in FIG. 44.

Colour detection is included as a means to detect the particular type of product i.e. identify the medical item or medical product placed into a receptacle, when the receptacle includes a product within it. The colour sensing helps to identify the number and identity of the product (i.e. medical item). For example, if 3 of the light sensors are covered in a receptacle, the colour sensing can help distinguish if there are 3 small items or one large item based on the colour detection.

The capacitive sensor(s) and optical sensing arrangements are also advantageous because they provide a contactless sensing mechanism to sense medical items in the cabinet. The sensors allow automation of sensing items within the cabinet. Further at least the capacitive sensor(s) and the optical sensing arrangements are tailored for sensing medical items.

The medical supplies cabinet may include one or more environmental sensors associated with the medical supplies cabinet. The environmental sensors are configured to detect one or more environmental parameters to provide an indication of the environmental condition within the local environment of where the medical supplies cabinet is used. The environmental sensors may be any one or more of temperature, humidity, CO2 or other gases sensors. Preferably at least a temperature and humidity sensor are used with medical supplies cabinet in order to detect temperature and humidity levels. The processor is configured to process the signals from the environmental sensors and may generate an alarm or alert or provide a message to an appropriate person (e.g. a health and safety officer) if the measured temperature or humidity exceeds an upper threshold or drops below a lower threshold. The use of the environmental sensors can allow a user to determine conditions e.g. working conditions if the medical supplies cabinet is used in an office or restaurant or other place. The information from the environmental sensors can also allow an assessment of comfort levels e.g. for staff within a work environment. The output from the environmental sensors may also be processed by the processor to determine the type of medical supplies that may need to be stocked in the medical supplies cabinet. For example for high temperature environments additional burn gels or other such products may be needed to be stocked. The environment sensor data may also be processed to determine if any environmental changes need to be made for example switch on air conditioning or increase heating in order for comfort.

One or more components and functions illustrated in the figures may be re-arranged and/or combined into a single component or embodied in several components without departing from the scope of the invention. Additional elements or components may also be added without departing from the scope of the invention. Various combinations of the described sensors or sensing arrangements herein are also contemplated. Additionally, features described herein may be implemented in software, hardware and/or a combination thereof. The processor as described may include a combination of hardware, software and firmware modules. The processor and its associated components may be implemented or performed by a general-purpose processor, a digital signal processor, an application specific integrated circuit (ASIC), a field programmable gate array (FPGA) or other programmable logic components, discrete gates or transistor logic, discrete hardware components or any combination thereof design to perform the functions or methods described herein. The memory unit may be any suitable storage memory e.g. read only memory, random access memory, magnetic disk storage mediums, optical storage mediums, flash memory or other machine non transitory machine readable mediums.

In addition to and/or alternative to using capacitive sensing for the presence and/or consumption levels of stock in a receptacle, Electronic Identification (EID) sensing of packs may occur. EID (such as by way of RFID tags) that may be incorporated with packs can allow for pack information, location and/or orientation to be determined using an EID sensor/reader or readers. Such sensors are preferably incorporated as part of the medical supplies cabinet of the present invention and/or may be a reader or readers used remote from the cabinet such as a handheld RFID reader.

Figure 47:
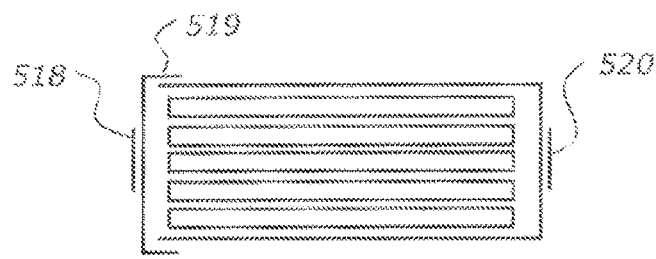
FIG. 47 is a cross sectional view through a package.
Figure 53:
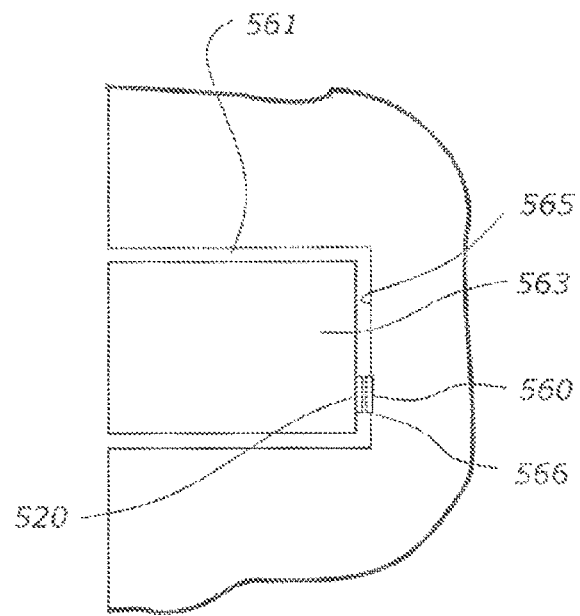
FIG. 53 is a cross sectional view through a receptacle showing a package located in the receptacle.

RFID tags may be placed or located on/in packs to detect the presence of the pack in a receptacle of the cabinet. Other information may also be sensed such as information about the product contained in the pack such as expiry date related information that may be loaded on or able to be decoded from the RFID. The RFID tag 520 may be located on a wall of the pack such as seen in FIG. 47. It may be located on the back of a pack 563 so that when the pack is loaded into a receptacle, the RFID tag 520 is proximate an RFID reader 560 of the receptacle 561 as seen in FIG. 53. The tags are preferably passive, in that they are excited by the reader, and then transmit back to the reader.

The RFID sensor 560 may be located on a forward-facing wall 565 within the receptacle 561. It may be possible to use one RFID reader for all receptacles of the cabinet that may receive an RFID tag carrying pack. It may be desirable to use multiple RFID readers, preferable one for each pack to be read. It is desirable to reduce the number of readers of the cabinet to help cost. It may hence be possible to use one reader and to utilise multiplexing between many antennas.

In a situation where packs are placed in an incorrect receptacle or other location in the cabinet, be it by mistake or on purpose, EID may be used to detect this. The use of EID can help the cabinet to distinguish between packs. This can be important as it may not be reasonable to expect users of the kit to adhere to operating instructions and place the correct packs in specific positions in the cabinet.

To help detect the correct pack being loaded and/or positioned in the correct location of the cabinet, in one example, RFID tags may be placed on or otherwise incorporated with the pack. The RFID tag may indicate product related information, and in particular the type of product carried in/by the pack. Other information such as expiry date related information may also be carried or otherwise readable from the tag. The product related information may be information of the product stored by the tag or it may be a code or sensable signal of the tag that is relatable to product information stored on a remote database such as on an EID reader and/or central database that the cabinet is able to communicate with. An EID reader such as an RFID reader of the housing of the cabinet may be used to read product information off the tag's unique ID.

The EID sensor may be comprised of a reader antenna 566. The reader antenna may be located in a receptacle of the cabinet whereas other parts of the sensor may be located remote from the receptacle but preferably still with and within the cabinet.

It is envisaged that for a single cabinet, multiple reader antennas 566a-d may be used for one reader 560. This can help reduce cost. This can be seen in FIG. 54. This can allow for one reader to connect to multiple reader antennas such as one for each of a plurality of receptacles 561a-d of the cabinet. The connection of multiple reader antennas as part of the reader may be by antennas in parallel, or via a switch. An antenna of a multiple antenna system may be used to focus on one receptacle only to sense for a pack or a plurality of packs in or being loaded into that receptacle.

As an example, one reader may be used where the location sensing of a pack is not that important. As a further example a reader could be used per receptacle which may receive multiple tags.

As a further example, one reader may be used per pack where the order of packs is important, i.e. wound cleanser, or plasters, where the bottom packet is being emptied and it's desirable to know how empty it is.

For example, one reader may be used to cycle over up to 16 antennas. Such cycling may not be in order, or not all antennas are cycled through every cycle. For example, when the door of the cabinet is open, the system may cycle through the antennas where we need to know the order of the boxes, e.g. wound cleaners, sanitary wipes, burn-gel sachet, and plasters. By cycling through these is may be possible to detect when a box is added and removed and work out the order. When the door is closed we look at the other boxes to detect changes, then go silent with sensing until the door opens again.

In one form the EID system herein described may be used to sense pack orientation. This may be by way of sensing for correct orientation and/or incorrect orientation. If correct and/or incorrect orientation is detected by the EID system, an alarm or notification may be made. This may be made at the cabinet itself or to e remote device (e.g. a mobile phone that the person loading the device may have), visible or audible to the person loading the cabinet, so that they can be made to realise of incorrect and/or correct loading. The notification may also be digitally recorded at the cabinet and/or transmitted/reported remote of the cabinet, such as to a central server.

Figure 54:
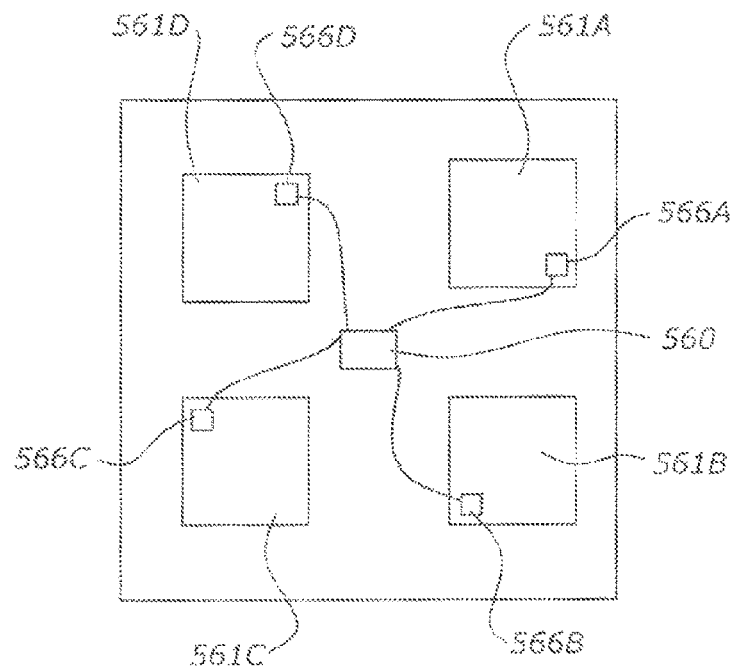
FIG. 54 is a front view of a cabinet showing for receptacles.

For example, and as seen in FIG. 54 a receptacle 561b may have a reader antenna located at the bottom left corner of the receptacle, when looking into the receptacle. A pack to be received in receptacle may have an RFID tag located at the bottom right corner of the back face of the pack. When the pack is loaded into the receptacle correctly the RFID tag and reader antenna end up being positioned adjacent each other and the RFID reading can be made. This can then indicate a loading of a pack in the correct orientation (such as by sounding a confirmatory message or a showing of a green light) and the RFID tag may also optionally have information/signal read by the reader or for confirmation that the correct pack has been loaded into the receptacle. Whilst in some forms the antenna/reader for a receptacle may be able to sense tags in locations less proximal to the location of a tag of a pack in the correct orientation, the sensor can distinguish between a correctly oriented pack and incorrectly oriented back due to sensed signal strength. A pack correctly oriented may have a much stronger sensed signal strength due to closer proximity of the tag and the antenna than an incorrectly oriented pack.

To determine incorrect loading orientation of the correct and/or the pack being incorrect pack, the receptacle may use additional EID reader antenna positioned in the receptacle and/or a capacitive sensor as herein described.

1. Where a capacitive sensor is used, the sensor may detect that an object has been inserted into the receptacle. If the EID tag is not also able to be read by the reader antenna, because of incorrect loading orientation of the pack, then there may be an indication of a loading of the pack in an incorrect orientation (such as by sounding a negative message or a showing of a red light). This may then result in the person reloading the pack a different orientation and potentially/eventually in the correct orientation. If the pack is the incorrect pack, the EID tag may never be sensed (if there even is an EID tag on the product) or the EID tag may be sensed and read as being of the incorrect product and/or lapsed expiry date.

2. Where additional EID antennas 566E and 566F are used in a receptacle 561E, as see in FIG. 55, a pack 563 E can have EID tags in different locations to detect correct or incorrect loading. A first EID tag 520 E may be positioned at the top centre and another EID tag 520F at the bottom centre, as shown in FIG. 56.

It is envisaged that the received signal strength from multiple antennas can be used to triangulate where a product is in the cabinet.

Figure 57:
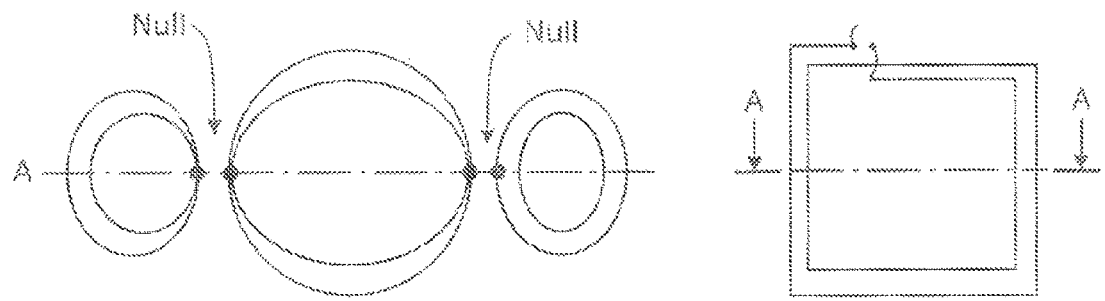
FIG. 57 is a view of an RFID antenna and field.
Figure 57A:
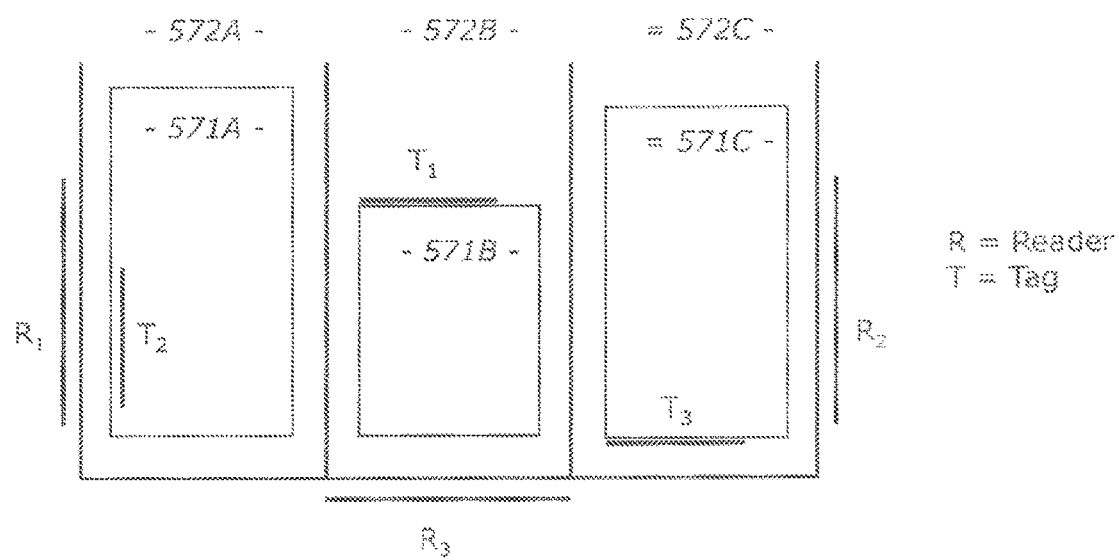
FIG. 57A is a view of 3 receptacles (Bins) and positioning of the reader antenna compared to RFID tags.
Figure 58:
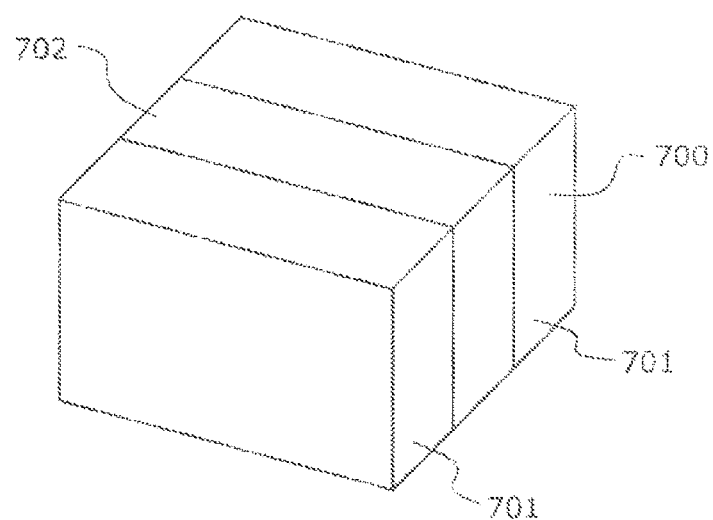
FIG. 58 is a perspective view of a package.

For example, with reference to FIG. 57A. Three readers R1, R2, R3 can all receive signals from tags T1, T2, T3 with differing strengths, ie R1 and T2 have a strong coupling and R2 and T2 have a weak coupling. By utilising pre-measured coupling strengths and performing a best fit of actual strengths sensed, the position of the tags T1, T2 and T3 can be uniquely estimated. This figure shows three products occupying three bins, but it can be appreciated there may be multiple products in each bin.

FIG. 57B shows a cross section of a reader antenna.

To aid in correct pack loading and optionally also with correct orientation loading, colour(s) on the pack can be used for matching to colour(s) of the receptacle or at a receptacle entrance.

Figure 55:
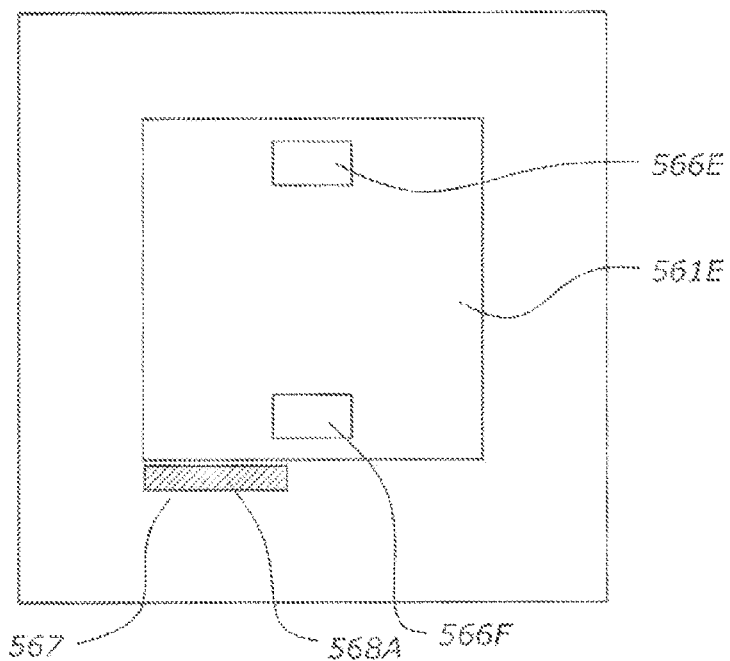
FIG. 55 is a front view of a receptacle of a cabinet.
Figure 56:
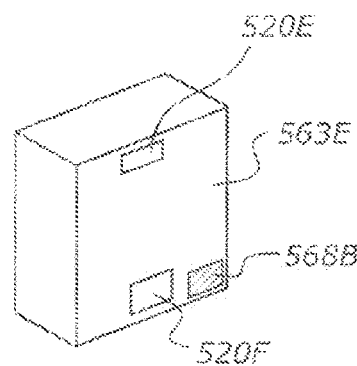
FIG. 56 is a rear perspective view of a package.

The packs and the cabinet's faceplate 567 surrounding a pack or packs in a receptacle 561 can be colour (568A/B) matched as see in FIGS. 55 and 56. For example an eye wash pack may be generally of a blue colour or include a region that is blue (e.g. its back side). The receptacle and/or receptacle entrance that the eyewash pack is to be loaded into may also be coloured the same. A pack may have a coloured region 568B at a particular portion that may correspond to a matching colour 568A at a particular portion of the receptacle or receptacle entrance. This can help identify not just which receptacle the pack is to be loaded into but also the correct orientation by virtue of the two portions needing to be aligned when loading the pack in. For example, a back face of a box shaped pack, may have a yellow colour along its base line. The receptacle to receive the box shaped pack may have a yellow strip along the bottom of the entrance opening or the bottom face of the receptacle itself. This colour matching will help identify where packaging should be loaded. This can help improve time to identify product based on colour coding. It may create a visible indication of product in incorrect location. This may be tied with the additional EID sensing herein described, to electronically sense that product is in the correct location. I.e. the colour matching is to aid the user get the product into the right receptacle and/or the right orientation. EID sensing is provided to verify and/or notify of correct or incorrect loading.

The present invention can also allow for a sensing of used packs distinct from unused packs. This may be achieved by the use of EID, colour region or capacitive sensing or a combination of such.

Detecting when a pack has been tampered/opened within the cabinet can be desirable. Detecting whether a pack has been tampered/opened with can also be desirable. If for example a user takes a pack out of the cabinet and then re-inserts the pack, there is a risk that the pack may have been altered (e.g. the content of the pack has changed or sterility of the pack has been affected. It is desirable for the cabinet to identify this condition change and report it so that there is an ability for it be remedied.

Figure 46:
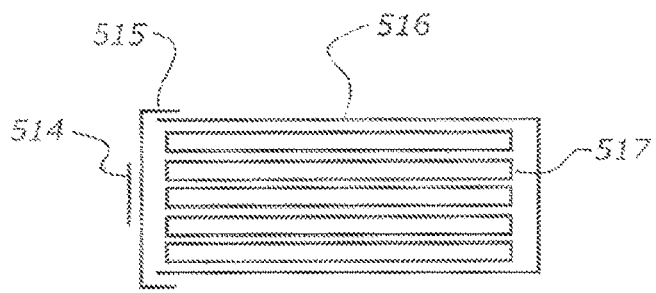
FIG. 46 is a cross sectional view through a package.

As can be seen in FIG. 46, a sensor 514 is attached to a removable or openable cover 515 that covers an opening of a pack 516 that contains product 517. Then the cover 515 is removed from the pack to allow access to the product 517, the sensor is also removed from the pack.

The sensor's removal can be detected by the cabinet or remote from the cabinet by a reader. The sensor may for example be an RFID tag and an RFID reader of the cabinet can be used to detect of the tag is present or not on a pack that is loaded into a receptacle of the cabinet.

Figure 48:
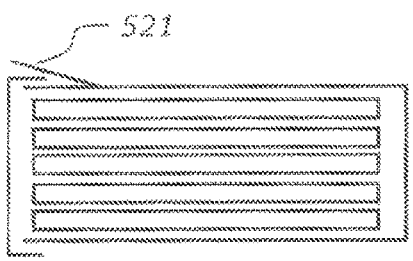
FIG. 48 is a cross sectional view through a package.
Figure 49:
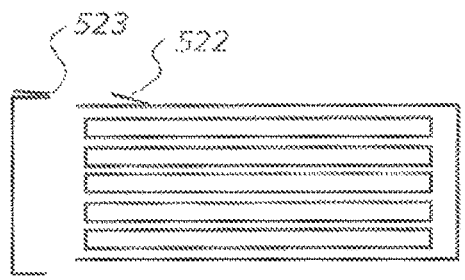
FIG. 49 a cross sectional view through a package with the tamper evident device broken.

In another embodiment as seen in FIGS. 48 and 49, a sensor 521 may be used that is partially attached to the cover of the pack and partially to the body of the pack. When the cover of the pack is removed as seen in FIG. 49, the sensor is damaged and/or split into two parts 523,522. This change in condition of the sensor is able to be detected by a sensor reader (ie it may be a different reading to a reading taken if the sensor was intact) of the cabinet so help indicate that the pack has been opened.

Examples of a cover 515 that may be used to could be a sticker, wrap, and a rip removable tab built into the package.

As can be seen in FIG. 47, two RFID tags may be used on a pack, one of the body and one on the cover. RFID tag 518 may get removed or damaged when the cover is removed/opened to determine if the pack has been tampered with or opened and the other RFID 220 remains on package so cabinet can identify what the pack is, as earlier described.

The system may use a database which knows that tags 518 and 520 are or should be, on the pack to be loaded into the correct receptacle of the cabinet.

Figure 59:
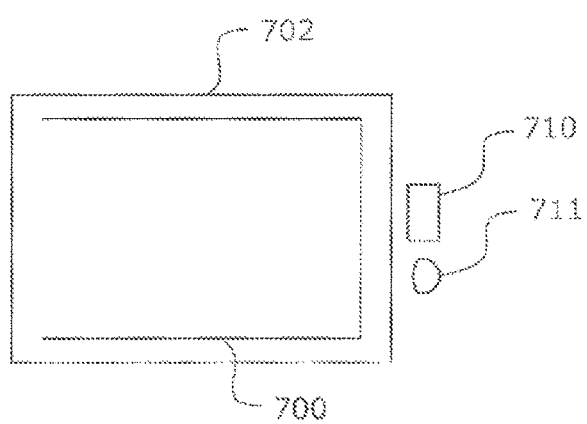
FIG. 59 is a plan view of a receptacle.

The cover 702 over the opening of the box 700 may in addition or alternatively have two or more different colours over a sensor (such as sensor 710 of FIG. 59). For example, the cover strip 702 may be a different colour to the box 700 surface, allowing the detection of packaging that has been opened or tampered with. The strip 702 may be white whereas the box may be green. When the white strip 702 is removed the colour detector 710 can detect green (701) rather than white. A light source 711 may be provided to assist in colour detection.

Figure 60:
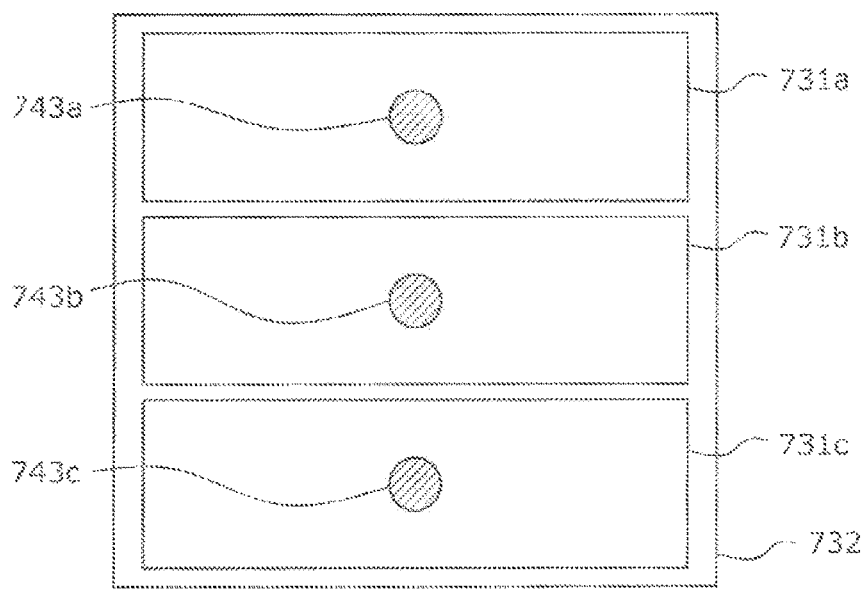
FIG. 60 is a front view of a plurality of receptacles.
Figure 61:
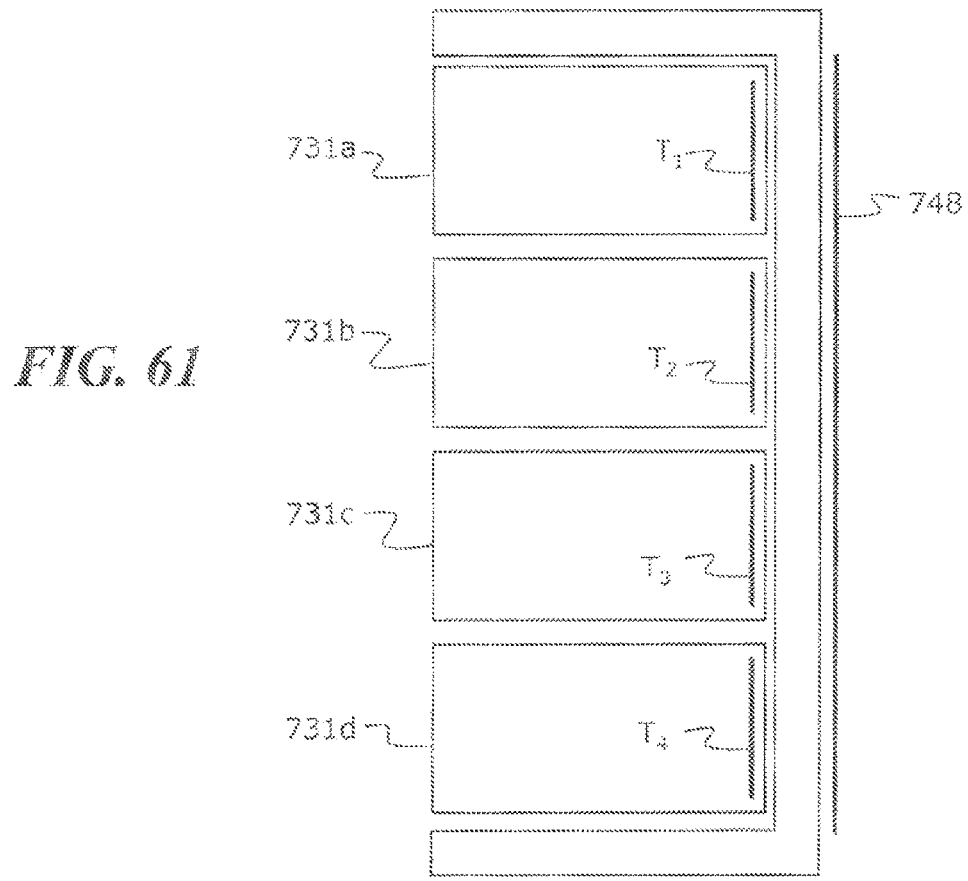
FIG. 61 is a side view of a plurality of receptacles.

It is also envisaged that different batches of boxes may be made to have different colours to detect expiry dates of the packs. FIG. 60 shows a receptacle 732 with three boxes of product 731a, 731b, 731c stacked in it. Coloured dots 743a, 743b, 743c indicate an expiry period, is say two years' time. When it is time to send out new products a different colour is on the box. The customer can remove and dispose of old boxes and see that the ones loaded are the correct non-expired colour. FIG. 61 is a side cross sectional view of a receptacle with 4 packages loaded 731a-d, each having its own RFID tag T1-4 each able to present to an antenna 748 of a reader.

Figure 50:
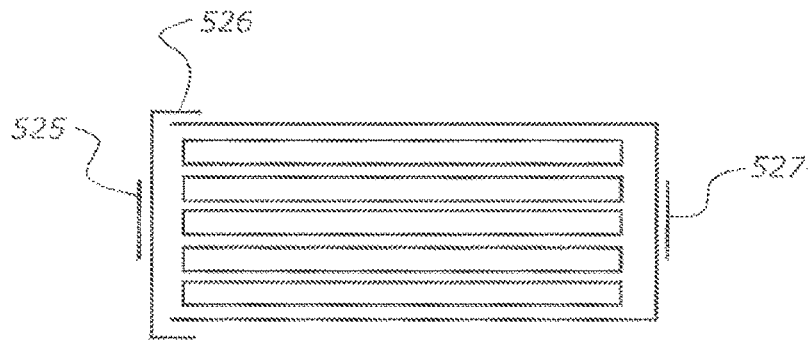
FIG. 50 a cross sectional view through a package.
Figure 51:
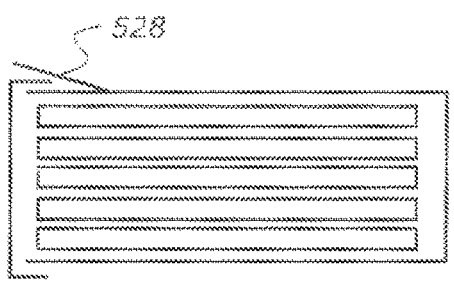
FIG. 51 a cross sectional view through a package.
Figure 52:
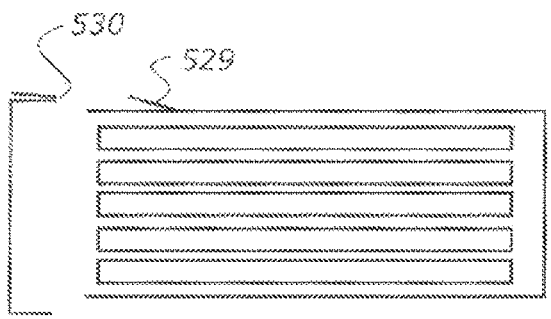
FIG. 52 a cross sectional view through a package with the tamper evident device broken.

In another arrangement as seen in FIGS. 50-52, the cover 526 over/at the opening of the pack may have a capacitive pad. Indeed, two capacitive pads may be provided on the one pack. One capacitive pad 525 is able to be removed or damaged when cover 526 is removed to determine if the pack has been tampered with or opened and the other capacitive pad 527 remains on pack so that the cabinet can identify what the package is.

Where one capacitive pad 528 only is on the pack it may be applied to the cover in a manner so that when the cover is removed to gain access to product a section of capacitive pad 530 is removed resulting in the sensor getting a different reading from the remaining capacitive pad 529.

The cabinet is able to be design, configured and manufactured for a set of products. It is realised that over time, suppliers of products may make product changes such a changes to the shape of their packs. Likewise new health and safety regulations may mean that different or additional product may need to be carried by the cabinet. Such changes may require the reconfiguration of the cabinet as well as reprogramming of the system. To facilitate this, the receptacles of the cabinet may be arranged as module(s) that clip in and clip out. New modules may be supplied to end users as and when required and may then be able to be replaced on site. The end user may use a supplied tool to release the clips, and can then remove the module(s), and replace the old ones with new module(s). A software/firmware upgrade can be conducted remotely or alternatively the new modules may come with antenna and/or capacitive sensors configured appropriately to allow the new modules to plug and play.

It is envisaged that the arrangement, instead of using electrical connectors, a or each module may be powered inductively and communication may be wireless to a central processor such a master microcontroller of the cabinet. The wireless communication may be over the inductive link, or use other common wireless methods, such as bluetooth or near-field-communications. Wireless powering and communications allows the communications and power needs of the module to be flexible and future proofed.

In one arrangement the receptacles may contain a RFID sensor for detecting products, and this reader can emulate a RFID tag, the connection to the main cabinet is made by periodically putting the modules reader in emulation mode and a second reader on the main cabinet reads the modules data. This may be helpful for modularity of the cabinet where we need an RFID that is not physically attached to the main electronics (it's only useful where the module is powered somehow). The non-attached RFID reader could be on a module in the cabinet or very close to the cabinet. For example, dispenser may be added and this may be achieved via Bluetooth or a RFID reader just adjacent to the main cabinet. Using RFID readers in main reduces cost (eg of Bluetooth). A further example may arise where a complex module in provided in the cabinet. To help future proof it, a wireless connection may be established so that when it reconfigures it does not expose any electrical connections making module swap easily done by unskilled people. This also gives flexibility in design as connections do not have to be exact.

In a further aspect the at least the cabinet body front outline and door are preferably symmetrical such that by rotating the cabinet about a horizontal axis by 180 degrees, a left or right opening door can be achieved.

As described above with reference to FIG. 3A, the cabinet system may include only one door. A two door cabinet system such as the one shown in FIGS. 1-3 may require two cameras given that a user may be to one side of the door and easily be missed in the photo. Utilising one door cabinet system that opens sideways and only by a certain angle (e.g. 150 degrees) reduces the risk of missing a photo of a user being taken. In a preferred form, on opening of the door, a series of photos are preferably taken. The photo chosen to report from the series, can be chosen by:

(a) facial recognition to choose a photo that captures the person(s) best and maybe compresses the photo based on where the faces are. Identifies the person(s) using the kit and adds this information to the reports, or (b) timed to be between the door starting to open and fully open. This may help avoid the situation where a user only slowly opens the door and a fixed time camera gets the door in the photo, or the user is familiar with the cabinet and rapidly takes the product before a photo can be taken.

An unbreakable power supply may be built into cabinet to help the cabinet stay alive in a power-off situation with intelligence that turns lights off incrementally to make power last longer.

Cyber security is important to stop a cabinet being utilised for nefarious purposes. To help combat this the software may use standard prevention techniques. To aid security knowing the kit has been opened allows the system to detect an attack and the kit can be isolated or cleaned of any unwanted software.

Another preferred feature of the present invention, to address that some items in a compartment, such as eyepads, gauze wipes, and dressings, may not have inherent physical parameters that can be accurately sensed with high reliability, is to have one or more RFIDs on each item. Multiple RFIDs can be sensed by one antenna, so that several of these items can be placed in one compartment, giving a cost advantage. By careful arrangement of the RFID tags on each item, the possibility of two RFID tags cancelling each other is reduced.

Figure 70A:
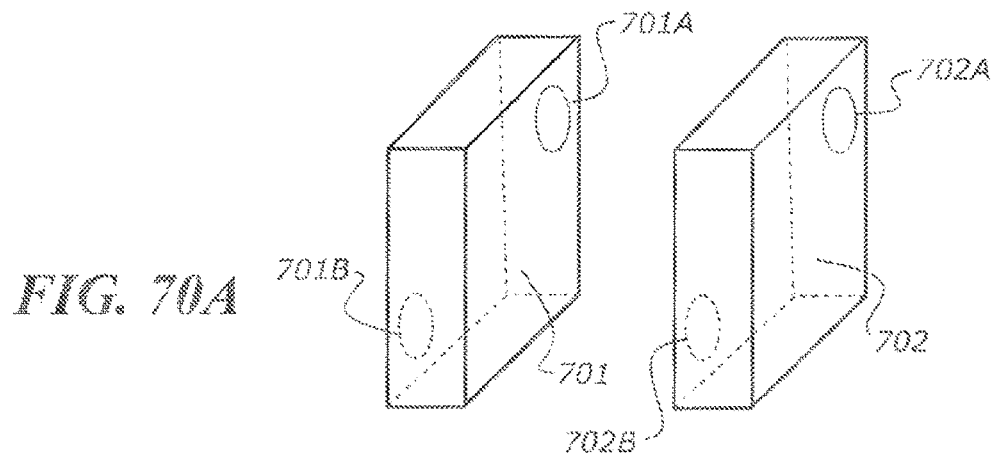
FIGS. 70 A-C show two products such as packs for a triangular bandage each having two RFID tags.
Figure 70B:
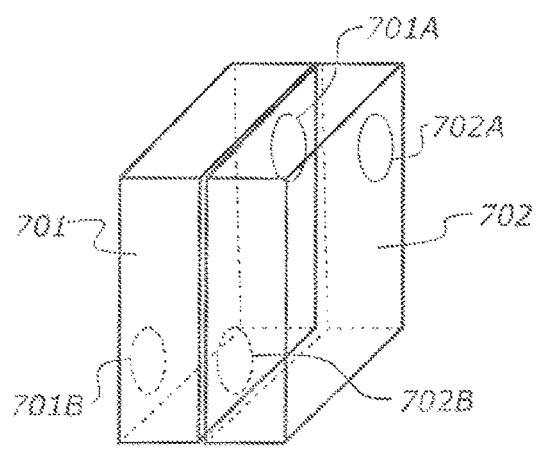
Figure 70C:
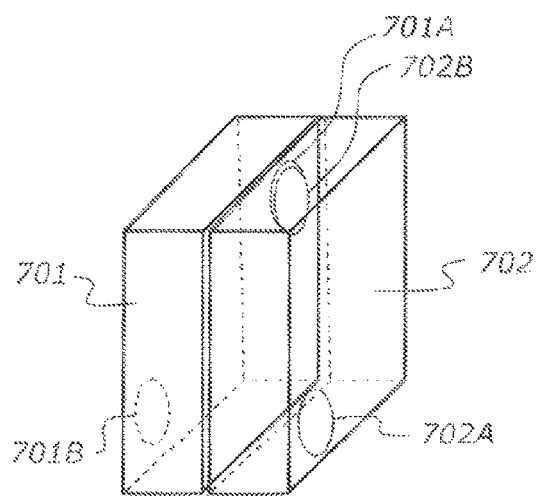

FIGS. 70A-C show two products (701, 702) such as packs for a triangular bandage each having two RFID tags. The first product 701 has two RFID tags 701A, 701B and the second product 702 has two RFID tags 702A, 702B. When the products 701, 702 are placed in one compartment in the orientation as shown in FIG. 70B, the two RFID tags 701A, 701B of the first product 701 are separated from the two RFID tags 702A, 702B of the second product 702. Hence, all RFID tags can be sensed by an antenna and can be read. The database operatively connected to such system will know which products have two tags, and which two tags they are, and thus knows if all four are read and that there are only two products.

However, when the two products 701, 702 are placed in one compartment in the orientation as shown in FIG. 70C, so that the RFID tag 701A of the first product 701 is in contact or in close proximity with the RFID tag 702B of the second product 702, those two tags 701A and 702B may interfere/cancel each other in which case those two RFID tags 701A,702B will not be sensed by the antenna. However, since the other two RFID tags 701B,702A are still separated from each other, those RFID tags 701B, 702A will not interfere or cancel each other and hence can still be sensed by the antenna and can still be read.

If in case, the first product 701 only had one RFID tag 701A and the second product 702 only had one RFID tag 702A and if those two RFID tags 701A,702A where in contact or within very close proximity to each other, then such RFID tags 701A, 702A are likely to interfere or cancel each other which case, neither of the RFID tags 701A, 702A will be sensed by the antenna and therefore will not be read. Therefore, it can be appreciated why having at least two RFID tags in a specific orientation in each product/item is preferred over having only one RFID tag on each product/item.

Optionally dividers are used to separate each item, the dividers make it difficult to insert a larger object (e.g. a bandage) in these slots.

To reduce cost one antenna can be placed between two or more such compartments and used to detect the objects in each compartment. If multiple compartments are covered by more than one antenna, the RSSI of each antenna can be used to triangulate the location of the product to determine where in the cabinet the item has been placed.

In some instances, additional and/or distributed storage capacity may be desirable, e.g. eyewash or plaster receptacles, which in large premises may be dotted around the premise. For these situations a separate storage cabinet or module remote from the cabinet may be provided that may be in communication with the cabinet using for example Bluetooth communication protocol. The use of Bluetooth and low power sensing allows the remote module to be powered by small replaceable batteries, e.g. coin cells. The remote module may monitor the state of the battery and initiate instructions to a person to change the batteries. The satellite-modules would include proximity sensing (e.g. capacitive pads, IR sensor, or similar) to detect use; take the processor (in the satellite-module) out of a low-power mode and monitor for changes using any one of the sensing methods herein described.

The cabinet may also have an audio and/or visual communication means such as speaker system that may play information about an item or items in the cabinet. This may play when requested or upon being triggered. A request for this information can be handled by one of the following ways. In one arrangement RFID tags may be located on the packaging of an item. The location of the RFID tag can be communicated to the end user by the use of a coloured dot or similar label. The user then places the package 'dot first' towards a readout panel, that has an RFID reader. When the cabinet scans the RFID tag, the audio can play pre-recorded product information or can fetch additional information from a database such as expiry date information. The cabinet will then play the appropriate audio and will notify the end user if the item has expired. Recordings can be updated periodically from a master database in the cloud. The Information can also be made available by a user with a NFC capable phone that can scan the product and the phone retrieves the information. Where the reader is in the cabinet, the cabinet could send the audio or data to a recipient's phone or tablet that had previously been registered in a database, or is connected via a Bluetooth link or similar wireless/Near Field Communications (NFC) technology, e.g. WIFI. Instead of audio, a visual communication of information may occur, such as by way of an LCD screen.

Figure 62:
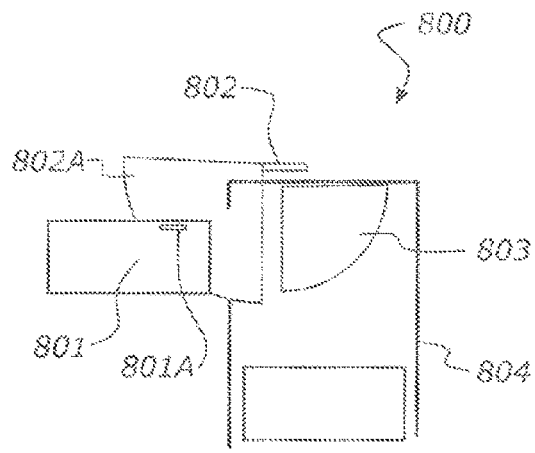
FIGS. 62-68 show how a package can be sensed to allow or dis-allow the package entering the cabinet.
Figure 63:
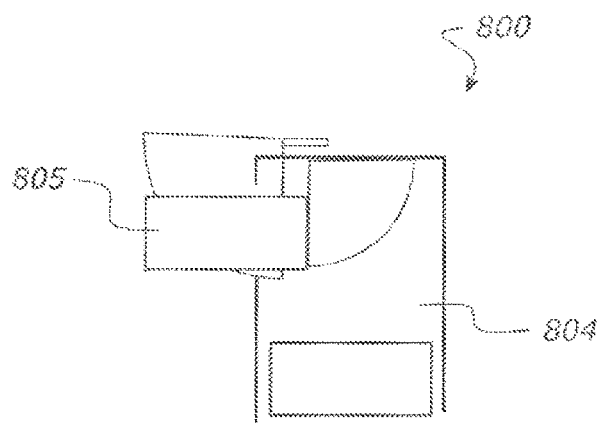
Figure 64:
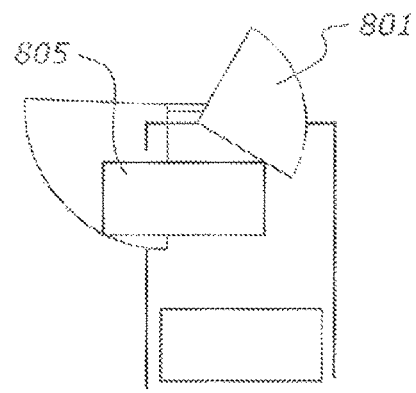
Figure 65:
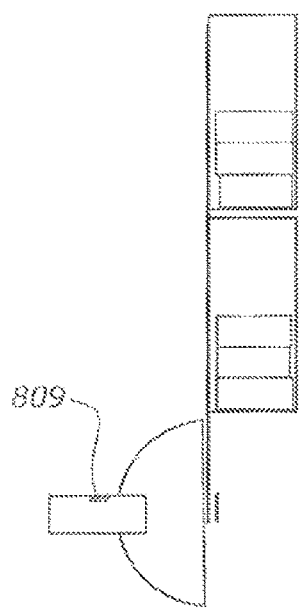
Figure 66:
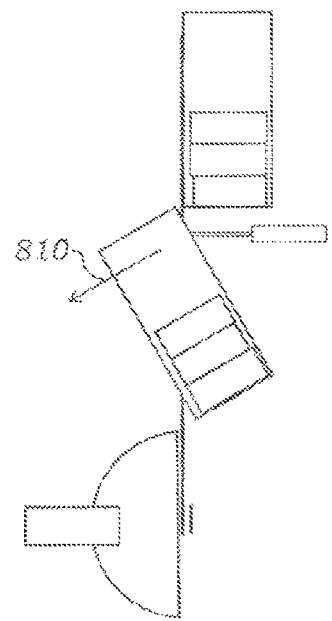
Figure 67:
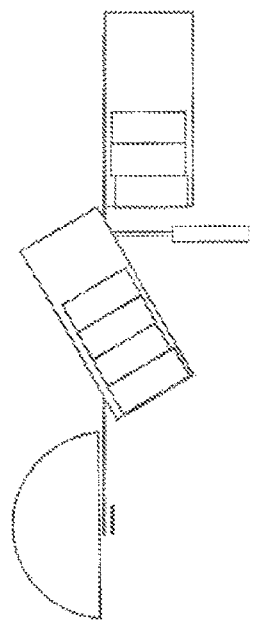
Figure 68:
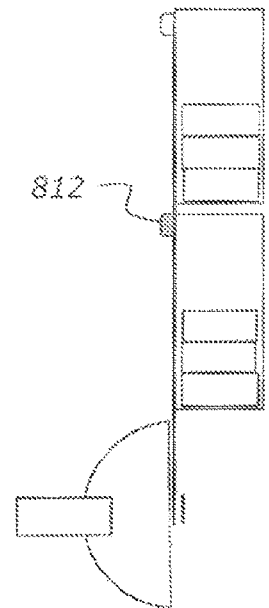

Reference will now be made to FIGS. 62-68. To help prevent the wrong item or package 805 being placed into a receptacle 804 of the cabinet 800, the cabinet may include an EID reader such as an RFID reader 802 having a reading zone 802a, that is able to cause a door or lock mechanism 803 to be activated or deactivated that can prevent the wrong product being placed in a receptacle. A package may contain an RFID tag 801A which is sensed by the RFID Reader of the cabinet as seen in FIGS. 62-64. The package may be scanned external of the cabinet and may then be validated or rejected. A door/lock mechanism which may control if product can be placed into the bin may be used. An RFID reader may check if a product is being placed in the correct location. If a user attempts to place the incorrect product or product that has been used (e.g. empty box) into a receptacle, the door/lock mechanism can prevent product being so placed. If the RFID reader confirms it is the correct product the door/lock mechanism will allow product to be placed in a receptacle. As seen in FIGS. 65-67 a cabinet may include a single RFID reader 808 that allows a user to scan a package containing an RFID tag 809 in close proximity to this reader. The RFID reader can then determine where product should be located and open the correct door 810 where product should be located, or the main door. Once product is confirmed to be in correct location the cabinet can be closed. This system could use other sensing methods such as barcodes, QR codes, colour, etc. As seen in FIG. 68, a light 812 may be used to indicate where product should be loaded. The light colour may change if product is loaded into incorrect location.

If it is desired to know the order of packs in a stack it is possible to do so. This could be achieved by having individual antenna's focused on each box (either with their own reader circuit, or multiplexed to one reader circuit), or one antenna shaped so that the received signal strength varies with box height. Two such antenna designs are presented below.

It will be appreciated that the EID information reading as herein described may be used together with capacitive sensing herein described. This can allow the device to determine:
(a) the level of content in each pack, by use of capacitive sensing,
(b) if an empty (or partially used) pack is placed back in a receptacle, because the capacitance reading is different from reading when the pack is full,
(c) when individual items in a pack are used, by use of capacitive sensing
(d) if a pack is open or opened, by use of EID sensing
(e) if a pack is in the right or wrong receptacle, by use of EID sensing,
(f) if a pack is in the wrong orientation in a receptacle, by use of the EID sensing.

Figure 69A:
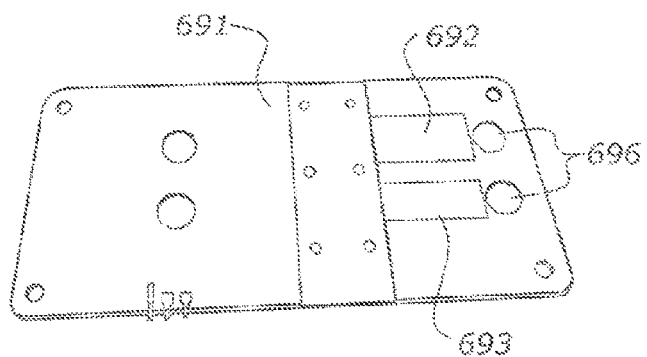
FIGS. 69A to 69C show an example configuration of a sensing arrangements on a printed circuit board for scissor/tweezer sensing.
Figure 69B:
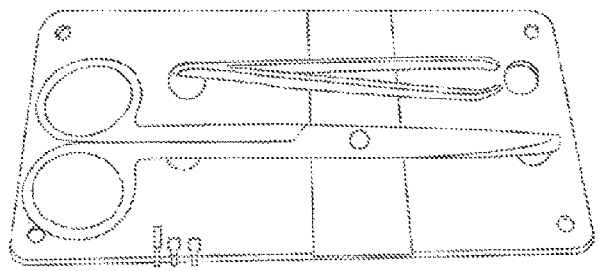
Figure 69C:
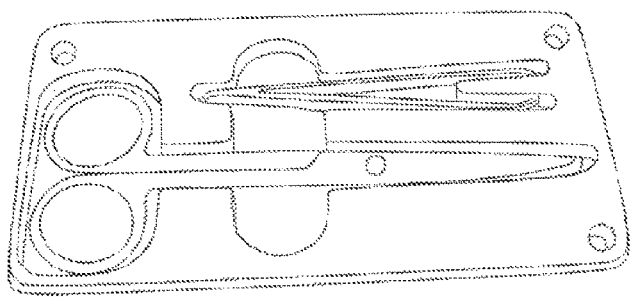

FIGS. 69A-69C show an example configuration of a capacitive sensing arrangements on a printed circuit board for scissor/tweezer sensing. The pads 691 and 692 form part of a printed circuit board.

The first pad 691 are second pad 692 function similar to fixed capacitive plates 37 and 38 as described above with reference to FIGS. 7 and 8. The second pad 692 is an active pad i.e. charged pad that receive a current and the first pad 691 is grounded. The first and second pads 691, 692 are preferably electrically conductive and made from a suitable material e.g. a metal and are preferably provided on the same plane as shown in FIG. 69A. FIG. 69B shows how the metal scissors and tweezers can bridge the second pad 692 which is the active pad to the first pad 691 which is the ground pad. Preferably, signal guard 693 may have a same potential as second pad 692 and therefore no capacitance in that direction.

When the scissor and/or tweezer are present, they contact the two pads 691, 692 and when the scissors and/or tweezers are removed, they do not contact the pads 691, 692. Similar to how electric field lines and capacitance changes depending upon the movement of metal plate 35 in FIGS. 7 and 8, the electric field lines and capacitance are larger with the scissors and/or tweezers contact(s) the two fixed pads 691, 692, and the electric field lines and capacitance are smaller when the scissor and/or tweezers is/are removed and therefore is/are longer in contact with two fixed pads 691, 692. With such arrangement, the presence or removal of the scissors and/or tweezers can be detected.

FIG. 69C shows how a cover part 695, which is preferably made from a plastic, is configured to cover the printed circuit board arrangement. The cover part 695 has cut outs/receptacles of shapes (and preferably also sizes) corresponding to those of the scissors and tweezers in order to ensure that scissors and tweezers are always placed correctly.

In FIG. 67A, mounting holes 696 are shown. The mounting holes may mount magnets in order to assist that the scissors and tweezers that are made out of a magnetic material are held in place when positioned inside the receptacle as shown in FIG. 69C.

Preferred embodiments of the invention have been described by way of example only and modifications may be made thereto without departing from the scope of the invention.

The invention claimed is:
1. A medical supplies cabinet comprising:
a housing presenting a medical supplies storage zone at where there is provided a plurality of medical supplies receptacles, the receptacle each being of a shape and configuration to be able to at least partly receive and hold at least one medical item:
a plurality of sensors associated with the receptacle, the sensors configured to generate signals indicative of the presence and/or absence or removal of the medical item(s) in/from respective receptacles; and
a door, the door pivotably connected to the housing and the door being moveable between an open position corresponding to the medical supplies storage zone being exposed for interaction by a user and a closed position where the door covers the medical supplies storage zone thereby preventing interaction by the user, wherein the housing includes a camera to make a recording of a view facing away from the medical supplies storage zone, and the door includes a mirror that is located to reflect a view of at least part of the medical supplies storage zone to the camera when the door is near its closed position such that the medical supplies storage zone is recordable by the camera when the door is near its closed position, wherein at least one of the receptacles is defined by a pair of parallel, spaced apart vertical walls and at least a base wall, a capacitive sensor disposed on or within the receptacle, and the capacitive sensor comprises a pair of sensing elements, wherein each sensing element is disposed on, adjacent or within one of the vertical walls such that the sensing elements are substantially parallel to each other and spaced apart from each other, wherein the capacitive sensor is one of the plurality of sensors and is configured to generate a signal indicative of the presence or number of medical items located in the receptacle between the pair of sensing elements, wherein medical items of at least two different kinds are each associated with differently configured RFID tags, and wherein an RFID tag reader is provided for at least one of the receptacles, the RFID tag reader being one of the plurality of sensors and arranged and configured to read the RFID tags and determine at least one of the following:

if a correct medical item is located at the respective receptacle, orientation of the medical item(s) when in the respective receptacle, and information carried by the RFID tag(s).

2. The medical supplies cabinet as claimed in claim 1, wherein the receptacles are discrete, at least two of the receptacles being of a shape to receive different said medical items.

3. The medical supplies cabinet as claimed in claim 1, wherein the capacitive sensor is configured to sense the addition or removal of the medical item(s) to and from the respective receptacle.

4. The medical supplies cabinet as claimed in claim 1, wherein the signal indicative of the presence of the medical item at the respective receptacle is proportional to the capacitance value of the capacitive sensor or a change in the capacitance of the capacitive sensor.

5. The medical supplies cabinet as claimed in claim 1, wherein at least one of the receptacles is shaped and configured to receive at least one of said medical item(s) or a package including a plurality of the medical items, where said medical item(s) are able to be individually removed from and/or added to the respective receptacle or the package at the respective receptacle, the sensor being associated with the respective receptacle and configured to provide a signal indicative of one or more of:

size of the package, number of medical items in the package or number of medical items in the respective receptacle, number of medical items removed from or added to the package, medical item(s) removed from or added to the respective receptacle, and orientation of medical item(s) in the respective receptacle.

6. The medical supplies cabinet as claimed in claim 1, wherein the plurality of sensors are each able to sense between at least one of:

presence and absence of the medical item(s) at the respective receptacle, presence of the correct medical item and medical incorrect item at the respective receptacle, and correct orientation and incorrect orientation of the medical item(s) or pack containing a plurality of said medical items at the respective receptacle.

7. The medical supplies cabinet as claimed in claim 1, comprising an optical sensing arrangement associated with at least one of the receptacles of the medical supplies cabinet, the optical sensing arrangement configured to generate a signal indicative of an identity or number of medical items within the respective receptacle or the state of the medical items(s) within the respective receptacle.

8. The medical supplies cabinet as claimed in claim 1, wherein at least one of the plurality of sensors is a load sensor configured to generate a signal indicative of the medical item(s) being removed from the respective receptacle by an application of a force.

9. The medical supplies cabinet as claimed in claim 1, comprising a processor to receive information from the plurality of sensors, the processor being configured to determine one or more of:

number of total medical items in the respective receptacles, types of medical items in the respective receptacles, number of medical items added to the respective receptacles, number of medical items removed from the respective receptacles, and orientation of one or more medical items in the respective receptacles.

10. The medical supplies cabinet as claimed claim 1 wherein at least one of the receptacles is of a shape and configuration to encourage the user to put only the medical items or pack containing at least one of said medical items in the respective receptacle by a matching of the same and configuration of the respective receptacle to the shape and configuration of the medical item(s) or pack containing at least one said medical item.

11. A method of reporting stock levels in the receptacles of the medical supplies cabinet as claimed in claim 1, the method comprising the steps of:

receiving the signal(s) from the sensor(s) associated with the respective receptacle, and processing the received signal(s) to determine the presence or absence or introduction/removal of the medical item(s) from the respective receptacle;

wherein the presence or absence or introduction/removal of the medical item(s) from the respective receptacle is based on a sensible characteristic or identification that is of or associated with the medical item(s).

12. The method of claim 11, wherein the sensible characteristic is of the weight of the medical item(s).

13. The method of claim 11, wherein the or one of the signal(s) is from the capacitive sensor associated with the respective receptacle, wherein said processing of the received signal to determine the presence or absence or introduction/removal of the medical item(s) from the respective receptacle is based on identifying at least one of:

a dielectric value and/or change in the dielectric value of the capacitive sensor as a result of the presence or movement or absence of the medical item(s) relative to the capacitive sensor, and the relative position and/or change in the relative position of the pair of sensing elements of the capacitive sensor.

14. The method of claim 11 wherein the method further comprises identifying an event based on the gradient or change in gradient of an output signal from the capacitive sensor.

15. The method of claim 11 wherein the sensible characteristic is of the presence or absence of the RFID tag associated with the medical item when in the proximity of the RFID tag reader.

* * * * *